(12) United States Patent
Townsend et al.

(10) Patent No.: US 6,214,801 B1
(45) Date of Patent: Apr. 10, 2001

(54) IMIDAZO[1,2-A]PYRIDINE C-NUCLEOSIDES AS ANTIVIRAL AGENTS

(75) Inventors: Leroy B. Townsend; John C. Drach, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/117,234

(22) PCT Filed: Jan. 22, 1997

(86) PCT No.: PCT/US97/01602

§ 371 Date: May 17, 1999

§ 102(e) Date: May 17, 1999

(87) PCT Pub. No.: WO97/27205

PCT Pub. Date: Jul. 31, 1997

Related U.S. Application Data

(60) Provisional application No. 60/010,463, filed on Jan. 23, 1996.

(51) Int. Cl.$^7$ .......................... A61K 31/70; C07H 17/01; A01N 43/04

(52) U.S. Cl. .......................... 514/23; 536/28.9; 536/29.2; 514/43

(58) Field of Search ................. 536/28.9, 29.2; 514/43, 23

(56) References Cited

U.S. PATENT DOCUMENTS

| | | | |
|---|---|---|---|
| 5,039,691 | * 8/1991 | Spagnuolo et al. | 514/393 |
| 5,248,672 | 9/1993 | Townsend et al. | 514/43 |
| 5,360,795 | 11/1994 | Townsend et al. | 514/43 |
| 5,459,132 | * 10/1995 | Bru-Magniez et al. | 514/46 |

FOREIGN PATENT DOCUMENTS

| | | |
|---|---|---|
| 0 238 070 | 12/1993 | (EP) . |
| 0 576 227 | 12/1993 | (EP) . |
| WO 91/01325 | 2/1991 | (WO) . |
| WO 92/07867 | 5/1992 | (WO) . |
| WO 94/08456 | 4/1994 | (WO) . |
| WO 95/23151 | 8/1995 | (WO) . |
| WO 96/01833 | 1/1996 | (WO) . |
| WO 97/07125 | 2/1997 | (WO) . |
| 9727205 | * 7/1997 | (WO) . |
| WO 97/27204 | 7/1997 | (WO) . |
| WO 98/35977 | 8/1998 | (WO) . |
| WO 98/56761 | 12/1998 | (WO) . |

OTHER PUBLICATIONS

Kaiser et al., "Synthesis and Antimuscarinic Properties of Some N–Substituted 5–(Aminomethyl)–3,3–diphenyl–2–(3H)–furanones," *Journal of Medicinal Chemistry*, 35(23), 4415–4424 (Nov. 13, 1992).*

Gudmundsson et al.(I), "Synthesis of Imidazo[1.2–a]pyridine C–Nucleosides with an Unexpected Site of Ribosylation," *Journal of Organic Chemistry*, 62(11), 3453–3459 (May 30, 1997).*

Gudmundsson et al.(II), "Synthesis of the First C3 Ribosylated Imidazo[1,2–a]pyridine C–Nucleoside by Enantioselective Construction of the Ribose Moiety," *Journal of Organic Chemistry*, 63(4), 984–989 (Feb. 20, 1998).*

Atrazhev et al., "2'–Deoxyribonucleoside 5'–Triphosphates Chemically Modified in the Base and Sugar Moieties as Substrates for DNA Biosynthesis in vitro," *Chemical Abstracts* 108:284 (abstract no. 108680j) (1988).

Blank, H. U. et al., "Uber die Tritylierung von Adenosin–Derivate," *Liebigs Ann. Chem.* 742:34–42 (1970).

Chu, C. K. et al., "Nucleosides 135. Synthesis of Some 9–(2–deoxy–2–fluoro–β–D–arabinofurnosyl)–9H–purines and Their Biological Activities," *Chem. Pharm. Bull.* 37:336–339 (1989). (Issue No. 2; Feb., 1989).

Codington, J.F. et al., "Synthesis of 2'–Fluorothymidine, 2'–Fluorodeoxyuridine, and Other 2'–Halogeno–2'–Deoxy Nucleosides," *Org. Chem.* 29:558–564 (1964). (Mar., 1964).

Cook et al., "Crystallization and Preliminary X–ray Investigation of Recombinant *Lactobacillus leichmannii* Nucleoside Deoxyribosyltransferase," *J. Biol. Chem.* 265:2682–2683 (1990). (Iss. No. 5; Feb. 15, 1990).

Devivar, R. et al., "Benzimidazole Ribonucleotides: Design, Synthesis, and Antiviral Activity of Certain 2–(Alkylthio)– and 2–(Benzylthio)–5,6–dichloro–(β–D–ribofuranosyl)benzimidazoles," *J. Med. Chem.* 37:2942–2949 (1994). (Iss. No. 18).

(List continued on next page.)

*Primary Examiner*—Gary Geist
*Assistant Examiner*—L E Crane
(74) *Attorney, Agent, or Firm*—Antoinette F. Konski; Baker & McKenzie

(57) ABSTRACT

This invention pertains to nucleoside analogs that have antiviral activity and improved metabolic stability, compositions comprising them, and methods of antiviral treatment employing them. More particularly, this invention pertains to imidazo[1,2-a]pyridine C-nucleosides, as exemplified by compounds such as imidazo[1,2-a]pyridine C5-nucleosides and imidazo[1,2-a]pyridine C3-nucleosides, and may be represented by formula (I), wherein exactly one of $Q^3$ and $Q^5$ is a sugar-like moiety; exactly one of $Q^3$ and $Q^5$ is —H; and $Q^2$, $Q^6$, $Q^7$ and $Q^8$ are independently imidazo[1,2-a]pyridine substituents, such as —H, —F, —Cl, —Br and —I.

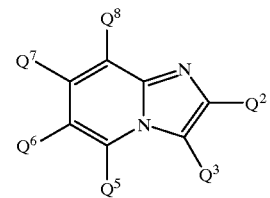

(I)

54 Claims, 15 Drawing Sheets

OTHER PUBLICATIONS

Devivar, R. et al., Fifth International Conference on Antiviral Research Vancouver, British Columbia; Abstract No. 106, Mar. 8–13, 1992.(Canada; Supplement 1).

Drach, J. C. et al., Fifth International Conference on Antiviral Research Vancouver, British Columbia; Abstract No. 12, Mar. 8–13, 1992. (Canada; Supplement 1).

Dyatkina et al., "Nucleosides of fluoro sugars. XV. Synthesis of 2', 3'–dideoxy–3'–fluoro–D–ribofuranosyl benzimidazole—a New Fluorosugar Purine Nucleoside Analog," *Chem. Abst.* 105:670 (abstract No. 24554w) (1986).

Gadler, H., "Nucleic Acid Hybridization for Measurement of Effects of Antiviral Compounds on Human Cytomegalovirus DNA Replication," *Antimicrobial Agents and Chemotherapy* 24:370–374 (1983). (Issue No. 3; Sep., 1983).

Good et al., "The Disposition in Rats and Monkeys of 2–Bromo–5,6–dichloro–1($\beta$–D–ribofuranosyl)–benzimidazole (BDCRB) and It's 2,5,6–Trichloro Congener (TCRB)," *Antiviral Research (Suppl. 1)* 23:103 (1994). (Abstract No. 128).

Graf, R., "Über einige 2.4–substituierte Derivate des Pyridins," *Ber.* 64:21–27 (1931).

Gudmundsson et al., "Palladium Catalysed Coupling of 2,6–Dichloro–3–iodoimidazo[1,2–$\alpha$]pyridine and 2,3–Dihydrofuran as an Approach to Novel Imidazo[1,2–$\alpha$]pyridine C–Nucleosides," *Tetrahedron Letters.* 37:6275–6278 (1996). (Iss. No. 36; Aug. 26, 1996).

Gudmundsson et al., "The Condensation of 2,6–Dichlororimidazo[1,2–$\alpha$]Pyridine with Ribonolactone Gives a Novel Imidazo[1,2–$\alpha$]pyridine C–nucleoside with an Unexpected Site of Ribosylation," *Tetrahedron Letters.* 37:2365–2368 (1996). (Iss. No. 14; Apr. 1, 1996).

Herdewijn, P. et al., "Synthesis of Nucleosides Fluorinated in the Sugar Moiety. The Application of Diethylaminosulfur Trifluoride to the Synthesis of Fluorinated Nucleosides," *Nucleosides and Nucleotides* 8:65–96 and references therein (1989). (Iss. No. 1).

Howell, H.G. et al., "Antiviral Nucleosides. A Stereospecific, Total Synthesis of 2'–Fluoro–2'–deoxy–$\beta$–D–arabinofuranosyl Nucleosides," *J. Org. Chem.* 53:85–88 (1988). (Iss. No. 1).

Kang et al., "A Synthetic Study on Trans–2,5 Disubstituted Tetrahydrofurans via Phenylselenoetherification," *Bull. Korean Chem. Soc.* 11:455–460 (1990). (Iss. No. 5).

Krezeminski, J. et al., "Synthesis of 9–(2–Deoxy–2–fluoro–$\beta$–D–arabinofuranosyl)hyoxanthine. The First Direct Introduction of a 2'–$\beta$–Fluoro Substituent in Preformed Purine Nucleosides. Studies Directed Toward The Synthesis of 2'–Deoxy–2'–Substituted Arabinucleosides," *Nucleosides and Nucleotides* 10, 781–798 (1991).(Iss. #4).

Kucera et al., "Activity of Triciribine and Triciribine–5'–Monophosphate Against Human Immunodeficiency Virus Types 1 and 2," *AIDS Res. Human Retroviruses* 9:307–314 (1993).(#4).

Lombardino, J., "Synthesis and Antiinflammatory Activity of Metabolites of Piroxicam," *J. Med. Chem.* 24:39–42 (1961). (Issue No. 1).

Matsumura, E. et al., "Studies of the Reissert–Kaufmann–type Reaction of 4–Nitropyridine N–Oxide and Its Homologues," *Bull. Chem. Soc. Jpn.* 43:3210–3214 (1970). (Iss. #10; Oct., '1970).

Montgomery, J. A. et al., "9–(2–Deoxy–2–fluoro–$\beta$–D–arabinofuranosyl)guanine: A Metabolically Stable Cytotoxic Analogue of 2'–Deoxyguanosine," *J. Med. Chem.* 29:2389–2392 (1986). (Issue No. 11).

Mosher, H.S. et al., "Heterocyclic Basic Compounds. XVI. 4–Chloropicolinic Acid and Some of its Derivatives," *J. Org. Chem.* 20:283–286 (Mar., 1955).

Nassiri, S. R. et al., Fifth International Conference on Antiviral Research Vancouver, British Columbia; Abstract No. 107, Mar. 8–13, 1992. (Canada, Supplement 1).

Nassiri, S. R. et al., Fifth International Conference on Antiviral Research Vancouver, British Columbia; Abstract No. 108, Mar. 8–13, 1992. (Canada, Supplement 1).

Pankiewicz, K. W. et al., "A Synthesis of 9–(2–Deoxy–2–fluoro–$\beta$–D–arabinofuranosyl)adenine and Hypoxanthine. An Effect of C3'–Endo to C2'–Endo Conformational Shift on the Reaction Course of 2'–Hydroxyl Group with DAST," *J. Org. Chem.* 57:553–559 (1992). (Issue No. 2).

Pankiewicz, K. W. et al., "A Synthesis of 2'–Fluoro–Substituted Purine Nucleosides via a Direct Approach. In Nucleosides as Antitumor and Antiviral Agents," Chu, C. K.; Baker, D. C., Eds.; Plenum Press: New York, pp 55–71 (1993).

Perrin, D.D.; Armarego, W.L.F., Purification of Laboratory Chemicals, 3rd Ed., Pergamon Press, N.Y. 1988. (Table of Contents).

Prichard, M. N. et al., "A microtiter virus yield reduction assay for the evaluation of antiviral compounds against human cytomegalovirus and herpes simplex virus," *J. Virol. Methods* 28:101–106 (1990).

Prichard, M. N. et al., "A Three–Dimensional Model to Analyze Drug–Drug Interactions," *Antiviral Res.* 15:114 (abstract No. 133) (1991). (Supplement 1; Apr., 1991).

Prichard, M. N. et al., "Three Dimensional Analysis of the Synergistic Cytotoxicity of Ganciclovir and Zidovudine," *Antimicrobial Agents & Chemother.*, 35(6), 1060–1065(Jun. 1991).

Reichman, U. et al., "A Practical Synthesis of 2–Deoxy–2–Fluoro–D–Arabinofuranose Derivatives," *Carbohydr. Res.* 42:233–240 (1975).

Revenkar, R. G. et al., "The Synthesis of 2–Chloro–1–($\beta$–D–ribofuranosyl–5,6–dimethylbenzimidazole and Certain Related Derivatives," *J. Heterocyclic Chem.* 5:477–483 (1968). (Aug., 1968).

Revenkar, R. G. et al., "The Synthesis of 2–Chloro–1–($\beta$–D–ribofuranosyl)benzimidazole and Certain Related Derivatives," *J. Heterocyclic Chem.* 5:615–620 (1968). (Oct., 1968).

Saluja, S. et al., "Synthesis and antiviral activity of certain 2–substituted–5,6–dichlorobenzimidazole acyclic nucleosides," Poster #146. Division of Medicinal Chemistry, 204th American Chemical Society National Meeting, Washington, D.C., Aug. 23–28 (1992).

Sharpless, K.B. et al., "The Osmium–Catalyzed Asymmetric Dihydroxylation: A New Ligand Class and a Process Improvement," *J. Org. Chem.* 57:2768–2771 (1992). (Iss. No. 10).

Shipman, C., Jr. et al., "Antiviral Activity of Arabinosyladenine and Arabinosylhypoxanthine in Herpes Simples Virus–Infected KB Cells: Selective Inhibition of Viral Deoxyribonucleic Acid Synthesis in Synchronized Suspension Cultures," *Antimicrobial Agents Chemotherapy* 9:120–127 (1976). (Issue No. 1, Jan., 1976).

Still, W. C. et al., "Rapid Chromatographic Techniques for Preparative Separation with Moderate Resolution," *J. Org. Chem.* 43:2923–2925 (1978). (Iss. No. 14).

Sullivan, V. et al., "A Point Mutation in the Human Cytomegalovirus DNA Polymerase Gene Confers Resistance to Ganciclovir and Phosphonylmethoxyalkyl Derivatives," *Antimicrobial Agents and Chemotherapy* 37:19–25 (1993).(Iss. No. 1; Jan., 1993).

Tamm, I., "Inhibition of Influenza and Mumps Virus Multiplication by 4,5,6– (or 5,6,7–)Trichloro–1–β–D–Ribofuranosyl–benzimidazole," *Science* 120:847–848 (1954). (Nov. 19, 1954).

Tann, C. H. et al., "Fluorocarbohydrates in Synthesis: An efficient Synthesis of 1–(2–Deoxy–2–fluoro–β–D–arabinofuranosyl)–5–iodouracil (β–FIAU) and 1–(2–Deoxy–2–fluoro–β–D–arabinofuranosyl)thymine (β–FMAU)," *J. Org. Chem.* 50:3644–3647 (1985). (Iss. No. 19).

Thiem, J. et al., "Synthesis and Perkow Reaction of Uridine Derivatives," *Nucleosides and Nucleotides* 4:487 (1985). (Issue No. 4).

Townsend et al., "Benzimidazole Nucleosides , Nucleotides, and Related Derivatives," *Chem. Rev.* 70:389–438 (1970). (Issue No. 3).

Townsend et al., "Design, Synthesis, and Antiviral Activity of Certain 2,5,6–Trihalo–1–(B–D–ribofuranosyl) Benzimidazoles," *J. Med. Chem.* 38:4098–4105 (1995).(Iss. No. 20).

Turk, S. R. et al., Fifth International Conference on Antiviral Research Vancouver, British Columbia; Abstract No. 109, Mar. 8–13, 1992.(Canada, Supplement 1).

Turk, S. R. et al., Fifth International Conference on Antiviral Research, Vancouver, British Columbia; Abstract No. 110, Mar. 8–13, 1992. (Supplement 1, Canada).

Turk, S. R. et al., "Pyrrolo[2,3–d]Pyrimidine Nucleosides as Inhibitors of Human Cytomegalovirus," *Antimicrobial Agents and Chemotherapy* 31:544–550 (1987). (#4; Apr. 1987).

White et al., "A TIBO derivative, R82913, is a potent inhibitor of HIV–1 reverse transcriptase with heteropolymer templates," *Antiviral Res.* 16:257–266 (1991).

Wright, J. A. et al., "Nucleosides. LX. Fluorocarbohydrates. XXII. Synthesis of 2–deoxy–2–fluoro–D–arabinose and 9–(2–deoxy–2–fluoro–α and β–arabinofuranosyl)adenines," *J. Org. Chem.* 34:2632–2636 (1969). (Issue No. 1, Sep., 1969).

Zou, R. et al., "Design, synthesis and antiviral evaluation of some TCRB analogs modified on the benzene moiety," Poster #142. Division of Medicinal Chemistry, 204th American Chemical Society National Meeting, Washington, D. C., Aug. 23–28, 1992.

Zou, R. et al., Fifth International Conference on Antiviral Research, Vancouver, British Columbia; Abstract No. 105, Mar. 8–13, 1992. (Canada, Supplement 1).

* cited by examiner

IMIDAZO[1,2-A]PYRIDINE C-NUCLEOSIDES AS ANTIVIRAL AGENTS

This application is a 371 of PCT/US97/01602, filed Jan. 22, 1997 which claims priority under 37 C.F.R. § 119(e) to U.S. Provisional Application No. 60/010,463, filed Jan. 23, 1996.

FIELD OF THE INVENTION

This invention pertains to nucleoside analogs which have antiviral activity and low cytotoxicity, compositions comprising them, and methods of antiviral treatment employing them. More particularly, this invention pertains to imidazo[1,2-a]pyridine C-nucleosides, as exemplified by compounds such imidazo[1,2-a]pyridine C5-nucleosides and imidazo[1,2-a]pyridine C3-nucleosides.

BACKGROUND OF THE INVENTION

Benzimidazole nucleosides are particularly attractive as potential antiviral agents because of their ability to avoid some major pathways of bioactive purine (bicyclic) nucleoside inactivation, e.g., deamination by adenosine deaminase and glycosidic bond cleavage by purine nucleoside phosphorylases. For example, current therapy for HCMV includes the use of drugs such as ganciclovir (also known as DHPG), foscanet, and cidofovir. However, known benzimidazole nucleosides such as 5,6-dichloro-1-(β-D-ribofuranosyl) benzimidazole (DRB) have demonstrated only marginal levels of activity or generally unacceptable levels of cytotoxicity, or both, thereby greatly diminishing their usefulness in the treatment of viral infections. Recently, benzimidazole compounds, such as TCRB (2,5,6-trichloro-1-(2'-β-D-ribofuranosyl)-benzimidazole) and BDCRB (2-bromo-5,6-dichloro-1-(2'-β-D-ribofuranosyl)-benzimidazole) have also been found to be useful against HCMV infections. See, for example, Townsend et al., J. Med. Chem., Vol. 38, pp. 4098–4105 (1995).

A number of benzimidazole nucleosides have been synthesized and tested for their antiviral activity and cytotoxicity in an effort to identify a compound with superior anti-human cytomegalovirus (HCMV) activity to ganciclovir and foscamet. Antiviral activity of polysubstituted benzimidazoles such as 5,6-dichloro-1-(-β-D-ribofuranosyl) benzimidazole (DRB) and some closely related derivatives have been previously described (I. Tamm, Science (1954) Vol. 120:847–848). Their activity against specific viruses, such as RNA rhinovirus and DNA herpes simplex virus type 1 and type 2, also has been reported.

Several of the 5'-deoxyribosyl benzimidazole analogs, including 2,5,6-trichloro-1-(-β-D-ribofuranosyl) benzimidazole (TCRB) have shown very potent activity against HCMV and low cellular toxicity at concentrations inhibiting viral growth. Structural activity relationships of TCRB and heterocycle and carbohydrate modified derivatives have been reported. (See, Revenkar, R. G. and Townsend, L. B. (1968) J. Heterocyclic Chem. Vol. 5:477–483; Townsend, L. B. and Drach, J. C., Fifth International Conference on Antiviral Research Vancouver, British Columbia, March 1992; Revenkar, R. G. and Townsend, L. B. (1968) J. Heterocvclic Chem. Vol. 5:615–620; Zou, R. et al. "Design, synthesis and antiviral evaluation of some TCRB analogs modified on the benzene moiety" Poster #142. Division of Medicinal Chemistry, 204th American Chemical Society National Meeting, Washington, D. C., Aug. 23–28, 1992; and Saluja, S. et al. "Synthesis and antiviral activity of certain 2-substituted-5,6-dichlorobenzimidazole acyclic nucleosides. Poster #146. Division of Medicinal Chemistry, 204th American Chemical Society National Meeting, Washington, D. C., Aug. 23–28, 1992.)

The present invention pertains to imidazo[1,2-a]pyridines, which are structurally analogous to benzimidazoles, as illustrated below. The imidazo[1,2-a]pyridines of the present invention have been shown to have antiviral activity and low cytotoxicity.

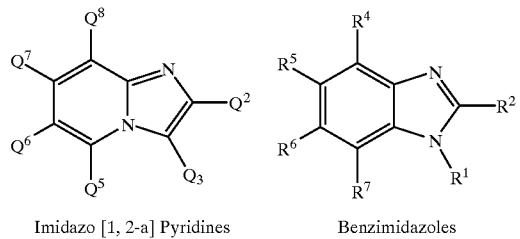

Imidazo [1, 2-a] Pyridines    Benzimidazoles

Throughout this application, various publications, patents, and published patent applications are referred to by an identifying citation. The disclosures of the publications, patents, and published patent specifications referenced in this application are hereby incorporated by reference into the present disclosure to more fully describe the state of the art to which this invention pertains.

SUMMARY OF THE INVENTION

One aspect of the present invention pertains to imidazo[1,2-a]pyridine C-nucleosides, such as imidazo[1,2-a]pyridine C3-nucleosides and imidazo[1,2-a]pyridine C5-nucleosides, as described herein.

Another aspect of the present invention pertains to pharmaceutical compositions for treating viral infections which comprise a therapeutically effective amount of one or more of the imidazo[1,2-a]pyridine C-nucleosides of the present invention, as described herein.

Yet another aspect of the present invention pertains to methods for treating viral infections in an animal patient comprising the step of administering a therapeutically effective amount of one or more of the imidazo[1,2-a]pyridine C-nucleosides of the present invention, as described herein.

Still another aspect of the present invention pertains to methods for inhibiting viral (e.g., HCMV) proliferation in a virally infected cell comprising contacting the cell with an effective amount of one or more of the imidazo[1,2-a]pyridine C-nucleosides of the present invention, as described herein, under suitable conditions such that viral proliferation is inhibited.

Still another aspect of the present invention pertains to methods for prophylactically treating a cell susceptible to viral (e.g., HCMV) infection, by contacting the cell with an effective amount of one or more of the imidazo[1,2-a]pyridine C-nucleosides of the present invention, as described herein, under suitable conditions such that viral infection is prevented.

As will become apparent, preferred features and characteristics of one aspect of the invention are applicable to any other aspect of the invention.

DESCRIPTION OF THE PREFERRED EMBODIMENT

Figure 1:
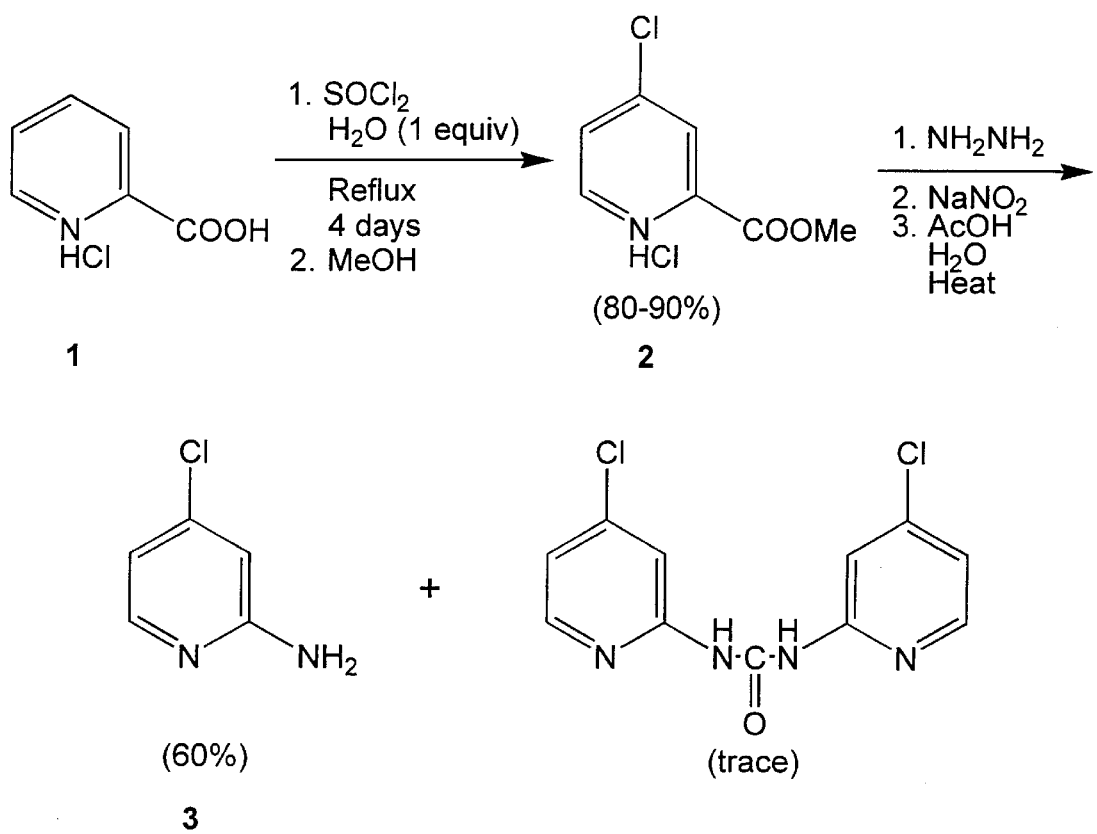
FIG. 1 is a flowchart illustrating a method for the chemical synthesis of 2-amino-4-chloro-pyridine.

A. Antiviral Compounds of the Present Invention

This invention pertains to imidazo[1,2-a]pyridine C-nucleosides, more specifically, imidazo[1,2-a]pyridine C3-nucleosides and imidazo[1,2-a]pyridine C5-nucleosides, which have antiviral activity and low toxicity a nd which offer improved metabolic stability, and therefore, longer half-lives in vivo.

The compounds of the present invention may be described as "modified heterocycles" or "imidazopyridines," wherein the ring structure is that of an imidazo[1,2-a]pyridine (which is structurally similar to the benzimidazole ring structure). Nucleosides of these imidazo[1,2-a]pyridines may be formed by attaching a sugar-like moiety at the C3-position (on the 5-membered ring, i.e., $Q^3$) to yield a "C3-nucleoside" or "imidazo[1,2-a]pyridine C3-nucleoside," or at the C5-position (on the 6-membered ring, i.e., $Q^5$) to yield a "C5-nucleoside" or "imidazo[1,2-a]pyridine C5-nucleoside." These compounds may be represented by the following formula,

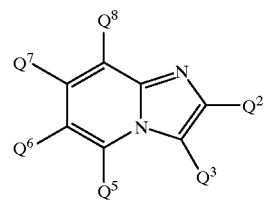

wherein exactly one of $Q^3$ and $Q^5$ is a sugar-like moiety; exactly one of $Q^3$ and $Q^5$ is —H; and $Q^2$, $Q^6$, $Q^7$, and $Q^8$ are independently imidazo[1,2-a]pyridine substituents. Examples of imidazo[1,2-a]pyridine substituents include —H, —F, —Cl, —Br, and —I.

In one embodiment of the present invention (C3 Nucleosides), $Q^3$ is a sugar-like moiety and $Q^5$ is —H. In one embodiment of the present invention (C5 Nucleosides), $Q^3$ is —H and $Q^5$ is a sugar-like moiety.

In one embodiment of the present invention, $Q^2$ and $Q^6$ are —X; and Q and QS are —H, wherein X is —F, —Cl, —Br or —I. In another embodiment of the present invention, $Q^2$ and $Q^7$ are —X; and $Q^6$ and $Q^8$ are —H. In another embodiment of the present invention, $Q^2$, $Q^6$ and $Q^7$ are —X; and $Q^8$ is —H. In another embodiment of the present invention, $Q^2$, $Q^7$ and $Q^8$ are —X; and $Q^6$ is —H. In another embodiment of the present invention, $Q^2$, $Q^6$, $Q^7$ and $Q^8$ are —X.

The term "sugar-like moiety" as used herein relates to monosaccharide moieties. Preferred sugar-like moieties are in cyclic form, for example, derived from furanose (5-membered ring) or from pyranose (6-membered ring) forms, but more preferably from fulranose forms. Examples of sugar-like moieties include threo-furanosyl (from threose, a four-carbon sugar); erythro-furanosyl (from erythrose, a four-carbon sugar); ribo-furanosyl (from ribose, a five-carbon sugar); ara-furanosyl (from arabinose, a five-carbon sugar); and xylo-furanosyl (from xylose, a five-carbon sugar). Also encompassed by the term "sugar-like moiety" are sugar-like moieties having further modifications, for example, "deoxy," "keto," "dehydro," and "deoxy-dehydro" derivatives, including, but not limited to, 2'-deoxy-ribo-furanosyl; 3'-deoxy-ribo-furanosyl; 3'-keto-2'-deoxy-ribo-furanosyl; 2',5'-dihydrofuran-2'-yl; 2',3'-dihydrofuran-2'-yl; 2',3'-dideoxy-2',3'-didehydro-ribo-furanosyl; and 2',3'-dideoxy-3',4'-didehydro-ribo-furanosyl.

Sugar-like moieties may be in any of their enantiomeric, diasteriomeric, or stereoisomeric forms, including, for example, D- or L-forms. The imidazo[1,2-a]pyridine nucleosides of the present invention may be in any stereochemical configuration, including, for example, α- or β-anomeric form.

As used herein, the term "sugar-like moiety" also encompasses protected sugar-like moieties. For example, sugar-like moieties may possess one or more of 2'-hydroxyl, 3'-hydroxyl, and/or 5'-hydroxyl groups in a protected form, for example, as an ester (e.g., as an acetate, —O(C=O) $CH_3$), benzoate (i.e., —OC(=O)$C_6H_5$), or an ether (e.g., as a trityl ether, —OC($C_6H_5$)$_3$). Also, adjacent 2'- and 3'-hydroxyl groups may be protected with a 2',3'-O-isopropylidine group.

Throughout this application the disclosed and claimed compounds are identified by structure, name or by numerical designations. The compounds of this invention include, but are not limited to those examples shown below.

Examples of imidazo[1,2-a]pyridine C3-nucleosides of the present invention include:

3-(furanosyl)-imidazo[1,2-a]pyridine
2,6-dichloro-3-(furanosyl)-imidazo[1,2-a]pyridine
2,7-dichloro-3-(furanosyl)-imidazo[1,2-a]pyridine
2,6,7-trichloro-3-(furanosyl)-imidazo[1,2-a]pyridine
2,7,8-trichloro-3-(furanosyl)-imidazo[1,2-a]pyridine
3-(ribo-firanosyl)-imidazo[1,2-a]pyridine
2,6-dichloro-3-(ribo-furanosyl)-imidazo[1,2-a]pyridine
2,7-dichloro-3-(ribo-furanosyl)-imidazo[1,2-a]pyridine
2,6,7-trichloro-3-(ribo-furanosyl)-imidazo[1,2-a]pyridine
2,7,8-trichloro-3-(ribo-furanosyl)-imidazo[1,2-a]pyridine
3-(lyxo-furanosyl)-imidazo[1,2-a]pyridine
2,6-dichloro-3-(lyxo-furanosyl)-imidazo[1,2-a]pyridine
2,7-dichloro-3-(lyxo-furanosyl)-imidazo[1,2-a]pyridine
2,6,7-trichloro-3-(lyxo-furanosyl)-imidazo[1,2-a]pyridine
2,7,8-trichloro-3-(lyxo-furanosyl)-imidazo[1,2-a]pyridine
3-(erythro-firanosyl)-imidazo[1,2-a]pyridine
2,6-dichloro-3-(erythro-furanosyl)-imidazo[1,2-a]pyridine
2,7-dichloro-3-(erythro-furanosyl)-imidazo[1,2-a]pyridine
2,6,7-trichloro-3-(erythro-furanosyl)-imidazo[1,2-a]pyridine
2,7,8-trichloro-3-(erythro-furanosyl)-imidazo[1,2-a]pyridine
3-(2',3'-dideoxy-2',3'-erythro-furanosyl)-imidazo[1,2-a]pyridine
2,6-dichloro-3-(2',3'-dideoxy-2',3'-didehydro-erythro-furanosyl)-imidazo[1,2-a]pyridine
2,7-dichloro-3-(2',3'-dideoxy-2',3'-didehydro-erythro-furanosyl)-imidazo[1,2-a]pyridine
2,6,7-trichloro-3-(2',3'-dideoxy-2',3'-didehydro-erythro-furanosyl)-imidazo[1,2-a]pyridine
2,7,8-trichloro-3-(2',3'-dideoxy-2',3'-didehydro-erythro-furanosyl)-imidazo[1,2-a]pyridine
3-(2',3'-dideoxy-3',4'-didehydro-erythro-fiuranosyl)-imidazo[1,2-a]pyridine
2,6-dichloro-3-(2',3'-dideoxy-3',4'-didehydro-erythro-furanosyl)-imidazo[1,2-a]pyridine
2,7-dichloro-3-(2',3'-dideoxy-3',4'-didehydro-erythro-furanosyl)-imidazo[1,2-a]pyridine
2,6,7-trichloro-3-(2',3'-dideoxy-3',4'-didehydro-erythro-furanosyl)-imidazo[1,2-a]pyridine
2,7,8-trichloro-3-(2',3'-dideoxy-3',4'-didehydro-erythro-furanosyl)-imidazo[1,2-a]pyridine
3-(2',3'-dideoxy-2',3'-didehydro-ribo-furanosyl)-imidazo[1,2-a]pyridine
2,6-dichloro-3-(2',3'-dideoxy-2',3'-didehydro-ribo-furanosyl)-imidazo[1,2-a]pyridine
2,7-dichloro-3-(2',3'-dideoxy-2',3'-didehydro-ribo-furanosyl)-imidazo[1,2-a]pyridine
2,6,7-trichloro-3-(2',3'-dideoxy-2',3'-didehydro-ribo-furanosyl)-imidazo[1,2-a]pyridine
2,7,8-trichloro-3-(2',3'-dideoxy-2',3'-didehydro-ribo-furanosyl)-imidazo[1,2-a]pyridine
3-(2',3'-dideoxy-3',4'-didehydro-ribo-furanosyl)-imidazo[1,2-a]pyridine
2,6-dichloro-3-(2',3'-dideoxy-3',4'-didehydro-ribo-furanosyl)-imidazo[1,2-a]pyridine
2,7-dichloro-3-(2',3'-dideoxy-3',4'-didehydro-ribo-furanosyl)-imidazo[1,2-a]pyridine
2,6,7-trichloro-3-(2',3'-dideoxy-3',4'-didehydro-ribo-furanosyl)-imidazo[1,2-a]pyridine
2,7,8-trichloro-3-(2',3'-dideoxy-3',4'-didehydro-ribo-furanosyl)-imidazo[1,2-a]pyridine Examples of imidazo[1,2-a]pyridine C5-nucleosides of the present invention include:
5-(furanosyl)-imidazo[1,2-a]pyridine
2,6-dichloro-5-(furanosyl)-imidazo[1,2-a]pyridine
2,7-dichloro-5-(furanosyl)-imidazo[1,2-a]pyridine
2,6,7-trichloro-5-(furanosyl)-imidazo[1,2-a]pyridine
2,7,8-trichloro-5-(furanosyl)-imidazo[1,2-a]pyridine
5-(ribo-furanosyl)-imidazo[1,2-a]pyridine
2,6-dichloro-5-(ribo-furanosyl)-imidazo[1,2-a]pyridine
2,7-dichloro-5-(ribo-furanosyl)-imidazo[1,2-a]pyridine
2,6,7-trichloro-5-(ribo-furanosyl)-imidazo[1,2-a]pyridine
2,7,8-trichloro-5-(ribo-furanosyl)-imidazo[1,2-a]pyridine
5-(lyxo-furanosyl)-imidazo[1,2-a]pyridine
2,6-dichloro-5-(lyxo-furanosyl)-imidazo[1,2-a]pyridine
2,7-dichloro-5-(lyxo-furanosyl)-imidazo[1,2-a]pyridine
2,6,7-trichloro-5-(lyxo-furanosyl)-imidazo[1,2-a]pyridine
2,7,8-trichloro-5-(lyxo-furanosyl)-imidazo[1,2-a]pyridine
5-(erythro-furanosyl)-imidazo[1,2-a]pyridine
2,6-dichloro-5-(erythro-furanosyl)-imidazo[1,2-a]pyridine
2,7-dichloro-5-(erythro-furanosyl)-imidazo[1,2-a]pyridine
2,6,7-trichloro-5-(erythro-furanosyl)-imidazo[1,2-a]pyridine
2,7,8-trichloro-5-(erythro-furanosyl)-imidazo[1,2-a]pyridine
5-(2',3'-dideoxy-2',3'-didehydro-erythro-furanosyl)-imidazo[1,2-a]pyridine
2,6-dichloro-5-(2',3'-dideoxy-2',3'-didehydro-erythro-furanosyl)-imidazo[1,2-a]pyridine
2,7-dichloro-5-(2',3'-dideoxy-2',3'-didehydro-erythro-furanosyl)-imidazo[1,2-a]pyridine
2,6,7-trichloro-5-(2',3'-dideoxy-2',3'-didehydro-erythro-furanosyl)-imidazo[1,2-a]pyridine
2,7,8-trichloro-5-(2',3'-dideoxy-2',3'-didehydro-erythro-firanosyl)-imidazo[1,2-a]pyridine
5-(2',3'-dideoxy-3',4'-didehydro-erythro-furanosyl)-imidazo[1,2-a]pyridine
2,6-dichloro-5-(2',3'-dideoxy-3',4'-didehydro-erythro-furanosyl)-imidazo[1,2-a]pyridine
2,7-dichloro-5-(2',3'-dideoxy-3',4'-didehydro-erythro-furanosyl)-imidazo[1,2-a]pyridine
2,6,7-trichloro-5-(2',3'-dideoxy-3',4'-didehydro-erythro-furanosyl)-imidazo[1,2-a]pyridine
2,7,8-trichloro-5-(2',3'-dideoxy-3',4'-didehydro-erythro-furanosyl)-imidazo[1,2-a]pyrid
5-(2',3'-dideoxy-2',3'-didehydro-ribo-furanosyl)-imidazo[1,2-a]pyridine
2,6-dichloro-5-(2',3'-dideoxy-2',3'-didehydro-ribo-furanosyl)-imidazo[1,2-a]pyridine
2,7-dichloro-5-(2',3'-dideoxy-2',3'-didehydro-ribo-furanosyl)-imidazo[1,2-a]pyridine
2,6,7-trichloro-5-(2',3'-dideoxy-2',3'-didehydro-ribo-furanosyl)-imidazo[1,2-a]pyridine
2,7,8-trichloro-5-(2',3'-dideoxy-2',3'-didehydro-ribo-furanosyl)-imidazo[1,2-a]pyridine
5-(2',3'-dideoxy-3',4'-didehydro-ribo-furanosyl)-imidazo[1,2-a]pyridine
2,6-dichloro-5-(2',3'-dideoxy-3',4'-didehydro-rybo-furanosyl)-imidazo[1,2-a]pyridine
2,7-dichloro-5-(2',3'-dideoxy-3',4'-didehydro-rybo-furanosyl)-imidazo[1,2-a]pyridine
2,6,7-trichloro-5-(2',3'-dideoxy-3',4'-didehydro-ribo-furanosyl)-imidazo[1,2-a]pyridine
2,7,8-trichloro-5-(2',3'-dideoxy-3',4'-didehydro-ribo-furanosyl)-imidazo[1,2-a]pyridine The compounds of this invention are useful in the methods provided below or are useful as intermediates for the manufacture of these compounds. It also should be understood, even though not always explicitly stated, that reference to any of the above compounds is to include pharmaceutically acceptable salts and operative combinations thereof.

B. Methods of Using the Antiviral Compounds of the Present Invention

As shown below, the compounds of this invention are potent antiviral drugs, and are particularly effective against HCMV and HSV-1, and as such, when combined with carriers, provide compositions for inhibiting viral reproduction and proliferation in vitro, ex vivo or in vivo. For example, the compounds can be combined with various liquid phase carriers, such as sterile or aqueous solutions, pharmaceutically acceptable carriers as defined below.

The compounds of this invention can be combined with other antiviral drugs to provide an operative combination. "Operative combination" is intended to include any chemically compatible combination of a compound of this inventive group with other compounds of the inventive group or other compounds outside the inventive group (such as ganciclovir, AZT, and focarnet), as long as the combination does not eliminate the antiviral activity of the compound of this inventive group.

The compounds of the invention could be used to treat HCMV and HSV-1 infections in AIDS patients already receiving the antiviral drug zidovudine (AZT). Combination therapies with AZT may provide the advantage of less toxicity over the combination of ganciclovir with AZT. The combination of the compounds of this invention with AZT may produce less cytotoxicity (i.e. antagonism) in cultured human cells than either agent used alone. In contrast, combination of ganciclovir with AZT may produce greater cytotoxicity in human cells than the use of either of these drugs alone.

This invention also provides a method of reducing or inhibiting HCMV or HSV-1 reproduction and proliferation in an HCMV or HSV-1 infected cell or population of cells by contacting the cell or population with an effective amount of a compound of this invention and under suitable conditions, such that viral reproduction and proliferation is inhibited. One of skill in the art can easily determine when HCMV or HSV-1 reproduction and proliferation has been reduced or inhibited by noting a reduction in viral titer or an increase of survival of the infected cells as compared to untreated, infected cells. Methods of assaying viral titer are well known to those of skill in the art and are exemplified below. It should be readily understood that by inhibiting and reducing viral replication and proliferation, viral infectivity also is inhibited and reduced and the cells are suitably treated for HCMV or HSV-1 infection.

For the purposes of this invention, a "cell" is intended to include, but not be limited to a mammalian cell, e.g., a mouse cell, a rat cell, a woodchuck cell, a simian cell, or a human cell. Viruses which are effectively treated by the compounds, compositions and methods of this invention include DNA and RNA viruses, particularly herpes viruses. Examples of herpes viruses, or herpesviridae, are herpes simplex virus 1 (HSV-1), herpes simplex virus 2 (HSV-2), varicella-zoster virus (VZV), Epstein-Barr virus (EBV), human cytomegalovirus (HCMV), human herpes virus 6 (HHV-6), human herpes virus 7 (HHV-7), and human herpes virus 8 (HHV-8). The compounds of the present invention are particularly useful in the treatment of HCMV and HSV-1 infections.

Effective amounts are easily determined by those of skill in the art and will vary with the cell, virus being effected and the purpose of the treatment. For example, when utilizing the drug in cell culture, it is important that the amount of drug not be cytotoxic to the cells.

"Suitable conditions" include in vitro, ex vivo or in vivo. When the method is practiced in vitro, contacting may be effected by incubating the cells with an effective antiviral amount of the compound, effective to inhibit viral reproduction and proliferation in the cell or culture of cells. The compound can be added directly to the culture media or combined with a carrier prior to addition to the cells. In vitro, the method is particularly useful for inhibiting viral reproduction, proliferation and therefore infection in laboratory cell cultures. Ex vivo, the compounds are useful to inhibit viral reproduction and proliferation in blood and plasma prior to reintroduction into a patient.

The use of the compounds and methods in vitro also provides a powerful bioassay to screen for novel drugs or compounds which provide similar or enhanced antiviral activity. Using the methods set forth below, the drug to be tested is assayed under the same conditions as a compound of this invention. Antiviral and cytotoxicity of the test drug can then be compared to a compound of this inventive group.

Although the compounds are shown below to be particularly effective against HCMV and HSV-1, one of skill in the art can easily determine other viruses effectively treated with the compounds of this invention by use of methods described herein and others well known to those of skill in the art. Other viruses contemplated to be treated within the scope of the present invention include, but are not limited to: human immunodeficiency virus (HIV) and hepatitis viruses.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

The compositions also can be administered to subjects or individuals susceptible to or at risk of a viral infection, such as HCMV or HSV-1 infection. Thus, this invention also provides a prophylactic method of inhibiting viral replication, proliferation and/or viral infection in a subject by administering to a subject a prophylactically effective amount of the compound or composition under suitable conditions such that viral replication, proliferation or infection is inhibited. A "prophylactically effective amount" is an amount which inhibits viral infection, reproduction and proliferation in a subject challenged with the virus without toxicity to the cells and subject being treated.

It should be understood that by preventing or inhibiting viral proliferation, infection and replication in a subject or individual, the compositions and methods of this invention also provide methods for treating, preventing or ameliorating the symptoms or disorders associated with the viral infection, such as inclusion disease, blindness, mononucleosis, restenosis (HCMV); chickenpox, shingles (varicella-zoster virus); infectious mononucleosis, glandular, fever, and Burkittis lymphoma (Epstein-Barr virus); cold sores (herpes simplex virus 1); genital herpes (herpes simplex virus 2); roseola infantum (human herpes virus 6, human herpes virus 7); kaposi sarcoma (human herpes virus 8). Thus, this invention also provides methods of ameliorating, preventing, or treating disorders or symptoms associated with viral infection, e.g., HCMV or HSV-1 infection, e.g., restenosis, opportunistic infections (such as retinal infections, gastrointestinal infections, pneumonia, CNS infections) and in utero infections, by administering to the subject an effective amount of a compound of this invention under suitable conditions such that the disorder or symptom is ameliorated, prevented, or treated.

Administration in vivo can be effected in one dose, continuously or intermittently throughout the course of treatment. Methods of determining the most effective means and dosage of administration are well known to those of skill in the art and will vary with the composition used for therapy, the target virus, the purpose of the therapy, the target cell being treated, and the subject being treated. Single or multiple administrations can be carried out with the dose level and pattern being selected by the treating physician. Suitable dosage formulations and methods of administering the compounds can be found below.

The compounds of the present invention all exhibit antiviral activity against HCMV and HSV-1, many with acceptable cytotoxicity. It will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g. in immunocompromised patients, such as bone marrow and organ transplant patients as well as patients harboring HIV who are particularly susceptible to HCMV or HSV-1 infection.

The compounds and compositions of the present invention can be used in the manufacture of medicaments and in antiviral treatment of humans and other animals by administration in accordance with conventional procedures, such as an active ingredient in pharmaceutical compositions. The compounds of the invention can be provided as pharmaceutically acceptable formulations and/or "prodrugs," including but not limited to esters, especially carboxylic acid esters (preferably $C_1$ to $C_{20}$), such as 5'-acetyl and 2',3',5'-triacetyl prodrugs and pharmaceutical salts such as thiolate, citrate and acetate salts.

The pharmaceutical compositions can be administered topically, orally, intranasally, parenterally or by inhalation therapy, and may take the form of tablets, lozenges, granules, capsules, pills, ampoules, suppositories or aerosol form. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, the virus being treated and the nature of the infection.

In general, a suitable dose for each of the above-named viral infections, e.g., HCMV and HSV-1, is in the range of about 0.1 to about 250 mg per kilogram body weight of the recipient per day, preferably in the range of about 1 to about 100 mg per kilogram body weight per day and most preferably in the range of about 5 to about 20 mg per kilogram body weight per day. Unless otherwise indicated, all weights of active ingredient are calculated as the parent compound of the formula of the present invention for salts or esters thereof, the weights would be increased proportionally. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 2 $\mu$M to about 100 $\mu$M, preferably about 5 $\mu$M to about 70 $\mu$M, most preferably about 1 to about 50 $\mu$M. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient. The use of operative combinations is contemplated to provide therapeutic combinations requiring a lower total dosage of each component antiviral agent than may be required when each individual therapeutic compound or drug is used alone, thereby reducing adverse effects, e.g., cytotoxicity.

While it is possible for the active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Compounds of the formula of the present invention may also be presented for the use in the form of veterinary formulations, which may be prepared, for example, by methods that are conventional in the art.

C. General Chemical Procedures

Melting points were taken on a Thomas-Hoover Unimelt apparatus and are uncorrected. Nuclear magnetic resonance (NMR) spectra were obtained at 360 or 300 MHz with Bruker WP 360 SY or Bruker 300 SY. The chemical shift values are reported in parts per million (ppm) relative to tetramethylsilane as an internal standard. UV spectra were obtained with a Kontron Uvikon 860 UV/VIS spectrophotometer. IR spectra were obtained on a Nicolet 5DXB FT-IR spectrophotometer. Elemental analysis were performed by the Analytical Laboratory of the Chemistry Department, University of Michigan. Flash column chromatography was performed using silica gel 60 230–400 mesh (ICN) and using a well known technique described by Still et al. (1978) *J. Org. Chem.* Vol. 43:2923–2925 and incorporated herein by reference. Thin layer chromatography (TLC) was performed on pre-scored Silica gel GHLF plates (Analtech, Newark, Del., USA). Compounds were visualized by illumination under UV light (254 nm) or by spraying with 20% methanolic sulfuric acid followed by charring on a hot plate. Evaporations were carried out under reduced pressure (water aspirator) with water bath temperatures below 40° C. unless otherwise specified. All solvents were dried prior to use as described by the handbook Purification of Laboratory Chemicals (Perrin, D. D.; Arnarego, W. L. F., Purification of Laboratory Chemicals, 3rd Ed., Pergamon Press, N.Y. 1988, incorporated herein by reference) and stored over 4 Angstrom sieves, under argon. Materials obtained from commercial suppliers were used without purification unless otherwise noted.

D. Preparation of the Halogenated Pyridine Precursors

Several synthetic methods for the preparation of halogenated pyridine compounds have been described. For example, in one method, picolinic acid hydrochloride is first reacted with $SOCl_2$ and subsequently with $H_2O$ to yield 4-chloro-picolinic acid, which is further converted to 2-amino-4-chloro-pyridine. See, for example, R. Graf, Ber. 1931, Vol. 64, pp. 21–27; J. Lombardino, *J. Med Chem.*, 1961, Vol. 24, pp. 39–42; H. S. Mosher et al., *J. Org. Chem.*, 1954, Vol. 20, pp. 283–286; and E. Malsumura et al., *Bull. Chem. Soc. Jpn.*, 1970, Vol. 43, pp. 3210–3214. In another method, picolinic acid hydrochloride is first reacted with $SOCl_2$ and SO2 gas, and subsequently with methanol to yield methyl 4-chloro-picolinate, which is further converted to 2-amino-4-chloro-pyridine. See, for example, Mosher et al., 1964. In yet another method, a 4-nitro-pyridine compound is reacted with $(CH_3)_2SO_4$ to yield 2-cyano-4-nitro-pyridine, which is subsequently reacted with sulfuric acid and sodium nitrite to yield 4-nitro-picolinic acid, which upon reaction with HCl yields 4-chloro-picolinc acid. See, for example, Matsumura et al., 1970.

The synthetic strategy used in the preparation of compounds 2 and 3 is illustrated in FIG. 1. In this method, picolinic acid hydrochloride (also known as 2-(carboxylic acid)-pyridine hydrochloride) (compound 1), was reacted with thionyl chloride (i.e., $SOCl_2$) and water (i.e., $H_2O$) and refluxed for 4 days, followed by reaction with methanol (i.e., $CH_3OH$) to yield the hydrochloride (i.e., HCl) salt of the methyl ester, 2-(methylcarboxylate)-4-chloro-pyridine, to yield methyl ester (also known as methyl 4-chloro-picolinate hydrochloride) (compound 2) in 80–90% yield. This product was then reacted with hydrazine (i.e., $NH_2NH_2$), sodium nitrite (i.e., $NaNO_2$), and acetic acid (i.e., $CH_3COOH$) in water and heated to yield the desired 2-amino-4-chloro-pyridine (compound 3) in about 60% yield and a trace amount of dipyridine by-product.

Compound 2

Methyl 4-chloropicolinate hydrochloride (2). $H_2O$ (18 mL) was added dropwise to a stirred suspension of picolinic acid hydrochloride, compound 1 (157.9 g, 1.0 mol) in thionyl chloride (400 mL). The resulting mixture was heated under reflux for 4 days giving a clear orange solution. After cooling to ambient temperature, the solution was concentrated to a syrup and the residue coevaporated with toluene (2×500 mL). The residue was dissolved in toluene (1 L) and cooled to 0–5° C. Methanol (44.0 g, 1.0 mol) was added dropwise to the ice cold reaction mixture giving a heavy white precipitate. This precipitate was collected by filtration, washed with toluene (3×100 mL) and dried at 40° C. for 24 hr to give 176.5 g (85%) of compound 2 as a white crystalline solid.

Compound 2: mp 131–132° C. (dec); $^1$H-NMR (360 MHz, $CDCl_3$): δ8.67 (q, 1H), 8.04 (q, 1H), 7.81 (q, 1H), 3.86 (s, 3H). Anal. Calcd for $C_7H_7Cl_2NO_2 \cdot HCl \cdot ¼ H_2O$: C, 39.56; H, 3.56; N, 6.59. Found: C, 39.73; H, 3.36; N, 6.54.

Compound 3

2-Amino4-chloropyridine (3). Compound 2 (100 g, 0.48 mol) in methanol (500 mL) was treated with hydrazine hydrate (210 mL) giving a precipitate. The suspension was stirred for 2 hours and the precipitated hydrazide was collected by filtration. The hydrazide was dissolved in 1N HCl (450 mL) and the solution was cooled to 0–5° C. A solution of sodium nitrite (37.2 g, 0.54 mol) in water (150 mL) was added dropwise to the cold solution, resulting in a heavy precipitation. After stirring for 15 min the precipitate was collected by filtration and washed with water. The moist precipitate was added to a 1:1 (v/v) mixture of acetic acid and water (800 mL) and the solution heated on a steam bath until gas evolution ceased. The reaction mixture was cooled to room temperature, the pH adjusted to 7 with ammonium hydroxide and the resulting precipitate collected by filtration. Recrystallization from EtOH gave 37 g (60%) of compound 3 as a white crystalline solid.

Compound 3: mp 129–131° C.; $R_f$ 0.4 (EtOAc/hexane 1:2); $^1$H-NMR (360 MHz, DMSO-$d_6$):δ7.85 (d, 1H, J=5.5 Hz), 6.53 (q, 1H, J=5.5 Hz and J=1.9 Hz), 6.48 (d, 1H, J=1.9 Hz), 6.26 (broad s, 2H $D_2O$ exchangeable). $^{13}$C-NMR ($d_6$-DMSO, 90.6 MHz): δ160.858; 149.277, 142.794, 111.696; 106.844.

Figure 2:
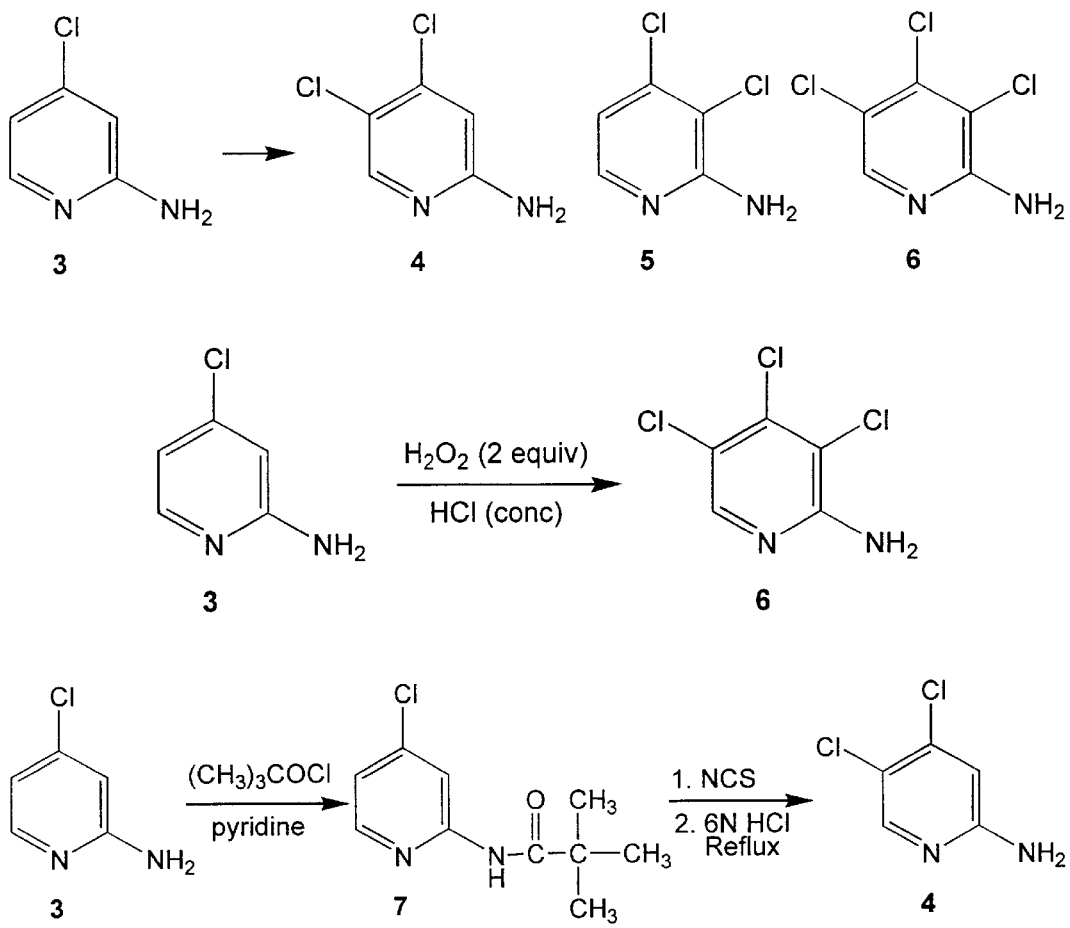
FIG. 2 is a flowchart illustrating methods for the chemical synthesis 2-amino-4,5-dichloro-pyridine; 2-amino-3,4-dichloro-pyridine; and 2-amino-3,4,5-trichloro-pyridine.

The synthetic strategy used in the preparation of compounds 4, 5, 6, 7, and 8 is illustrated in FIG. 2. Polychlorinated pyridines were synthesized from the 2-amino-4-chloro-pyridine (compound 3). For example, compound 3 was dissolved in concentrated hydrochloric acid (HCl), reacted at 0° C. with hydrogen peroxide ($H_2O_2$), and allowed to warm to room temperature yielding a mixture of 2-amnino-4,5-dichloro-pyridine (compound 4), 2-amino-3,4-dichloro-pyridine (compound 5), and 2-amino-3,4,5-trichloro-pyridine (compound 6). In another method, compound 3 was dissolved in concentrated hydrochloric acid (HCl) and heated at reflux temperature to yield 2-amino-4,5-dichloro-pyridine (compound 4) in 97% yield. In another method, compound 3 was dissolved in concentrated hydrochloric acid (HCl), reacted at 0° C. with hydrogen peroxide ($H_2O_2$), and allowed to warm to room temperature yielding 2-amino-3,4,5-dichloro-pyridine (compound 6) in 80% yield. In still another method, compound 3 was reacted with trimethylacetyl chloride (($CH_3)_3COCl$) to yield 2-trimethylacetamido-4-chloro-pyridine (compound 7). Compound 7 was then reacted with N-chlorosuccinimide (NCS) to yield 2-trimethylacetamido-4,5-chloro-pyridine (compound 8). Compound 8 was then reacted with hydrochloric acid (HCl) to yield 2-amino-4,5-chloro-pyridine (compound 4).

Compounds 4, 5, and 6

2-Amino-4,5-dichloropyridine (4), 2-amino-3,4-dichloropyridine (5), and 2-amino-3,4,5-trichloropyridine (6). 2-Amino-4-chloropyridine, compound 3 (15.0 g, 0.117 mol) was dissolved in concentrated HCl (60 mL). The solution was cooled to 0° C.in an ice bath and $H_2O_2$ (11.9 mL, 0.117 mol of 32% $H_2O_2$ in water) was added. The resulting mixture was allowed to warm to room temperature and stirred at room temperature for 2 hr. The reaction mixture was poured into 200 mL of water, made basic to litmus (pH 7) by the addition of solid $Na_2CO_3$ and extracted with EtOAc (3×100 mL). The combined organic extracts were dried over magnesium sulfate, filtered and concentrated to give a yellow solid. This solid contained three products, as determined by TLC, which were separated by chromatography (EtOAc/hexane 1:2, 10 cm×20 cm). Fractions containing each individual product as determined by TLC mobility were combined, evaporated to dryness and recrystallized from ethanol to afford 8.17 g (43%) of 4 as white crystals. 6.8 g (38%) of 5 as white crystals and 2.3 g (10%) of 6 as a white solid.

Compound 4: mp 140–141° C.; $R_f$ 0.28 (EtOAc/hexane 1:2); $^1$H-NMR (300 MHz, CDCl$_3$) δ8.06 (s, 1H), 6.61 (s, 1H), 4.58 (broad s, 2H, D$_2$O exchangeable); $^1$H-NMR (360 MHz, DMSO-d$_6$): δ8.03 (s, 1H), 6.65 (s, 1H), 6.43 (broad s, 2H, D$_2$O exchangeable). Anal. Calcd for $C_5H_4Cl_2N_2$: C, 36.83; H, 2.47; N, 17.19. Found: C, 37.20; H, 2.54; N, 17.16.

Compound 5: mp 99–100° C.; $R_f$ 0.33 (EtOAc/hexane 1:2); $^1$H-NMR (360 MHz, DMSO-d$_6$) δ7.84 (d, 1H, J=5.3 Hz), 6.77 (d, 1H, J=5.3 Hz), 6.65 (broad s, 2H, D$_2$O exchangeable).

Compound 6: mp 160–161° C.; $R_f$ 0.48 (EtOAc/hexane 1:2); $^1$H-NMR (360 MHz, DMSO-d$_6$) δ8.08 (s, 1H), 6.85 (broad s, 2H D$_2$O exchangeable).

Compound 6

2-Amino-3,4,5-trichloropyridine (6). 2-Amino-4-chloropyridine, compound 3 (5.0 g, 0.04 mol) was dissolved in conc HCl (20 mL) and the solution cooled to 0° C. in an ice bath. $H_2O_2$ (8.1 mL, 0.08 mol of 32% $H_2O_2$ in water) was added to the solution and the reaction mixture was allowed to warm to room temperature and stirred for 4 hr. The reaction mixture was then poured into 100 mL of water, made basic to litmus (pH 8) by the addition of solid $Na_2CO_3$ and extracted with EtOAc (3×50 mL). The combined organic phase was dried over magnesium sulfate, filtered and the filtrate concentrated to give a yellow solid. This solid was recrystallized from ethanol to give 6.3 g (80%) of 6 as a white solid (mp 160–162° C.).

4-Chloro-2-(trimethylacetamido)pyridine (7). Trimethylacetyl chloride (39.2 mL, 0.32 mol) was added dropwise to a solution of compound 3 (27.3 g, 0.21 mol) in pyridine (100 mL). The resulting mixture was stirred overnight at ambient temperature. Water (200 mL) was added and the aqueous mixture was extracted with EtOAc (3×100 mL). The combined EtOAc extracts were dried over magnesium sulfate, filtered, and concentrated under reduced pressure to a solid which was crystallized from EtOH to give 43.2 g (95%) of compound 7 as a white solid.

Compound 7: mp 86–87° C.; $R_f$ 0.70 (EtOAc/hexane 2:1); $^1$H-NMR (360 MHz, CDCl$_3$) δ8.36 (q, 1H), 8.15 (q, 1H), 8.06 (broad s, 1H, D$_2$O exchangeable), 7.04 (q, 1H), 1.32 (s, 0.9H). Anal. Calcd for $C_{10}H_{13}ClN_2O$: C, 55.43; H, 6.05; N, 12.93. Found: C, 55.88; H, 5.84; N, 13.05.

Compound 8

4,5-Dichloro-2-(trimethylacetamido)pyridine (8). N-chloro-succinimide (NCS, 79.45 g, 0.6 mol) was added to a solution of compound 7 (25.8 g, 0.12 mol) in dry CH$_3$CN (300 mL). The resulting suspension was heated at reflux for 2 hours and then cooled to room temperature. After washing with 10% aqueous NaOH (2×150 mL), then water (2×200 mL), the organic phase was dried over magnesium sulfate, filtered, and concentrated under reduced pressure to give a solid. This solid was recrystallized from EtOH to give 28.7 g (95%) of compound 8 as a white solid.

Compound 8: mp 105–106° C.; $R_f$ 0.75 (EtOAc/hexane 2:1); $^1$H-NMR (360 MHz CDCl$_3$) δ8.49 (s, 1H), 8.26 (s, 1H), 8.02 (broad s, 1H D$_2$O exchangeable), 1.33 (s, 9H). Anal. Calcd for $C_{10}H_{12}Cl_2N_2O$: C, 48.60; H 4.89; N, 11.34. Found: C, 48.48; H, 4.72; N, 10.96.

Compound 4

2-Amino-4,5-dichloropyridine (4). Compound 8 (10 g, 0.04 mol) in 6 N HCl (50 mL) was heated at reflux for 10 h. This solution was neutralized with $Na_2CO_3$ (to pH 7 by litmus) and then extracted with EtOAc (3×150 mL). The combined EtOAc extracts were dried over magnesium sulfate, filtered and concentrated to give a solid residue, which, after recrystallization from EtOH, gave 6.3 g (97%) of compound 4 as a white solid (mp 140–141° C.).

E. Preparation of the Imidazo[1,2-a]Pyridines

One method for the synthesis of imidazo[1,2-a]pyridines involves the reaction of 2-amino-5-chloro-pyridine with ethyl haloacetate (e.g., ClCH$_2$C(=O)OC$_2$H$_5$) which, upon ring closure, yields the imidazo[1,2-a]pyridine bicyclic ring structure. See, for example, Yasuo et al., 1987.

In this disclosure, polychloro-imidazo[1,2-a]pyridines were synthesized by reacting the appropriate chloropyridine with ethyl bromoacetate (BrCH$_2$C(=O)OC$_2$H$_5$) followed by treatment with an ion-exchange resin (Cl-form) to yield the hydrochloride salt, which was subsequently treated with POCl$_3$ to yield the desired imidazo[1,2-a]pyridine.

Figure 3:
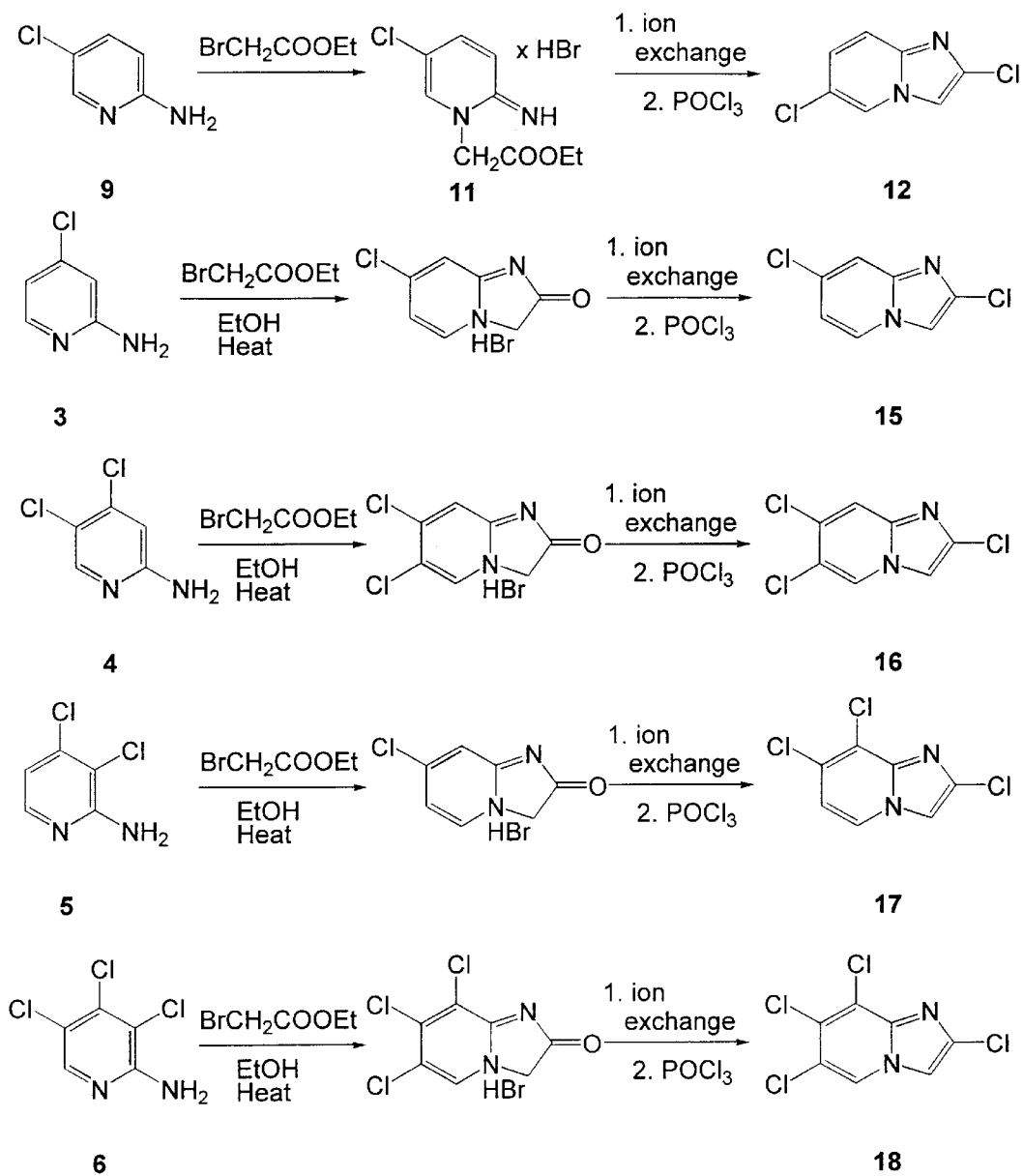
FIG. 3 is a flowchart illustrating methods for the chemical synthesis of various polychloro-imidazo[1,2-a]pyridines.

The synthetic strategy used in the preparation of compounds 11, 12, 15, 16, 17, and 18 is illustrated in FIG. 3.

Compound 11

Ethyl 2-imino-5-chloro-1,2-dihydropyridin-1-yl-acetate hydrobromide (11). To 2-amino-5-chloropyridine, compound 9 (Aldrich, 10 g, 0.078 mol) was added ethyl bromoacetate (30 mL, 0.269 mol) and the reaction mixture stirred at room temperature for 8 hours. The heavy white precipitate was removed by filtration and recrystallized from EtOH to yield 21.9 g (95%) yield of compound 11 as white crystals.

Compound 11: mp>300° C. (decomposes); $R_f$ 0.23 (EtOAc/EtOH/Acetone/H$_2$O 20:2:2:1); $^1$H-NMR (360 MHz, DMSO-d$_6$) δ9.0 (s, 2H, D$_2$O exchangeable), 8.44 (d, 1H, J=2.2 Hz), 8.04 (dd, 1H, J=2.2 Hz, J=9.6 Hz), 7.25 (d, 1H, J=9.6 Hz), 5.17 (s, 2H), 4.19 (q, 2H), 1.24 (t, 3H); $^{13}$C-NMR (90 MHz, DMSO-d$_6$) δ165.54, 153.76, 143.00, 138.00, 117.67, 116.45, 62.11, 53.96, 13.96. Anal. Calcd. for $C_9H_{12}BrClN_2O_2$: C, 36.57; H, 4.08; N, 9.48. Found: C, 36.49; H, 4.05; N, 9.36.

Compound 12

2,6-Dichloro-imidazo[1,2-a]pyridine (12). The imino-derivative compound 11 (10 g, 0.03 mol) was dissolved in water (100 mL) and treated with IRA-47 (Cl-form) ion exchange resin (60 g) for 30 min. The resin was removed by filtration and the filtrate treated again with resin (60 g) for 30 min, resin removed by filtration and the aqueous filtrate evaporated to dryness. The resulting solid was dissolved in ethanol (100 mL) and evaporated to dryness to give the HCl salt as a reddish brown foam. The HCl salt was treated with POCl$_3$ (30 mL, 0.27 mol) and the resulting mixture heated at reflux, under CaSO$_4$ drying tube, for 2 h. The reaction mixture was cooled to room temperature and excess POCl$_3$ removed under reduced pressure to give a dark syrup. Ice water was added to this syrup and NH$_4$OH was added to the resulting solution until it remained basic to litmus (pH 8). The suspension was extracted with CHCl$_3$ (80 mL×3), the organic phase dried over magnesium sulfate, filtered and the filtrate evaporated to dryness to give a white solid. This solid was purified by flash chromatography (EtOAc/hexane 1:2, 15 cm×5 cm), the fractions containing product were pooled, solvent removed under reduced pressure and the solid was crystallized from MeOH to give 3.4 g (60%) of compound 12.

Compound 12: mp 155–156° C.; R$_f$ 0.45 (EtOAc/hexane 1:2); $^1$H-NMR (360 MHz, CDCl$_3$) δ8.15 (s, 1H), 7.19 (d, 2H), 7.48 (d, 1H), 7.50 (d, 1H); $^1$H-NMR (360 MHz DMSO-d$_6$) δ8.78 (d, 1H, J=2.0 Hz), 8.00 (s, 1H), 7.57 (d, 1H J=9.6 Hz), 7.37 (dd, 1H, J=9.6 Hz, J=2.0 Hz); $^{13}$C-NMR (90 MHz, DMSO-d$_6$) δ141.47 (C8a), 134.54 (C2), 126.53 (C7), 124.60 (C5), 119.78 (C6), 116.87 (C8), 109.77 (C3); UV λ$_{ax}$ (EtOH) 288 (4351), 230 (7965); (pH11) 275 (14016), 230 (33863); (pH 1) 281 (9265), 221 (26718).

Compound 15

2,7-Dichloro-imidazo[1,2-a] pyridine (15). 2-Amino-4-chloropyridine, compound 3 (3.9 g, 0.03 mol) was added to ethyl bromoacetate (30 mL, 0.27 mol) and the solution was stirred at room temperature for 8 hours. The resulting precipitate was removed from the reaction mixture by filtration and dissolved in water (100 mL). The solution was treated with IRA-47 (Cl-form) ion exchange resin (60 g) for 30 min. The resin was removed by filtration and the filtrate treated again with resin (60 g) for 30 min, resin removed by filtration and the aqueous filtrate evaporated to dryness. The resulting solid was dissolved in ethanol (100 mL) and evaporated to dryness to give the HCl salt as a reddish brown foam. The HCl salt was treated with POCl$_3$, (30 mL, 0.27 mol) and the resulting mixture heated at reflux, under CaSO$_4$ drying tube, for 2 h. The reaction mixture was cooled to room temperature and subsequently excess POCl$_3$ was removed under reduced pressure to give a dark syrup. This syrup was treated with ice water and NH$_4$OH was added until the solution remained basic to litmus (pH 8). The suspension was extracted with CHCl$_3$ (80 mL×3), the organic phase dried over magnesium sulfate, filtered and filtrate evaporated to dryness to give a white solid. This solid was purified by flash chromatography (EtOAc/hexane 1:2, 15 cm×5 cm). The fractions containing product were pooled, the solvent was removed under reduced pressure and the solid was crystallized from MeOH to give 2.8 g (50%) of compound 15.

Compound 15: mp 153–154° C.; R$_f$ 0.45 (EtOAc/hexane 1:2); $^1$H-NMR (360 MHz, CDCl$_3$) δ7.97 (dd, 1H, J=0.8 Hz, J=7.2 Hz), 7.52 (dd, 1H, J=0.8 Hz, J=2.1 Hz), 7.49 (s, 1H), 6.83 (dd, 1H, J=7.2 Hz, J=2.1 Hz) $^{13}$C-NMR (90 MHz, DMSO-d$_6$) δ142.781 (C8a), 134.54 (C2), 130.84 (C7), 127.65 (C5), 114.89 and 114.08 (C8 and C6), 109.58 (C3); UV λ$_{ax}$ (EtOH) 306 (4421), 284 (5080), 231 (13182); (pH 11) 283 (5702), 229 (22170); (pH 1) 281 (10914) 221 (22532). Anal. Calcd. for C$_7$H$_4$Cl$_2$N$_2$: C, 44.95; H 2.16; N, 14.98. Found: C, 44.74; H 2.36; N, 14.95.

Compound 16

2,6,7-Trichloro-imidazo[1,2-a]pyridine (16). 2-Amino-4,5-dichloropyridine, compound 4 (3.3 g, 0.02 mol) was treated with neat ethyl bromoacetate (20.0 mL, 0.18 mol) at 60° C. for 24 hours. The precipitate that formed was isolated by filtration, dissolved in water (150 mL) and treated with IRA-47 (Cl-form) ion exchange resin (2×100 g). After the resin had been removed by filtration, the aqueous filtrate was evaporated to dryness to give a HCl salt as a reddish foam. The HCl salt was treated with POCl$_3$ (30 mL, 0.27 mol) as described above to give, after flash chromatography (EtOAc/hexane 1:2, 15 cm×5 cm) and recrystallization from EtOH, 1.8 g (40%) of 16 as white crystals.

Compound 16: mp 180–181° C.; R$_f$ 0.47 (EtOAc/hexane 1:2); $^1$H-NMR (360 MHz, CDCl$_3$) δ8.26 (s, 1H), 7.68 (s, 1H), 7.49 (s, 1H); $^1$H-NMR (360 MHz, DMSO-d$_6$) δ8.99 (s, 1H), 8.02 (s, 1H), 8.00 (s, 1H); $^{13}$C-NMR (90 MHz, CDCl$_3$) δ142.51 (C8a), 137.72 (C2), 131.22 (C7), 124.03 (C5), 121.07 (C6), 117.08 (C8), 108.75 (C3); $^{13}$C-NMR (90 MHz, DMSO-d$_6$) δ141.60 (C8a), 135.27 (C2), 129.33 (C7), 126.13 (C5), 118.52 (C6), 116.14 (C8), 109.86 (C3); UV λ$_{ax}$ (EtOH) 315 (4237), 294 (4118), 234 (13496); (PH11) 292 (4542), 233 (23989); (pH 1) 293 (7576), 226 (24237); HRMS m/z calcd for C$_7$H$_3$Cl$_3$N$_2$ 219.9362, found 219.9360. Anal. Calcd for C$_7$H$_3$Cl$_3$N$_2$: C, 37.96; H, 1.37; N, 12.65. Found: C, 37.81; H 1.39; N, 12.55.

Compound 17

2,7,8-Trichloro-imidazo[1,2-a]pyridine (17). 2-Amino-3,4-dichloropyridine, compound 5 (1.0 g, 6.1 mmol) was treated with ethyl bromoacetate (5.0 mL, 45.0 mmol) at 60° C. for 24 hours to give a white solid. This solid was removed by filtration, dissolved in water, treated with ion exchange resin and chlorinated with POCl$_3$ as described above to give, after purification by flash chromatography (EtOAc/hexane 1:2, 15 cm×4 cm) and recrystallization from MeOH, 700 mg (52%) of compound 17 as white crystals.

Compound 17: mp 220–221° C.; R$_f$ 0.29 (EtOAc/hexane 1:2); $^1$H-NMR (360 MHz, CDCl$_3$) δ7.93 (d, 1H J=7.15 Hz), 7.56 (s, 1H), 6.94 (d, 1H, J=7.15 Hz); $^{13}$C-NMR (90 MHz CDCl$_3$) δ141.77 (C8a), 137.20 (C2), 129.87 (C7), 123.52 (C5), 121.30 (C8), 115.08 (C6), 110.39 (C3); UV λ$_{ax}$ (EtOH) 304 (5250), 288 (5825), 233 (10434); (pH 11) 287 (6566), 232 (24612); (pH 1) 287 (8865), 231 (26610); HRMS m/z calcd for C$_7$H$_3$Cl$_3$N$_2$ 219.9362, found 219.9355. Anal. Calcd for C$_7$H$_3$Cl$_3$N$_2$.¼ H$_2$O: C, 37.21; H, 1.56; N, 12.40. Found: C, 37.40; H, 1.46; N, 12.22.

Compound 18

2,6,7,8-Tetrachloro-imidazo[1,2-a]pyridine (18). 2-Amino-3,4,5-trichloropyridine, compound 6 (1 g, 5.1 mmol) was treated with neat ethyl bromoacetate (5.0 mL, 45.0 mmol) at 80° C. for 24 hours. The resulting black solution was applied to a silica gel pad (50 g) and washed with EtOAc/hexane 1:2 (500 mL) to remove the excess ethyl bromoacetate. Subsequently washing the silica gel with MeOH (200 mL) eluted a highly fluorescent compound. Removal of the MeOH under reduced pressure gave a black tarry residue, which was dissolved in water and treated with IRA-47 (Cl-form) ion exchange resin (40 g) for 30 min. The resin was removed by filtration and the filtrate treated again with resin (40 g) for 30 min, resin removed by filtration and the aqueous filtrate evaporated to dryness. The resulting solid was dissolved in ethanol (100 mL) and evaporated to dryness to give the HCl salt as a black residue. This residue was treated with $POCl_3$ (20 mL, 0.18 mol) and the resulting mixture heated at reflux, under $CaSO_4$ drying tube, for 2 h. The reaction mixture was cooled to room temperature and excess $POCl_3$ removed under reduced pressure to give a dark, syrup. This syrup was treated with ice water and neutralized with $NH_4OH$ until it remained basic to litmus (pH 8). The resulting solution was extracted with $CHCl_3$ (50 mL×3), the organic phase dried over magnesium sulfate, filtered and the filtrate evaporated to dryness to give a dark solid. This solid was purified by flash chromatography (EtOAc/hexane 1:2, 15 cm×2 cm), the fractions containing product were pooled, solvent removed under reduced pressure and the solid was crystallized successively from EtOH and MeOH to give 200 mg (16%) of compound 18 as a white solid.

Compound 18: mp 232–233° C.; $R_f$ 0.58 (EtOAc/hexane 1:2); $_1$H-NMR (300 MHz, $CDCl_3$) $\delta$8.20 (s, 1H), 7.55 (s, 1H); $^{13}$C-NMR (90 MHz, DMSO-$d_6$) $\delta$139.45 (C8a), 135.32 (C2), 127.97 (C7), 124.85 (C5), 124.34 (C8), 118.46 (C6), 111.74 (C3); UV $\lambda_{max}$ (EtOH) 298 (5592), 235 (15388); (pH11) 297 (6100), 232 (27300); (pH 1) 296 (6560), 228 (29120); HRMS m/z calcd for $C_7H_2Cl_4N_2$ 253.8972, found 253.8967. Anal. Calcd for $C_7H_2Cl_4N_2\cdot\frac{3}{4}$ $H_2O$: C, 31.2; H, 1.20; N, 10.40. Found: C, 31.0; H, 0.89; N, 10.0.

F. Preparation of the Imidazo[1,2-a]Pyridines C3-Nucleosides

Imidazo[1,2-a]pyridines C3-nucleosides may be prepared from imidazo[1,2-a]pyridines by first iodinating at the 3-position followed by palladium cross-catalyzed coupling to attach the sugar-like moiety.

Figure 4:
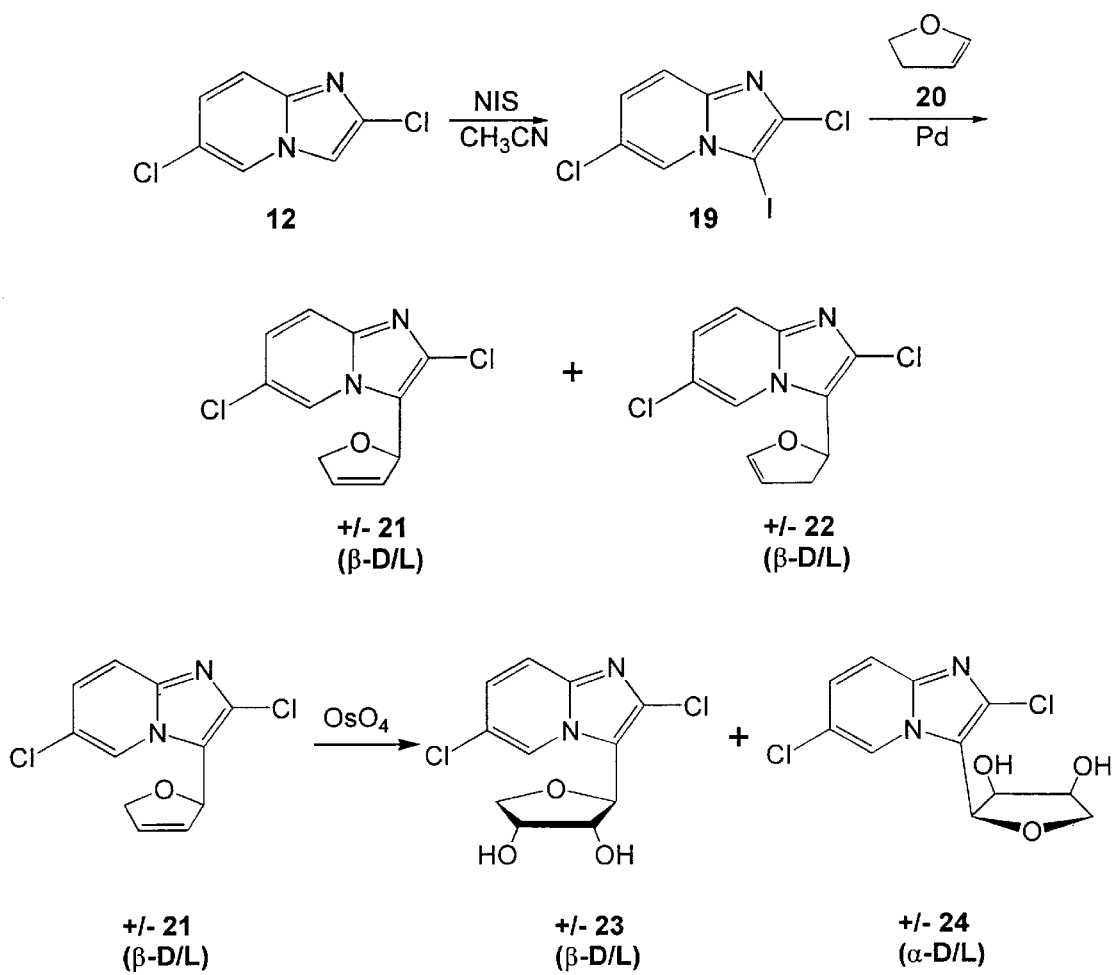
FIG. 4 is a flowchart illustrating methods for the chemical synthesis of various 2,6-dichloro-imidazo[1,2-a]pyridine C3-nucleosides.

The synthetic strategy used in the preparation of compounds 19, 21,22, 23, and 24 is illustrated in FIG. 4. 2,6-dichloro-imidazo[1,2-a]pyridine (compound 12) was reacted with NIS (an iodinating agent) in acetonitrile (i.e., $CH_3CN$) to form 3-iodo-2,6,7-trichloro-imidazo[1,2-a] pyridine (compound 19). The iodinated compound was subsequently reacted with 2,3-dihydroftiran (compound 20) and palladium to yield two isomeric 3-substituted compounds (compounds 21 and 22). By using different ligands, solvents, and temperatures, a range of relative yields of compounds 21 and 22 were obtained, as shown below in Table 1.

TABLE 1

Palladium Coupling Conditions

| # | Base | Lignad | Solvent | Temp (° C.) | % 21 | % 22 |
|---|------|--------|---------|-------------|------|------|
| 1 | $Et_3N$ | $Ph_3P$ | $CH_3CN$ | 25 | 10 | 11 |
| 2 | $Et_3N$ | $Ph_3P$ | DMF | 25 | 20 | 10 |
| 3 | $Et_3N$ | $Ph_3As$ | $CH_3CN$ | 25 | 20 | 25 |
| 4 | $Et_3N$ | $Ph_3As$ | $CH_3CN$ | 60 | 15 | 30 |
| 5 | $Et_3N$ | $P(o\text{-}tol)_3$ | DMF | 25 | 30 | 15 |
| 6 | $Et_3N$ | $Ph_3As$ | DMF | 25 | 55 | 35 |
| 7 | $Et_3N$ | $Ph_3As$ | DMF | 25 | 55 | 35 |
| 8 | $Et_3N$ | $Ph_3As$ | DMF | 60 | 60 | 25 |
| 9 | $Et_3N$ | $Ph_3As$ | DMF | 45 | 81 | 0 |

Compound 19

2,6-Dichloro-3-iodo-imidazo[1,2-a]pyridine (19). To a suspension of 2,6-dichloro-imidazo[1,2-a]pyridine, compound 12 (4.0 g, 0.02 mol) in dry $CH_3CN$ (50 mL) was added N-iodosuccinimide (NIS, 5.3 g, 0.024 mol) and the mixture stirred at room temperature for 1 h. The reaction mixture was heated at reflux for 10 min and then cooled to room temperature. Chloroform (200 mL) was added to the reaction mixture and the organic phase washed successively with 10% NaOH (100 mL), sodium thiosulfate (100 mL) and water (2×100 mL) then dried over magnesium sulfate, filtered and concentrated to dryness under reduced pressure. The resulting solid was suspended in MeOH and filtered to give 5.0 g (80%) of compound 19 as white crystalline solid.

Compound 19: mp 234–235° C.; $R_f$ 0.43 (EtOAc/hexane 1:5); 1H-NMR (360 MHz, DMSO-$d_6$): $\delta$8.44 (dd, 1H J =0.8 Hz, J=2.0 Hz), 7.63 (dd, 1H, J=0.8 Hz, J=9.5 Hz), 7.45 (dd, 1H, $J_7$=9.5 Hz, J=2.0 Hz). $^{13}$C-NMR (90 MHz, DMSO-$d_6$): $\delta$144.39, 141.02, 127.45, 125.17, 121.33, 117.39, 66.49. Anal. Calcd for $C_7H_3Cl_2IN_2$: C, 26.87; H, 0.97; N, 8.95. Found: C, 26.50; H 1.10; N, 8.64.

Compound 21 and 22

2,6-Dichloro-3-(2',3'-dideoxy-2',3'-didehydro-β-D/L-erythro-furanosyl)-imidazo[1,2-a]pyridine (+/−21a)

2,6-dichloro-(2',3'-dideoxy-3',4'-didehydro-β-D/L-erythro-furanosyl)-imidazo[1,2-a]pyridine (+/−22a)

Procedure A: $Pd(OAc)_2$ (85 mg, 0.38 mmol) and $Ph_3As$ (0.24 g, 0.77 mmol) were placed in a flame dried flask under argon. Dry DMF (7 mL) was added and the solution stirred at room temperature for 1h. 2,6-Dichloro-3-iodoimidazo[1, 2-a]pyridine, compound 19 (0.5 g, 1.6 mmol) was then added to the reaction mixture, followed by the addition of $Et_3N$ (1 mL, 6.4 mmol) and 2,3-dihydrofuran, compound 20 (0.6 mL, 8 mmol). The reaction mixture was stirred under argon overnight, then EtOAc (30 mL) was added and the resulting slurry filtered through $SiO_2$ (30 g). The silica pad was washed with EtOAc (100 mL) and the organic phase was concentrated to dryness. The resulting solid was purified by flash column chromatography (EtOAc/hexane 1:5, 15 cm×2 cm). The fractions containing each product were pooled, concentrated to dryness under reduced pressure and crystallized from $H_2O$/MeOH mixture to give 219 mg (55%) of compounds +/−21 as a white crystalline solid and 140 mg (35%) of +/−22 as a white crystalline solid.

Procedure B: Same as procedure A except that 2 eq of $Ag_2CO_3$ are added to the reaction mixture at the same time as the heterocycle, compound 19. Following the addition of $Et_3N$ and dihydrofuran, compound 20, the reaction mixture was heated at 45° C. for 48 hours. The reaction mixture is worked up as described for procedure A to give after recrystallization 80% yield of +/−21a.

Compound +/−21: mp 95–96° C.; $R_f$ 0.21 (EtOAc/hexane 1:5); $^1$H-NMR (300 MHz, $CDCl_3$): $\delta$7.99 (dd, 1H, J=0.8 Hz, J=1.5 Hz), 7.46 (dd, 1H, J=0.8 Hz, J=9.5 Hz, 7.19 (dd, 1H, J=1.5 Hz, J=9.5 Hz), 6.29 (m, 2H), 5.92 (m, 1H), 4.90 (m, 2H). $^1$H-NMR (360 MHz, DMSO-$d_6$): $\delta$8.34 (d, 1H, J=1.9 Hz), 7.65 (d, 1H J=9.5 Hz), 7.46 (dd, 1H, J=1.9 Hz, J=9.5 Hz), 6.40 (m, 1H), 6.28 (m, 1H), 6.07 (m, 1H), 4.86 (m, 1H), 4.70 (m, 1H). $_{13}$C-NMR (90 MHz, DMSO-$d_6$): $\delta$141.41; 134.06; 130.00; 126.82; 125.14; 122.61; 120.32; 117.78; 117.71; 77.27; 75.34. HRMS m/z calcd for $C_{11}H_8Cl_2N_2O$ 254.0013, found 254.0002. Anal. Calcd for $C_{11}H_8Cl_2N_2O$: C, 51.79; H, 3.16; N, 10.98. Found: C, 51.92; H, 3.16; N, 10.86.

Compound +/−22: mp 109–110° C.; $R_f$ 0.29 (EtOAc/hexane 1:5); $^1$H-NMR (300 MHz, DMSO-$d_6$): 8.21 (d, 1H, J=1.9 Hz), 7.65 (d, 1H J=9.6 Hz), 7.45 (dd, 1H, J=9.6 Hz, J=1.9 Hz), 6.68 (d, 1H), 6.01 (dd, 1H, J=9.4 Hz, J=11.8 Hz), 5.26 (m, 1H), 2.95 (m, 2H). $^{13}$C-NMR (90 MHz, DMSO-d$_6$): 145.334; 141.338; 128.597; 126.648; 122.738; 120.388; 118.536; 117.425; 99.951; 71.876; 31.750. HRMS m/z calcd for $C_{11}H_8Cl_2N_2O$ 254.0013, found 254.0002. Anal. calcd for $C_{11}H_8Cl_2N_2O$: C, 51.79; H, 3.16; N, 10.98. Found: C, 51.80; H, 3.26; N, 10.98.

Compounds 23 and 24

2,6-Dichloro-3-(β-D/L-erythro-furanosyl)imidazo[1,2-a]pyridine (+/−23)

2,6-Dichloro-3-(α-D/L-erythro-furanosyl)imidazo[1,2-a]pyridine (+/−24)

Compound +/−21 (260 mg, 1 mmol) was added to an acetone (8 mL) and water (3 mL) mixture containing N-methylmorpholine N-oxide (158 mg, 1.4 mmol) and the mixture was stirred at room temperature for 12 hours. Sodium sulfite (1 g) was added and the mixture stirred for an additional hour, then partitioned between EtOAc (50 mL) and water (50 mL). The organic phase was separated and the aqueous phase extracted with EtOAc (3×50 mL). The combined organic extracts were subsequently washed with 2N NaOH (20 mL), dried over magnesium sulfate, filtered and evaporated to dryness under reduced pressure to give a yellowish residue. This residue was purified by flash chromatography (EtOAc/hexane 2:1, 15 cm×2 cm) to give in order of elution +/−23 ($R_f$ 0.43 EtOAc/hexane 2:1) and +/−24 ($R_f$ 0.38 EtOAc/hexane 2:1). Appropriate fractions were combined, solvent removed under reduced pressure and each solid recrystallized from aqueous methanol to give 100 mg (35%) of +/−24 and 100 mg (35%) of +/−23.

Compound +/−23: mp 180–181° C.; $R_f$ 0.38 (EtOAc/hexane 2:1); $^1$H-NMR(360 MHz DMSO-d$_6$): δ8.49 (d, 1H, J=2.0 Hz), 7.64 (d, 1H J=9.6 Hz), 7.45 (dd, 1H J=9.6 Hz, J=2.0 Hz), 5.19 (d, 1H, J=6.3 Hz, D$_2$O exchangeable), 5.11 (broad s, 1H, D$_2$O exchangeable), 5.03 (d, 1H J=9.03 Hz), 4.43 (m, 1H), 4.32 (m, 1H), 4.20 (m, 1H), 3.75 (m, 1H); $^{13}$C-NMR (90 MHz, DMSO-d$_6$): δ141.79, 134.14, 126.50, 125.85, 118.77, 116.68, 116.56, 75.74, 73.83, 71.10, 70.96; UV $\lambda_{ax}$ (ethanol) 291 (3740), 234 (25960); (pH 11) 288 (4339), 233 (27841); (pH 1) 287 (7748), 227 (28099); HRMS m/z calcd for $C_{11}H_{10}Cl_2N_2O_3$ 288.0068, found 288.0065. Anal. Calcd for $C_{11}H_{10}Cl_2N_2O_3$: C, 45.70; H, 3.49; N, 9.69. Found: C, 45.42; H, 3.51; N, 9.33.

Compound +/−24: mp 183° C.; $R_f$ 0.43 (EtOAc/hexane 2:1); $^1$H-NMR (360 MHz, DMSO-d$_6$): δ8.83 (d, 1H J=2.0 Hz), 7.58 (d, 1H, J=9.6 Hz), 7.40 (dd, 1H J=9.6 Hz, J=2.0 Hz), 5.40 (d, 1H, J=4.2 Hz, D$_2$O exchangeable), 5.26 (m, 2H, simplifies to d, 1H J=4.3 Hz upon D$_2$0wash), 4.40 (t, 1H, J=5.3 Hz), 4.26 (m, 1H), 3.82 (q, 1H), 3.89 (q, 1H; $^{13}$C-NMR (90 MHz, DMSO-d$_6$): δ141.44, 134.85, 126.60, 123.36, 120.22, 117.37, 117.11, 73.65, 73.44, 72.32, 70.28; UV $\lambda_{ax}$ (ethanol) 291 (4162), 233 (19596); (pH 11) 289 (4458), 233 (26566); (pH 1) 288 (6416), 226 (26295); HRMS m/z calcd for $C_{11}H_{10}Cl_2N_2O_3$ 288.0068, found 288.0079. Anal. Calcd for $C_{11}H_{10}Cl_2N_2O_3$: C, 45.70; H, 3.49; N, 9.69. Found: C, 45.37; H, 3.39; N, 9.35.

Figure 5:
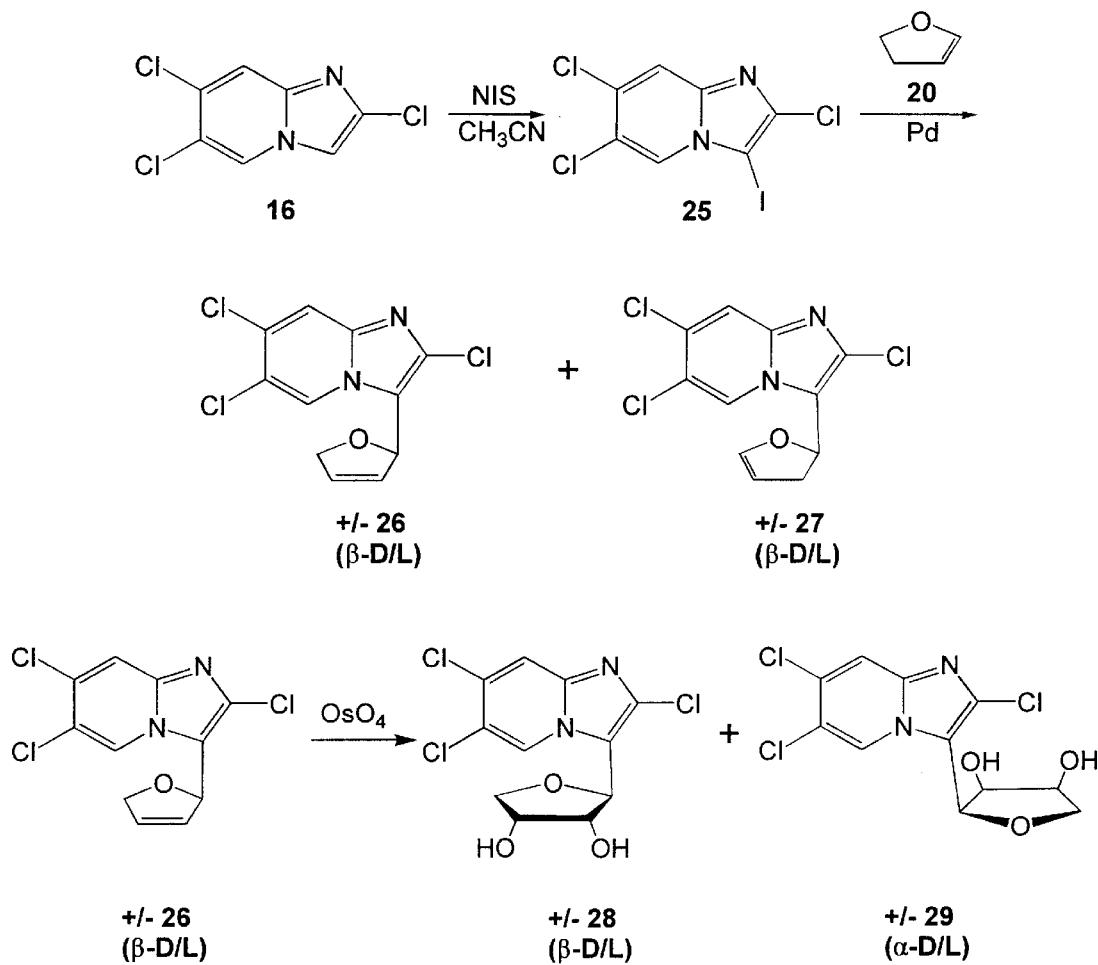
FIG. 5 is a flowchart illustrating methods for the chemical synthesis of various 2,6,7-trichloro-imidazo[1,2-a]pyridine C3-nucleosides.

The synthetic strategy used in the preparation of compounds 25, +/−26, +/−27, +/−28, and +/−29 is illustrated in FIG. 5. 2,6,7-trichloro-imidazo[1,2-a]pyridine (compound 16) was reacted with NIS (an iodinating agent) in acetonitrile (i e., $CH_3CN$) to form 3-iodo-2,6,7-trichloro-imidazo[1,2-a]pyridine (compound 25). The iodinated compound was subsequently reacted with 2,3-dihydrofuran (compound 20) and palladium to yield two isomeric 3-substituted compounds (compounds 26 and 27). By using different ligands, solvents, and temperatures. a range of relative yields of compounds 26 and 27 were obtained, as shown below in Table 2.

TABLE 2

| Palladium Coupling Conditions | | | | | | |
|---|---|---|---|---|---|---|
| # | Base | Lignad | Solvent | Temp (° C.) | % 21 | % 22 |
| 1 | Et$_3$N | Ph$_3$P | CH$_3$CN | 25 | 10 | 7 |
| 2 | Et$_3$N | Ph$_3$As | CH$_3$CN | 25 | 23 | 24 |
| 3 | Et$_3$N | Ph$_3$As | CH$_3$CN | 25–80 | 15 | 27 |
| 4 | Et$_3$N | Ph$_3$P | DMF | 25 | 20 | 10 |
| 5 | Et$_3$N | Ph$_3$As | DMF | 25 | 55 | 35 |

Compound 25

3-Iodo-2,6,7-trichloro-imidazo[1,2-a]pyridine (25). Following the preparation of compound 19, compound 16 (1.7 g, 7.7 mmol) was treated with NIS to give 2.2 g (82%) of compound 25 as a white crystalline solid.

Compound 25: mp 215–216° C.; $R_f$ 0.54 (EtOAc/hexane 1:2); $^1$H-NMR (360 MHz DMSO-d$_6$): δ8.62 (s, 1H), 7.69 (s, 1H); $^1$H-NMR (360 MHz, CDCl$_3$) δ8.20 (d, 1H, J=0.5 Hz), 7.69 (d, 1H, J=0.5 Hz); $^{13}$C-NMR (90 MHz, DMSO-d$_6$): δ144.08, 141.85, 130.14, 126.64 (C5), 119.98, 116.49 (C8), 66.67 (C3); HRMS m/z calcd for $C_7H_2Cl_3IN_2$ 345.8329, found 345.8332. Anal. Calcd for $C_7H_2Cl_3IN_2$: C, 24.20; H, 0.58; N, 8.06. Found: C, 24.52; H, 0.71; N, 8.15.

Compounds 26 and 27

2,6,7-Trichloro-3-(2',3'-dideoxy-2',3'-didehydro-β-D/L-erythro-furanosyl)-imidazo[1,2-a]pyridine (+/−26)

2,6,7-Trichloro-3-(2',3'-dideoxy-3',4'-didehydro-β-D/L-erythro-furanosyl)-imidazo[1,2-a]pyridine (+/−27)

When compound 25 (190 mg, 0.55 mmol) was treated according to procedure A, described above, 90 mg (57%) of +/−26 and 71 mg (43%) of compound +/−27 were obtained. When compound 25 (200 mg, 0.64 mmol) was treated according to procedure B, described above, only compound +/−26 was obtained (163 mg, 81%).

Compound +/−26: mp 134–135° C.; $R_f$ 0.21 (EtOAc/hexane 1:10); $^1$H-NMR (300 MHz, CDCl$_3$): δ8.10 (d, 1H, J=0.6 Hz), 7.66 (d, 1H, 0.6 Hz), 6.32 (m, 1H), 6.27 (m, 1H), 5.94 (m, 1H), 4.9 (m, 2H); $^{13}$C-NMR (90 MHz, CDC$_{13}$): δ142.59, 136.52, 131.46, 130.31, 125.78, 123.76, 120.58, 117.2, 116.99, 78.53, 75.86. Anal. Calcd for $C_{11}H_7Cl_3N_2 \cdot \frac{1}{4}$ H$_2$O: C, 44.93; H, 2.57; N, 9.53. Found: C, 45.05; H, 2.64; N, 9.41.

Compound +/−27: mp 150–151° C.; $R_f$ 0.36 (EtOAc/hexane 1:10); $^1$H-NMR (360 MHz, CDCl$_3$): δ8.15 (d, 1H, J=0.6 Hz), 7.70 (d, 1H, 0.6 Hz), 6.56 (m, 1H), 6.00 (dd, 1H J=9.8 Hz, J=11.7 Hz), 5.26 (m, 1H), 3.08 (m, 1H), 2.80 (m, 1H); $^{13}$C-NMR (90 MHz, CDC$_{13}$): δ146.06, 142.69, 136.40, 131.63, 124.27, 121.10, 118.64, 117.25, 100.53, 73.23, 32.63. Anal. Calcd for $C_{11}H_7Cl_3N_2O$: C, 45.63; H, 2.44; N, 9.67. Found: C, 45.59; H, 2.59; N, 9.36.

Compounds 28 and 29

2,6,7-Trichloro-3-(β-D/L-erythro-furanosyl)imidazo[1,2-a]pyridine (+/−28)

2,6,7-Trichloro-3-(α-D/L-erythro-furanosyl)imidazo[1,2-a]pyridine (+/−29)

Following the procedure for the preparation of compounds 23 and 24, treatment of racemic compound 26 (490 mg, 1.69 mmol) with OSO$_4$ gave 160 mg (29%) of racemic compound 28 and 170 mg (31%) of racemic compound 29, after flash chromatography (EtOAc/hexane 2:1, 15 cm×4 cm) and recrystallization from aqueous ethanol.

Compound +/−28: mp 190–192° C.; $R_f$ 0.11 (4% MeOH in CHCl$_3$); $R_f$ 0.41 (EtOAc/hexane 2:1); $^1$H-NMR (360 MHz, DMSO-d$_6$): δ8.69 (s, 1H), 8.06 (s, 1H), 5.18 (d, 1H, J=6.8 Hz, D$_2$O exchangeable), 5.11 (d, 1H, J=3.8 Hz, D$_2$O exchangeable), 5.04 (d, 1H, J=8.9 Hz, 1'-H), 4.42 (m, 1H), 4.33 (dd, 1H J=9.5 Hz, J=4.3 Hz), 4.2 (m, 1H, 3.75 (dd, 1H, J=9.5 Hz, J=1.6 Hz); $^{13}$C-NMR (90 MHz, DMSO-d$_6$): δ141.48 (C8a), 135.42 (C2), 129.47 (C7), 124.79 (C5), 118.99 (C6), 117.40 (C3), 116.58 (C8), 73.73, 73.40, 72.64, 70.26; UV $\lambda_{max}$ (ethanol) 325 (3103), 296 (3000), 287 (3008), 237 (19676); (pH 11) 320 (1000), 295 (2697), 243 (22889); (pH 1) 297 (3553), 237 (18940). HRMS m/z calcd for C$_{11}$H$_{10}$Cl$_3$N$_2$O$_3$ 321.9679, found 321.9683.

Compound +/−29: mp 224° C. (dec); $R_f$ 0.18 (4% MeOH in CHCl$_3$), $R_f$ 0.45 (EtOAc/hexane 2:1); $^1$H-NMR (360 MHz, DMSO-d$_6$): δ9.03 (s, 1H), 8.00 (s, 1H), 5.40 (d, 1H, J=4.5 Hz, D$_2$O exchangeable), 5.31 (d, 1H J=5.5 Hz, D$_2$O exchangeable), 5.24 (d, 1H J=4.8 Hz, 1'-H), 4.39 (m, 1H), 4.28 (m, 1H), 3.84 (m, 2H); $^{13}$C-NMR (90 MHz, DMSO-d$_6$): δ141.82 (C8a), 134.87 (C2), 129.39 (C7), 127.08 (C5), 117.59 (C6), 116.74 (C3), 115.93 (C8), 75.49, 73.79, 71.07, 71.02; UV $\lambda_{max}$ (ethanol) 320 (1040), 296 (1080), 285 (1012), 235 (14600); (pH 11) 320 (3700), 296 (4100), 243 (29600); (pH 1) 297 (5500), 236 (24691); HRMS m/z calcd for C$_{11}$H$_{10}$Cl$_3$N$_2$O$_3$ 321.9679, found 321.9694.

Figure 6:
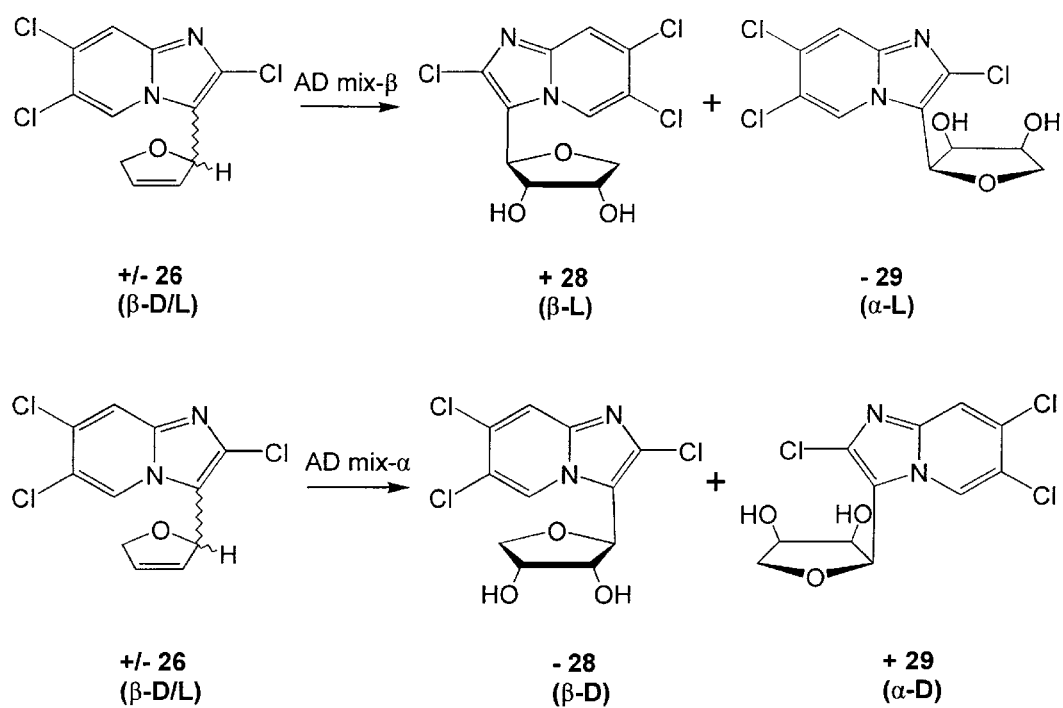
FIG. 6 is a flowchart illustrating a method for the chemical synthesis and resolution of various 2,6,7-trichloro-imidazo[1,2-a]pyridine C3-nucleoside stereoisomers.

The synthetic strategy used in the preparation and resolution of compounds +28, −28, +29 and −29 is illustrated in FIG. 6. Compound 26 (a racemic mixture) was divided into two lots; one lot was reacted with AD-mix-α and the other with AD-mix β. AD-mix-α and AD-mix β are commercially available (Aldrich Chemical Company) reagents for Sharpless Asymmetric Dihydroxylation (see J. Org. Chem., 1992, Vol. 57, p. 2768). Reaction with AD-mix-α yielded compound −28 (UMJD 1210), the β-D-erythrose analog (rotation −36.8), and compound +29 (UMJD 1209), the α-D-erythrose analog (rotation +70.75). Reaction with AD-mix-β yielded compound +28 (UMJD 1208), the β-L-erythrose analog (rotation +32.3), and compound −29 (UMJD 1207), the α-L-erythrose analog (rotation −65.8).

Compounds +28, −28, +29, and −29

2,6,7-Trichloro-3-(β-L-erythrofuranosyl)imidazo[1,2-a]pyridine (+28) and 2,6,7-dichloro-3-(α-L-erythrofuranosyl)imidazo[1,2-α]pyridine (−29).

2,6,7-Trichloro-3-(β-D-erythrofuranosyl)imidazo[1,2-a]pyridine (−28) and 2,6,7-trichloro-3-(α-D-erythrofuranosyl)imidazo[1,2-α]pyridine (+29)

A 25 mL round bottom flask was charged with t-BuOH (10 mL), water (10 mL) and AD-mix-β (3.6 g). Methansulfonamide (154 mg, 1.6 mmol) was added to this solution. The resulting mixture was cooled to 0° C.and compound +/−26 (490 mg, 1.7 mmol) was added. The reaction was allowed to warm to room temperature and was stirred for 32 hours. Sodium sulfite (3 g) was added to the reaction and the resulting mixture stirred for an additional hour. Water (50 mL) was added and the resulting suspension was extracted with EtOAc (3×70 mL). The organic phase was dried (MgSO$_4$), filtered and the volatiles removed under reduced pressure. The resulting solid was purified by flash chromatography (EtOAc/hexane 2:1, 15 cm×2 cm). The compound first eluted from the column was compound −29, fractions containing compound −29 were pooled and evaporated to dryness to give 160 mg (29%) of a white solid. The second compound eluted from the column was compound +28. Fractions containing compound +28 were pooled and evaporated to dryness to give 170 mg (31%) of a white solid. Treatment of compound +/−26 (500 mg, 1.69 mmol) with AD-mix-α as described above gave after workup 170 mg (31%) of compound −28 and 140 mg (25%) of compound +29. In the determination of the enantiomeric excess, sample preparation and spectral analysis was as follows. The shift reagent was dried in an Abderhalden apparatus for 6 hours at room temperature prior to use. Samples were dried in an Abderhalden apparatus for 24 hours prior to use. An appropriate quantity of shift reagent (2 equiv) was added to compound (1 equiv) in acetone-d$_6$ (0.4 mL) under argon atmosphere. NMR spectra were obtained on a Bruker WP 360 SY spectrometer using 0.2 Hz exponential line broadening. Samples containing equal weight of compounds as well as compounds in a 1:2 ratio were prepared and the known composition of these compared with those determined from the NMR. The integration routine of the spectrometer was used to determine relative area of peaks.

Compound +28: $R_f$ 0.41 (EtOAc/hexane 2:1); [α]D$_2$O=+32.2°, ee 38.4%. Anal. Calcd. for C$_{11}$H$_{10}$Cl$_3$N$_2$O$_3$.¾ H$_2$O: C, 39.20; H, 3.14; N, 8.31. Found: C, 39.24, H, 3.18, N, 8.02.

Compound −28: $R_f$ 0.41 (EtOAc/hexane 2:1); [α]D$_2$O=−36.8°, ee 38.4%. Anal. Calcd. for C$_{11}$H$_{10}$Cl$_3$N$_2$O$_3$.¾ H$_2$O: C, 39.20; H, 3.14; N, 8.31. Found: C, 39.18; H, 3.31; N, 7.98.

Compound +29: $R_f$ 0.45 (EtOAc/hexane 2:1); [α]D$_2$O=+70.75°, ee 87.6%. Anal. Calcd. for C$_{11}$H$_{10}$Cl$_3$N$_2$O$_3$: C, 40.83; H, 2.80; N, 8.66. Found: C, 41.07; H, 2.98; N, 8.70.

Compound −29: $R_f$ 0.45 (EtOAc/hexane 2:1); [α]D$_2$O=−65,8°, ee 87.6%. Anal. Calcd. for C$_{11}$H$_{10}$Cl$_3$N$_2$O$_3$: C, 40.83; H, 2.80; N, 8.66. Found: C, 41.01; H, 2.84; N, 8.48.

Figure 11:
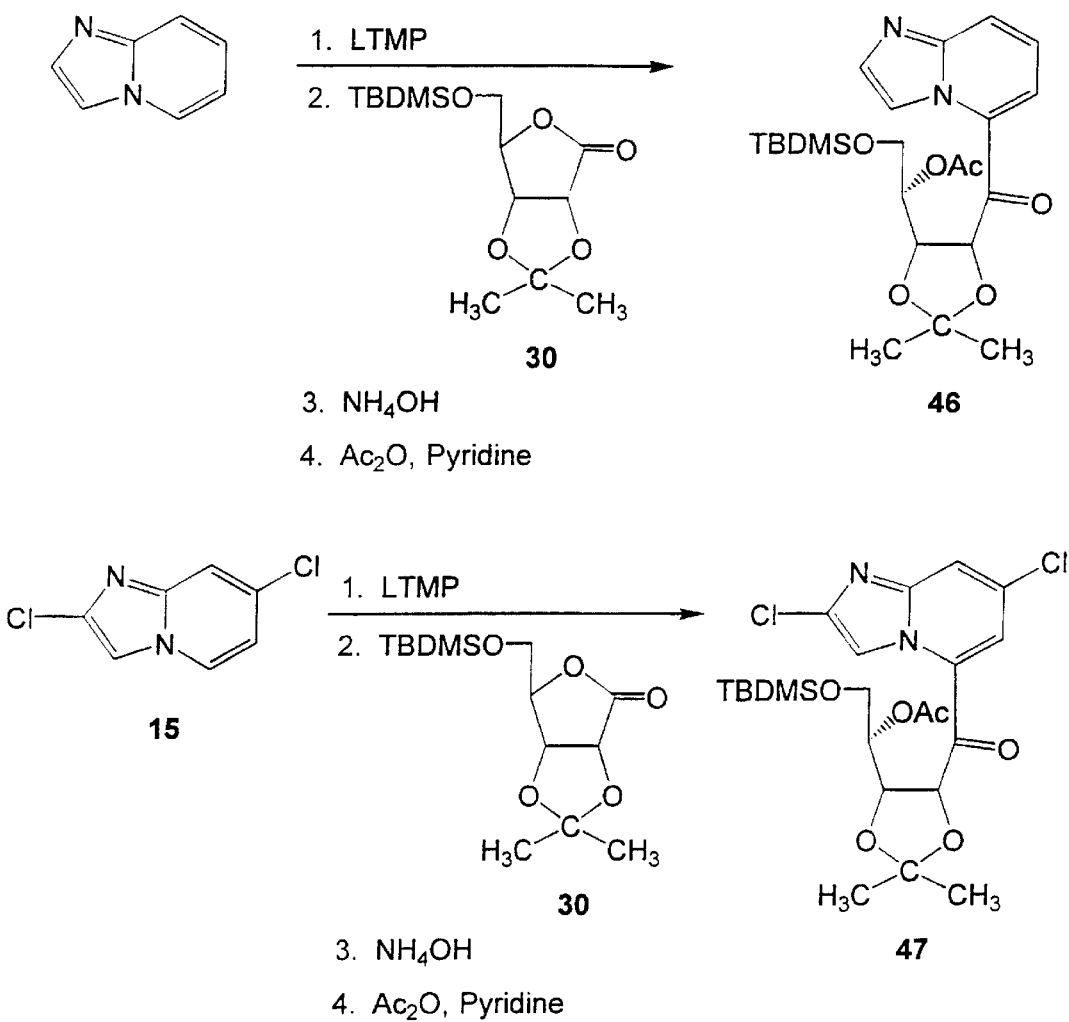
FIG. 11 is a flowchart illustrating a method for the chemical synthesis of various imidazo[1,2-a]pyridine C3-nucleosides and 2,7-dichloro-imidazo[1,2-a]pyridine C5-nucleosides.

The synthetic strategy used in the preparation of compounds 46 and 47 is illustrated in FIG. 11.

Compound 46

1-C-[Imidazo[1,2-a]pyridine-3-yl]-4-O-acetyl-5-O-[(tert-butyl)dimethylsilyl]2,3-O-isopropylidene-D-ribose (46). To a solution of TMP (3.0 mL, 17.8 mmol) in THF (40 mL) at 0° C.was added n-BuLi (11.0 mL, 17.8 mmol, 1.6 M solution in hexanes). This solution was stirred for 30 min at 0° C. and then cooled to −78° C. A solution of imidazo[1,2-a]pyridine (1.5 mL, 14.8 mmol) in THF (10 mL) was added dropwise over a period of 5 min. The resulting dark brown solution was stirred at −78° C. for 30 min. A solution of the lactone, compound 30 (1.4 g, 4.5 mmol) in THF (10 mL) was then added dropwise over a period of 10 min and the resulting black reaction mixture was stirred for 30 min at −78° C. The reaction mixture was poured into an NH$_4$Cl buffer (150 mL). This aqueous solution was extracted with EtOAc (3×100 mL), the organic phase dried over magnesium sulfate and the EtOAc removed under reduced pressure to give a yellowish oil which was dissolved in pyridine (40 mL). To this pyridine solution was added Ac$_2$O(3.9 mL, 41.0 mmol) and the resulting mixture was stirred under argon for 12 h. The reaction mixture was poured into ice-water and extracted with EtOAc (3×100 mL). The EtOAc extracts were combined and dried over magnesium sulfate, evaporated under reduced pressure to give a yellowish syrup which was purified by flash chromatography (EtOAc/hexane 1:1, 15 cm×4 cm) to give 3 g (44%) of compound 46 as a solid.

Compound 46: mp 115–116° C.; $R_f$ 0.4 (EtOAc/hexane 1:1); $^1$H-NMR (300 MHz, CDCl$_3$): δ9.67 (dd, 1H, J=0.6 Hz, J=5.8 Hz), 8.57 (s, 1H), 7.82 (m, 1H J=8.9 Hz), 7.57 (m, 1H, J=8.9 Hz), 7.14 (m, 1H), 5.35 (d, 1H), 4.84 (m, 2H), 3.80 (m, 2H), 1.70 (s, 3H), 1.48 (s, 3H), 1.45 (s, 3H), 0.85 (s, 9H), −0.02 (s, 3H), −0.03 (s, 3H); $^{13}$C-NMR (90 MHz, CDCl$_3$): 6185.25, 169.35, 148.89, 143.84, 130.30, 129.14, 117.85, 115.88, 111.13, 79.04, 75.84, 72.63, 61.95, 26.99, 25.98, 25.39, 20.87, 20.47, 18.47, −5.33. Anal. Calcd for C$_{23}$H$_{34}$N$_2$O$_6$Si: C, 59.72; H, 7.41; N, 6.06 Found: C, 59.52 H, 7.35 N, 6.01.

Compound 47

1-C-[2,7-Dichloro-imidazo[1,2-a]pyridine-3-yl]-4-O-acetyl-5-O-[(tert-butyl)dimethylsilyl]-2,3-O-isopropylidene-D-ribose (47). Compound 15 (0.7 g, 3.7 mmol) was treated in the same way as described for imidazo[1,2-a]pyridine above (in the synthesis of compound 46) to give 0.68 g (35%) of compound 47 as white crystals.

Compound 47: mp 94–95° C.; R$_f$ 0.2 (EtOAc/hexane 1:1); $^1$H-NMR (360 MHz CDCl$_3$): δ9.70 (dd, 1H, J=7.5 Hz, J=0.7 Hz), 7.67 (dd, 1H, J=0.7 Hz, J=2.2 Hz), 7.14 (dd, 1H, J=7.5 Hz, J=2.2 Hz), 5.97 (d, 1H, J=6.5 Hz), 4.93 (dd, 1H, J=6.5 Hz, J=9.5 Hz), 4.77 (dm, 1H, J=9.5 Hz), 3.81 (m, 2H), 1.67 (s, 3H), 1.48 (s, 3H), 1.37 (s, 3H), 0.88 (s, 9H), 0.01 (2s, 6H). Anal. Calcd for C$_{23}$H$_{32}$Cl$_2$N$_2$O$_6$Si: C, 51.98; H, 6.07; N, 5.27 Found: C. 51.91 H, 6.18 N, 5.03.

Figure 12:
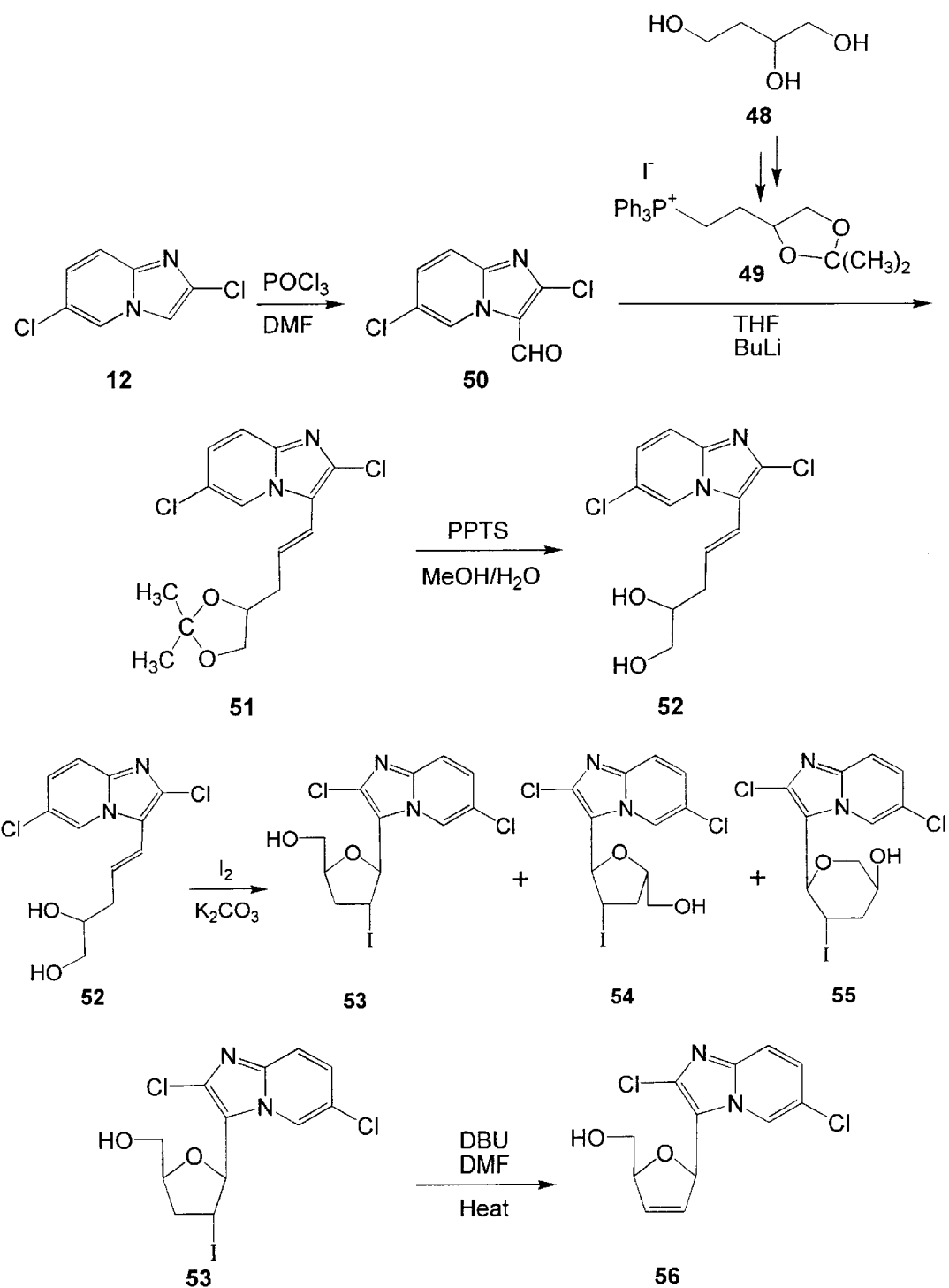
FIG. 12 is a flowchart illustrating a method for the chemical synthesis of various 2,6-dichloro-imidazo[1,2-a]pyridine C3-nucleosides.

The synthetic strategy used in the preparation of compounds 49, 50, 51, 52, 53, 54, 55, and 56 is illustrated in FIG. 12.

Compound 49

3,4-O-Isopropylidene-3,4-dihydroxybut-1-yl-triphenylphosphonium iodide (49). Compound 49 was prepared in several steps from compound 48 as described in Kang et al., Bull. Korean Chem. Soc., 1990, Vol. 11, pp. 455–460.

Compound 49: mp 210–215° C.; $^1$H-NMR (360 MHz, CDCl$_3$): δ7.8–7.9 (m, 9H), 7.7–7.8 (m, 6H), 4.5–4.6 (m, 1H), 4.1–4.3 (m, 1H), 4.15 (dd, 1H), 3.62 (dd, 1H), 3.4–3.5 (m, 1H), 2.0–2.2 (m, 1H), 1.7–1.9 (m, 1H), 1.32 (s, 3H), 1.30 (s, 3H); $^1$H-NMR (360 MHz, DMSO-d$_6$): δ7.83 (m, 15 H), 4.19 (m, 1H), 4.01 (q, 1H), 3.61 (m, 2H), 1.28 (s, 3H), 1.25 (s, 3H).

Compound 50

2,6-Dichloro-3-formyl-imidazo[1,2-a]pyridine (50). Compound 12 (1.0 g, 5.4 mmol) was dissolved in DMF (5 mL) and the solution cooled to 0° C.in an ice-water bath. To this solution was added POCl$_3$ (0.6 mL, 6.4 mmol) and the mixture stirred for 15 min. The bath was removed and the mixture warmed to room temperature and stirred for 3 hours. This reaction mixture was poured into ice water. The aqueous suspension was made basic by the addition of concentrated NH$_4$OH and the precipitated solid collected by filtration. This solid was dissolved in CHCl$_3$ (50 mL) and the solution extracted with water (3×50 mL), dried (MgSO$_4$) and solvent removed under reduced pressure to give 1.0 g (87%) of compound 50 as a white solid.

Compound 50: mp 165–166° C.; R$_f$ 0.58 (2% MeOH in CHCl$_3$); $^1$H-NMR (360 MHz, CDCl$_3$): δ10.0 (s, 1H), 9.59 (m, 1H J=0.8 Hz, J=2.0 Hz), 7.67 (dd, 1H, J=0.8 Hz, J=9.5 Hz), 7.58 (dd, 1H, J=2.0 Hz, J=9.5 Hz); $^1$H-NMR (360 MHz, DMSO-D$_6$): δ9.92 (s, 1H), 9.40 (q, 1H), 7.88 (q, 2H); 177.56, 145.59, 144,07, 132.24, 125.37, 123.35, 118.64, 117.68; HRMS m/z Calcd for C$_8$Cl$_2$N$_2$O 213.9701, found 213.9699. Anal. Calcd for C$_8$H$_4$Cl$_2$N$_2$O: C, 44.68; H, 1.87; N, 13.01. Found: C, 44.63; H, 2.14; 13.19.

Compound 51

2,6-Dichloro-3-(1',2'-O-isopropylidene-1',2'-dihydroxy-pent-4(E)-en-5-yl) imidazo[1,2-a]pyridine (51). The phosphonium iodide, compound 49 (1.32 g, 2.55 mmol) was suspended in dry THF (10 mL), the suspension cooled to 0° C. (ice-water bath) under an argon atmosphere and n-BuLi (1.8 mL of 1.6 M solution in hexanes, 2.81 mmol) was added dropwise to this suspension. The reddish solution that formed was stirred at 0° C. for 10 min and then a solution of the formyl compound 50 (0.55 g, 2.55 mmol) in THF (10 mL) was added. The reaction mixture was stirred at 0° C. for 1 hr and then poured into a saturated solution of NaHCO$_3$ (100 mL). The resulting mixture was extracted with EtOAc (3×70 mL), the organic phase dried (MgSO$_4$), filtered, and concentrated. The solid residue was purified by flash chromatography (Et$_2$O/hexane 4:1, 15 cm×4 cm). The fractions containing the product were combined and concentrated to dryness to give, after recrystallization from EtOH 625 mg (75%) of compound 51 as a white crystalline solid.

Compound 51: mp 124–125° C.; R$_f$ 0.26 (Et2O/hexane 4:1), $^1$H-NMR (360 MHz CDCl$_3$,): δ8.17 (d, 1H), 7.48 (d, 1H), 7.20 (dd, 1H), 6.48 (m, 2H), 4.32 (m, 1H), 4.12 (q, 1H), 3.70. (q, 1H), 2.63 (m, 2H), 1.48 (s, 3H), 1.39 (s, 3H); $^1$H-NMR (360 MHz, DMSO-d$_6$): δ8.87 (d, 1H, J=1.9 Hz), 7.60 (d, 1H, J=9.5 Hz), 7.40 (dd, J=9.5 Hz, J=1.9 Hz), 6.87 (d, 1H, 16.2 Hz), 6.50 (dt, 1H J=16.2 Hz, J=7.2 Hz, J=7.2 Hz), 4.26 (m 1H), 4.03 (q, 1H), 3.63 (q, 1H), 2.55 (m, 2H), 1.37 (s, 3H), 1.29 (s, 3H); $^{13}$C-NMR (90 MHz, DMSO-d$_6$): 6140.29, 135.31, 132.48, 129.13, 126.37, 122.37, 120.63, 117.14, 116.02, 108.24, 74.51, 67.88, 34.00, 26.76, 25.48; HRMS m/z calcd for C$_{15}$H$_{16}$Cl$_2$N$_2$O$_2$, 326.0589, found 326.0591. Anal. Calcd for C$_{15}$H$_{16}$Cl$_2$N$_2$O$_2$: C, 55.06, H, 4.93; N, 8.56. Found: C. 55.25; H, 4.90; N, 8.45.

Compound 52

2,6-Dichloro-3-(1',2'-dihydroxy-pent-4'-(E)-en-5'-yl) imidazo[1,2-a]pyridine (52). To a solution of compound 51 (1.8 g, 5.5 mmol) in a 1:1 mixture of H$_2$O and MeOH (50 mL) was added pyridinium para-toluenesulfonate (PPTS, 1.8 g, 7.2 mmol) and the reaction mixture heated at 60° C. for 12 hours. Methanol was removed under reduced pressure and the resulting aqueous mixture was extracted with EtOAc (3–80 mL). The organic phase was dried (MgSO$_4$), filtered, and concentrated. The resulting residue was purified by flash chromatography (EtOAc/hexane 2:1, 15 cm×5 cm). Fractions containing the product were combined and evaporated to dryness to give after recrystallization from EtOH 1.5 g (95%) of compound 52 as a white solid which retained 0.5 moles of EtOH.

Compound 52: mp 67–70° C.; R$_f$ 0.12 (EtOAc/hexane 2:1); $^1$H-NMR (360 MHz, DMSO-d$_6$): δ8.85 (d, 1H, J=1.8 Hz), 7.60 (d, 1H, J=9.5 Hz), 7.39 (dd, J=1.8 Hz, J=9.5 Hz), 6.77 (d, 1H, J=16.2 Hz), 6.60 (dt, 1H, J=16.2 Hz, J=7.1 Hz, J=7.1 Hz), 4.71 (d, 1H, D$_2$O exchangeable, J=5.0 Hz), 4.61 (t, 1H D$_2$O exchangeable, J=5.7 Hz), 3.59 (m, 1H), 3.35 (m 3H), 2.30 (m, 1H). Anal. Calcd for Cl$_2$H$_{12}$Cl$_2$N$_2$O$_2$ * ½ EtOH: C, 50.34; H, 4.87, N, 9.03. Found: C, 50.22; H, 5.22; N, 8.76.

Compounds 53, 54, and 55

2,6-Dichloro-3-(2',3'-dideoxy-2'-iodo-β-D/L-ribofuranosyl) imidazo[1,2-a]pyridine (53)

2,6-dichloro-3-(2',3'-dideoxy-2'-iodo-α-D/L-lyxofuranosyl) imidazo[1,2-a]pyridine (54)

2,6-dichloro-3-(2',3'-dideoxy-2'-iodo-α-D-lyxopyranosyl) imidazol[1,2-a]pyridine (55).

A solution of compound 52 (570 mg, 2 mmol) in dry THF (20 mL) was added to a solution of iodine (2.5 g, 9.85 mmol) in THF (10 mL). The reaction mixture was stirred for 30 min at room temperature, then $K_2CO_3$ (285 mg, 2.1 mmol) was added, followed by the addition of another portion of $K_2CO_3$ (285 mg, 2.1 mmol) after 60 min. Once all the starting material had reacted as observed by TLC, the reaction mixture was poured into EtOAc (100 mL) and extracted with saturated aqueous sodium thiosulfate (50 mL×2). The organic phase was dried over magnesium sulfate, filtered and concentrated to an oil. The resulting oil contained three products that were separated by flash chromatography (EtOAc/hexane 1:2, 15 cm×5 cm). Fractions containing each product were pooled, volatiles removed in vacuo, and each component was crystallized from aqueous EtOH to give 430 mg (52%) of compound 53, 130 mg (16%) of compound 54 and 185 (23%) mg of compound 55, all as white solids.

Compound 53: mp 190–191° C.; $R_f$ 0.55 (EtOAc/hexane 1:1); $^1$H-NMR (360 MHz, DMSO-$d_6$): δ9.18 (d, $^1$H), 7.65 (d, 1H, J=9.6 Hz), 7.46 (dd, 1H J=9.6 Hz, J=1.9 Hz), 5.39 (d, $^1$H, J=10.1 Hz), 5.34 (t, 1H, $D_2O$ exchangeable, J=4.8 Hz), 4.57 (q, 1H), 4.30 (m, 1H), 3.68 (m, 1H), 3.54 (m, 1H), 2.70 (m, 1H), 2.53 (m, 1H); $^{13}$C-NMR (90 MHz, DMSO-$d_6$): δ142.04, 135.79, 127.21, 125.14, 120.42, 117.29, 114.07, 80.32, 79.23, 62.48, 39.10, 19.14. Anal. Calcd for $C_{12}H_{11}Cl_2IN_2O_2$: C, 34.89; H, 2.68; N, 6.78. Found: C, 35.09; H, 2.85; N,6.73.

Compound 54: mp 158–160° C.; $R_f$ 0.40 (EtOAc/hexane 1:1); $^1$H-NMR (360 MHz, DMSO-$d_6$): δ8.59 (d, 1H), 7.66 (d, 1H, J=9.6 Hz), 7.47 (dd, 1H), 5.38 (d, 1H, J=10.6 Hz), 4.98 (t, 1H, $D_2O$ exchangeable, J=5.6 Hz), 4.77 (m, 1H), 4.34 (m, 1H), 3.57 (m, 1H), 3.47 (m, 1H), 2.77 (m, 1H), 2.32 (m, 1H); $^{13}$C-NMR (90 MHz, DMSO-$d_6$): δ141.92, 135.71, 127.21, 123.99, 120.43, 117.43, 114.34, 79.97, 79.12, 63.11, 39.59, 19.73. Anal. Calcd for $C_{12}H_{11}Cl_2IN_2O_2$: C, 34.89; H, 2.68; N, 6.78. Found: C, 34.81, H 2.71; N,6.80.

Compound 55: mp 205° C.; $R_f$ 0.45 (EtOAc/hexane 1:1); $^1$H-NMR (360 MHz, DMSO-$d_6$): δ8.85 (d, 1H J=1.9 Hz), 7.67 (d, 1H, J=9.6 Hz), 7.47 (dd, 1H, J=9.6 Hz, J=1.9 Hz), 5.34 (m, 1H, $D_2O$ exchangeable), 5.1–5.2 (m, 2H), 3.91 (m, 2H), 3.71 (m, 1H), 2.55 (m, 2H). Anal. Calcd for $C_{12}H_{11}Cl_2IN_2O_2$: C, 34.89; H, 2.68; N, 6.78. Found: C, 34.89; H, 2.53; N,6.64.

Compound 56

2,6-Dichloro-3-(2',3'-dideoxy-2',3'-didehydro-β-D/L-ribofuranosyl) imidazo[1,2-a]pyridine (56). To a solution of compound 53 (100 mg, 0.24 mmol) in dry DMF (5 mL) was added DBU (100 μL, 0.66 mmol) and the resulting solution stirred at 90° C. for 16 h. The reaction mixture was partitioned between water (30 mL) and $CH_2Cl_2$ (60 mL). The organic phase was separated, dried over magnesium sulfate and concentrated under reduced pressure. The resulting solid was purified by flash chromatography (EtOAc/hexane 1:1, 15 cm×2 cm). Fractions containing the product were pooled and concentrated in vacuo to give after recrystallization from aqueous EtOH 41 mg (60% ) of compound 56 as a white crystalline solid.

Compound 56: mp 155–156° C.; $R_f$ 0.41 (EtOAc/Hexane 2:1); $^1$H-NMR (360 MHz, CDCl$_3$); δ8.82 (d, 1H, J=2.0 Hz), 7.41 (d, 1H J=9.5 Hz), 7.14 (dd, 1H J=2.0 Hz, J=9.5 Hz), 6.27 (m, 1H), 6.22 (m, 1H), 6.08 (m, 1H), 4.99 (m, 1H), 3.94 (dd. 1H), 3.86 (dd, 1H); HRMS m/z calcd for $C_{12}H_{10}Cl_2N_2O_2$ 284.0119, found 284.0114. Anal. Calcd for $C_{12}H_{10}Cl_2N_2O_2$: C, 50.55, H 3.54; N, 9.82. Found: C, 50.49; H, 3.76; N, 9.70.

Figure 13:
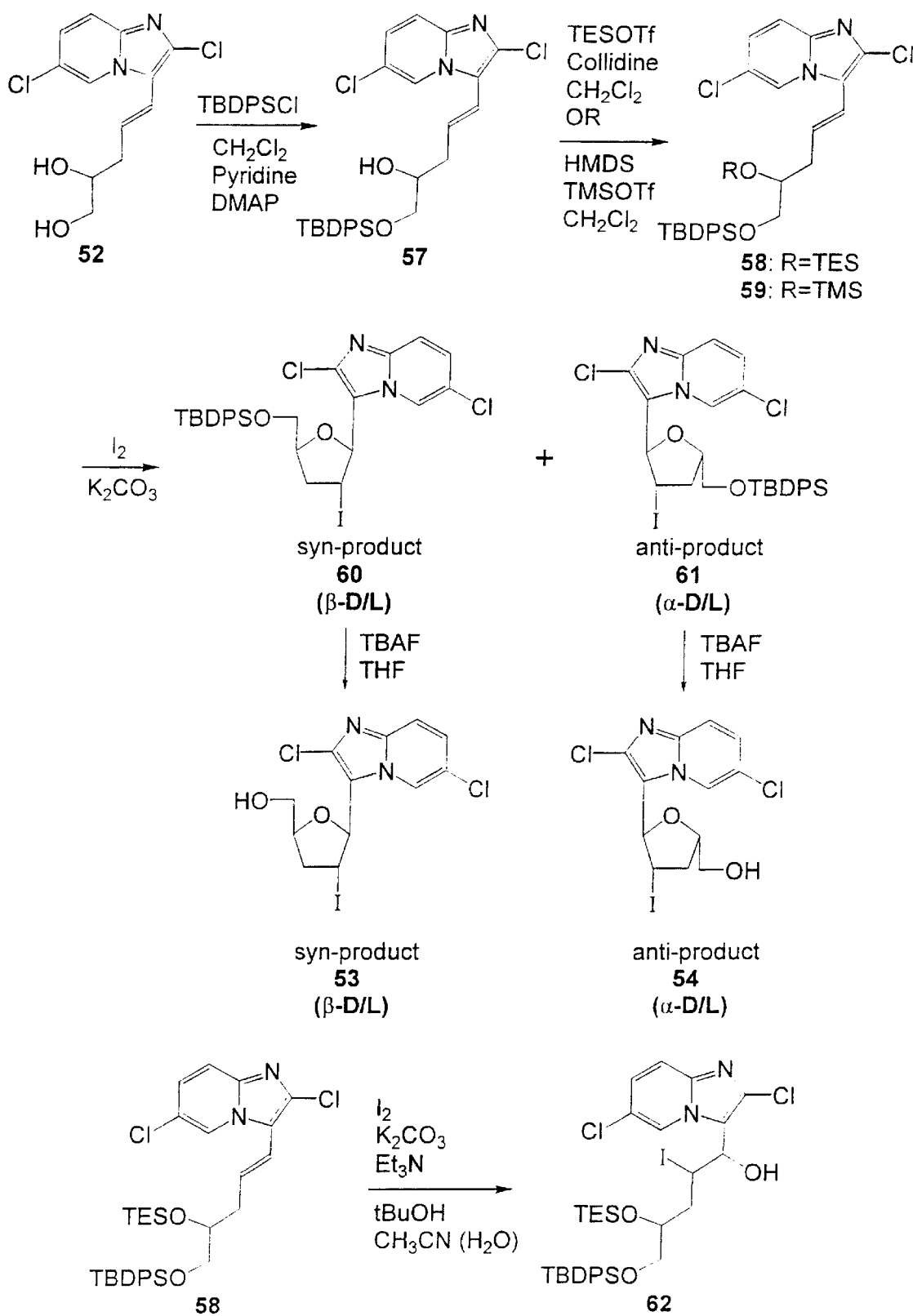
FIG. 13 is a flowchart illustrating a method for the chemical synthesis of various 2,6-dichloro-imidazo[1,2-a]pyridine C3-nucleosides.

The synthetic strategy used in the preparation of compounds 57, 58, 59, 60, 61, and 62 is illustrated in FIG. 13.

Compound 57

2,6-Dichloro-3-(1'-O-(tert-butyl)diphenylsilyl)-1',2'-dihydroxy-pent-4'-(E)-en-5'-yl) imidazo[1,2-a]pyridine (57). The diol compound 52 (140 mg, 0.49 mmol) was suspended in $CH_2Cl_2$ (5 mL) and to this suspension were added sequentially pyridine (0.5 mL, 6.2 mmol), DMAP (10 mg, 0.08 mmol) and TBDPSCl (0.16 mL, 0.6 mmol). The resulting reaction mixture was stirred for 12 h at ambient temperature. Water was added and the mixture extracted with EtOAc (3×40 mL). The organic extracts were dried (MgSO$_4$), filtered, and concentrated. The resulting residue was purified by flash chromatography (EtOAc/hexane 1:2, 15 cm×2 cm). Fractions containing the product were combined and evaporated to dryness to give, after recrystallization from EtOH, 225 mg (87%) of compound 57 as a white crystalline solid.

Compound 57: mp 155–156° C.; $R_f$ 0.46 (EtOAc/hexane 1:2); $^1$H-NMR (360 MHz CDCl$_3$,): δ8.10 (d, 1H J=2.0 Hz), 7.7 (m, 4H), 7.49 (d, 1H), 7.40 (m, 6H), 7.19 (dd, 1H J=9.5 Hz, J=2.0 Hz), 6.46 (m, 2H), 3.94 (m, 1H), 3.77 (dd, 1H), 3.65 (dd, 1H), 2.52 (t, 2H), 1.70 (broad s, 1H, $D_2O$ exchangeable), 1.10 (s, 9H); $^1$H-NMR (360 MHz, DMSO-$d_6$): δ8.80 (d, 1H), 7.62 (m, 5H), 7.38 (m, 7H), 6.78 (d, 1H, J=16.2 Hz), 6.57 (dt, 1H, J=16.2 Hz, J=7.4 Hz, J=7.4 Hz), 4.9 (d, 1H, $D_2O$ exchangeable, J=5.1 Hz), 3.79 (m 1H), 3.62 (m, 1H), 3.56 (m, 1H), 2.59 (m, 1H), 2.47 (m, 1H), 1.00 (s, 9H); $^{13}$C-NMR (90 MHz, DMSO-$d_6$): 6140.19, 135.08, 133.07, 132.39, 131.14, 129.77, 127.80, 126.24, 122.61, 120.55, 118.07, 117.20, 115.25, 70.31, 67.52, 38.12, 26.66, 18.84. Anal. Calcd for $C_{28}H_{30}CL_2N_2O_2Si$: C, 63.99; H, 5.75; N, 5.33. Found: C, 63.78; H, 5.92; N, 5.26.

Compounds 60 and 61 via Compound 59

2.6-Dichloro-3-(2',3'-dideoxy-2'-iodo-5'-O-(tert-butyl) diphenylsilyl-β-D/L-ribofuranosyl) imidazo[1,2-a]pyridine (60)

2,6-Dichloro-3-(2',3'-dideoxy-2'-iodo-5'-O-(tert-butyl) diphenylsilyl-α-D/L-lyxofuranosyl) imidazo[1,2-a]pyridine (61)

A solution of compound 57 (200 mg, 0.38 mmol) in dry $CH_2Cl_2$ (10 mL) was cooled to 0° C., then HMDS (0.16 mL, 0.76 mmol) followed by a catalytic quantity of TMSOTf (1 drop) were added. This reaction was stirred at 0° C. for 30 min, diluted with $CH_2Cl_2$ (50 mL) and extracted with saturated aqueous NaHCO$_3$. The organic phase was dried over magnesium sulfate, filtered and evaporated to dryness to give compound 59. Compound 59 was dissolved in dry CH$_3$CN (10 mL), $K_2CO_3$ (105 mg, 0.76 mmol) was added and the resulting suspension was cooled to 0° C. A solution of iodine in CH$_3$CN (482 mg, 1.9 mmol in 10 mL CH$_3$CN) was added to the cold suspension and the reaction mixture stirred at 0° C. for 12 h. On warming to room temperature the mixture was poured into EtOAc (100 mL) and extracted with saturated aqueous sodium thiosulfate (50 mL×2), dried (MgSO$_4$), filtered and concentrated to afford a solid. This solid residue contained two products, which were separated by flash chromatography (EtOAc/hexane 1:10, 15 cm×2 cm). Fractions containing each product were pooled and concentrated to dryness to give 33 mg (13%) of compound 60 as a white solid and 17 mg (7%) of compound 61 as a white solid.

Compound 60: mp 130–32° C.; $R_f$ 0.35 (EtOAc/hexane 1:5); 1H-NMR (360 MHz, CDCl$_3$): δ8.36 (d, 1H J=2.0 Hz), 7.66 (m, 4H), 7.50 (d, 1H J=9.5 Hz), 7.4 (m, 6H), 7.21 (dd, 1H J=2.0 Hz, J=9.5 Hz), 5.43 (d, 1H, J=9.2 Hz), 4.58 (q, 1H), 4.35 (m, 1H), 3.97 (dd, 1H, J=11.4 Hz, J=3.5 Hz), 3.76 (dd, 1H, J=11.4 Hz, J=4.0 Hz), 2.80 (m, 1H), 2.54 (m, 1H), 1.14 (s, 9H). Anal. Calcd for $C_{28}H_{29}Cl_2IN_2O_2Si$: C, 51.62; H, 4.49; N, 4.30. Found: C, 51.73; H, 4.67; N, 4.14.

Compound 61: mp 80–82° C.; $R_f$ 0.32 (EtOAc/hexane 1:5); H-NMR (300 MHz, CDCl$_3$): δ8.16 (d, 1H, J=2.0 Hz), 7.7 (m, 4H), 7.52 (d, 1H, J=9.5 Hz), 7.40 (m, 6H), 7.26 (dd, 1H, J=9.5 Hz, J=2.0 Hz), 5.59 (d, 1H, 10.4 Hz), 4.56 (m, 1H), 4.39 (m, 3.92 (dd, 1H, J=11.2 Hz, J=3.3 Hz), 3.71 (dd, 1H, J=11.2 Hz, J=3.2 Hz), 2.8 (m, 2H), 1.14 (s, 9H). Anal. Calcd for $C_{28}H_{29}Cl_2IN_2O_2Si \cdot H_2O$: C, 50.23; H, 4.79; N, 4.18. Found: C, 50.01; H, 4.65; N, 4.14.

Compounds 60 and 61 via Compound 58

2.6-Dichloro-3-(2',3'-dideoxy-2'-iodo-5'-O-(tert-butyl) diphenylsilyl-β-D/L-ribofuranosyl)imidazo[1,2-a]pyridine (60)

2,6-dichloro-3-(2',3'-dideoxy-2'-iodo-5'-O-(tert-butyl) diphenylsilyl-α-D/L-lyxofuranosyl)imidazo[1,2-a]pyridine (61)

A solution of compound 57 (178 mg, 0.34 mmol) in dry CH$_2$Cl$_2$ (5 mL) was cooled to 0° C., 2,6-lutidine (51 μL, 0.44 mmol) and TESOTf (95 μL, 0.42 mmol) were then added. This reaction mixture was stirred at 0° C. for 30 min and then concentrated in vacuo to a syrup. The residue was purified by flash chromatography (EtOAc/hexane 1:10, 15 cm×2 cm), fractions containing the product were pooled and concentrated to dryness to give compound 58 as a syrup. Compound 58 was dissolved in dry CH$_3$CN (7 mL) containing Et$_3$N (30 μL, 0.17 mmol) and added dropwise to a solution of iodine (860 mg, 3.4 mmol), K$_2$CO$_3$ (94 mg, 0.68 mmol) and t-BuOH (130 μL, 1.3 mmol) in CH$_3$CN (6 mL) at 0° C. The reaction mixture was stirred at 0° C. for 1 h and then at room temperature for an additional 1 hr. The reaction mixture was subsequently poured into EtOAc (100 mL) and extracted with saturated aqueous sodium thiosulfate (50 mL×2), dried (MgSO$_4$), filtered and concentrated to a solid. This solid contained two compounds that were separated by flash chromatography (EtOAc/hexane 1:5, 15 cm×2 cm). Fractions containing each product were pooled and concentrated to dryness to give 32 mg (13%) of compound 60 and 10 mg (4%) of compound 61.

Compound 62

3-(2,6-Dichloro-imidazo[1,2-a]pyridine-3-yl)-1-O-(tert-butyl)diphenylsilyl-2-O-triethylsilyl-4-iodo-penta-1,2,5-triol (62). Compound 57 (178 mg, 0.34 mmol) was dissolved in dry CH$_2$Cl$_2$ (5 mL), treated with 2,6-lutidine (51 μL, 0.44 mmol) and TESOTf (95 μL, 0.42 mmol) and the resulting TES derivative compound 58 was purified by flash chromatography (EtOAc/hexane 1:10, 15 cm×2 cm), fractions containing product were pooled and concentrated to dryness to give compound 58 as a syrup. Intermediate compound 58 was dissolved in CH$_3$CN (7 mL, not dried) containing Et$_3$N (30 μL, 0.17 mmol) and added dropwise to a solution of iodine (860 mg, 3.4 mmol), K$_2$CO$_3$ (94 mg, 0.68 mmol) and BuOH (130 μL, 1.3 mmol) in CH$_3$CN (6 mL, not dried) at 0° C. The reaction mixture was stirred at 0° C. for 1 h and then at room temperature for an additional 1 h. The reaction mixture was poured into EtOAc (100 mL) and extracted with saturated aqueous sodium thiosulfate (50 mL×2), water removed (MgSO$_4$), filtered and concentrated to a syrup. This syrup was purified by flash chromatography (EtOAc/hexane 1:5, 15 cm×2 cm). Fractions containing the product were pooled and concentrated to dryness to give after recrystallization from CH$_3$CN 150 mg (56%) of compound 62 as a white solid.

Compound 62: mp 82–83° C.; $R_f$ 0.39 (EtOAc/hexane 1:5); H-NMR (360 MHz, CDCl$_3$): δ8.62 (d, 1H, J=2.0 Hz), 7.65 (m, 4H), 7.43 (m, 7H), 7.21 (dd, 1H, J=2.0 Hz, J=9.5 Hz), 5.50 (dd, 1H, J=3.7 Hz, J=7.1 Hz, collapses to a d on D$_2$O exchange J=7.1 Hz), 4.76 (m, 1H), 3.88 (m, 1H), 3.62 (q, 1H), 3.46 (q, 1H), 3.36 (s, 1H, D$_2$O exchangeable), 2.48 (m, 1H), 1.82 (m, 1H), 1.05 (s, 9H), 0.87 (t, 9H), 0.48 (ql 6H); $^{13}$C-NMR (90 MHz, CDCl$_3$): δ142.10, 135.86, 135.79, 135.38, 133.44, 130.00, 129.95, 127.96 (2C), 126.90, 124.03, 121.53, 118.71, 117.59, 73.02, 72.12, 67.73, 40.64, 36.88, 27.07, 19.42, 7.10, 5.29; HRMS m/z calcd. for $C_{34}H_{45}C_2IN_2O_3Si_2$-(t-Bu) 725.0667, found 725.0686. Anal. Calcd for $C_{34}H_{45}Cl_2IN_2O_3Si_2$: C, 51.39; H, 5.72; N, 3.53. Found: C, 51.71; H, 5.58; N, 3.57

Figure 14:
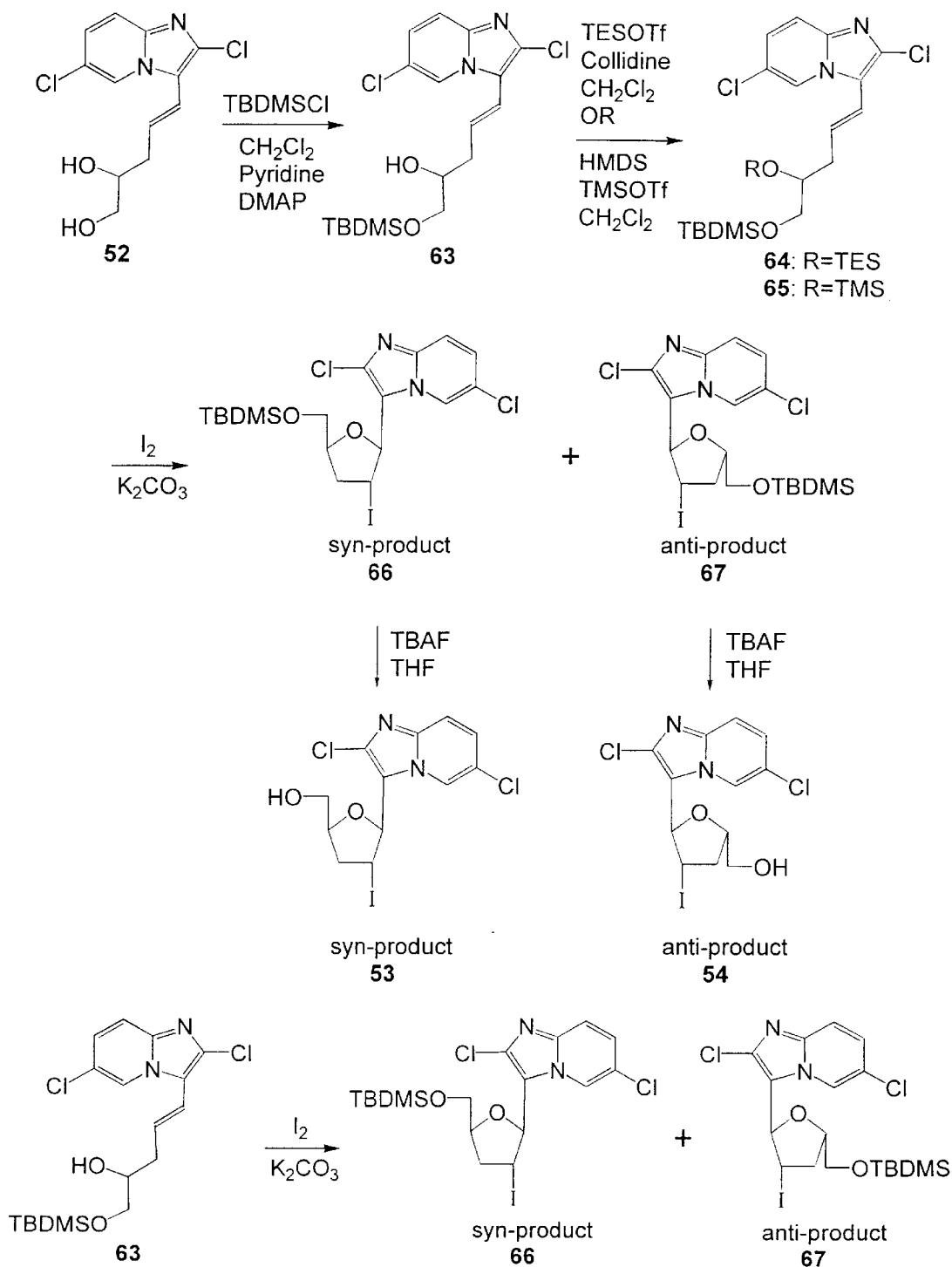
FIG. 14 is a flowchart illustrating a method for the chemical synthesis of various 2,6-dichloro-imidazo[1,2-a]pyridine C3-nucleosides.

The synthetic strategy used in the preparation of compounds 63, 64, 65, 66, and 67 is illustrated in FIG. 14.

Compound 63

2,6-Dichloro-3-(1'-O-(tert-butyl)dimethylsilyl)-1',2'-O-isopropylidene-1,2-dihy droxy-pent-4(E)-en-5-yl) imidazo [1,2-a]pyridine (63). Diol compound 52 (250 mg, 0.87 mmol) was suspended in CH$_2$Cl$_2$ (5 mL), then pyridine (0.5 mL, 6.2 mmol) and DMAP (10 mg, 0.08 mmol) were added. TBDMSCI (144 mg, 0.95 mmol) was added portionally to the mixture in three 50 mg portions at 1 h intervals. The resulting reaction mixture was stirred at ambient temperature for 12 h, then quenched with water (20 mL). The mixture was extracted with CH$_2$Cl$_2$ (3×50 mL) and the organic phase was dried over magnesium sulfate. Filtration and concentration gave a syrup which was purified by flash chromatography (EtOAc/hexane 1:5, 15 cm×2 cm). Fractions containing the product were pooled and concentrated to dryness to give 270 mg (78%) of compound 63 as a white solid.

Compound 63: mp 66–67° C.; $R_f$ 0.45 (EtOAc/hexane 1:2); H-NMR (360 MHz DMSO-d$_6$): δ8.83 (d, 1H, J=1.9 Hz), 7.60 (d, 1H J=9.5 Hz), 7.39 (dd, 1H, J=1.9 Hz, J=9.5 Hz), 6.77 (d, 1H J=16.2 Hz), 6.59 (dt, 1H J=16.2 Hz, J=7.2 Hz, J=7.2 Hz), 4.78 (d, 1H, D$_2$O exchangeable, J=5.1 Hz), 3.64 (m 1H), 3.56 (m, 1H), 3.46 (m, 1H), 2.50 (m, 1H), 2.34 (m, 1H), 0.87 (s, 9H), 0.48 (s, 6H); C$^{13}$-NMR(90 MHz, DMSO-d$_6$): δ140.18, 132.30, 131.41, 126.23, 122.64, 120.54, 118.10, 117.20, 115.12, 70.47, 67.00, 38.05, 25.87, 18.06, 6.88, −5.26, −5.32. Anal. Calcd for $C_{18}H_{26}Cl_2N_2O_2Si$: C, 53.86; H, 6.53; N, 6.98. Found: C, 53.52, H, 6.60; N, 7.06.

Compounds 66 and 67 via Compound 64

2,6-Dichloro-3-(2',3'-dideoxy-2'-iodo-5'-O-(tert-butyl) dimethylsilyl-β-D/L-ribofuranosyl) imidazo[1,2-a]pyridine (66)

2,6-dichloro-3-(2',3'-dideoxy-2'-iodo-5'-O-(tert-butyl) dimethylsilyl-α-D/L-lyxofuranosyl) imidazo[1,2-a]pyridine (67)

Compound 63 (100 mg, 0.25 mmol) was treated with 2,6-lutidine (40 μL, 0.32 mmol) and TESOTf (70 μL, 0.31 mmol) at 0° C. to form the TES derivative compound 64 which was purified as described above for compound 58. Compound 64 was reacted with iodine under conditions used for the preparation of compound 60 to give 5 mg (4%) of compound 66 and 15 mg (12%) of compound 67 as white solids.

Compound 66: mp 104–105° C.; $R_f$ 0.16 (EtOAc/hexane 1:10);$^1$H-NMR (360 MHz, CDCl$_3$): δ8.51 (d, 1H J=2.0 Hz), 7.51 (d, 1H, J=9.5Hz), 7.22 (dd, 1H, J=9.5 Hz, J=2.0 Hz), 5.42 (d, 1H, I'-H, 9.8 Hz), 4.47 (q, 1H, 2'-H), 4.35 (m, 1H, 4'-H), 4.00 (dd, 1H, J=11 5 Hz, J=2.5 Hz), 3.74 (dd, 1H, J=11.5 Hz, J=3.0 Hz), 2.75 (m, 1H), 2.57 (m, 1H), 0.95 (s, 9H), 0.15 (s, 6H); $^{13}$C-NMR (90 MHz, CDCl$_3$): δ142.79, 137.33, 127.27, 123.98, 121.63, 117.76, 113.92, 81.52, 79.64, 64.59, 39.79, 26.38, 18.83, 18.16, −4.96. Anal. Calcd for $C_{18}H_{25}Cl_{21}IN_2O_2Si$: C, 41.00; H, 4.78; N, 5.32. Found: C, 41.38; H, 4.82; N, Compound 67: mp 40–41° C.; $R_f$ 0.19 (EtOAc/hexane 1:10);$^1$H-NMR (360 CDCl$_3$): δ8.17 (d, 1H, J=1.2 Hz), 7.53 (d, 1H, J=9.5 Hz), 7,22 (dd, 1H, J=9.5 Hz, J=1.2 Hz), 5.50 (d, 1H, 10.4 Hz), 4.53 (m, 1H), 4.38 (m, 1H), 3.87 (dd, 1H J=11.0 Hz, J=3.4 Hz), 3.70 (dd, 1H, J=11.0 Hz, J=3.0 Hz), 2.85 (m, 1H), 2.65 (m, 1H), 0.97 (s, 9H), 0.14 (s, 6H); $^{13}$C-NMR (90 MHz, CDCl$_3$): δ142.64, 137.18, 126.98, 122.95, 121.56, 117.94, 114.16, 80.90, 79.59, 65.41, 39.87, 26.16, 18.48, 18.05, −5.14. Anal. Calcd for $C_{18}H_{25}Cl_2IN_2O_2Si$: C, 41.00; H, 4.78; N, 5.32. Found: C, 41.04; H, 4.98; N, 5.76.

Compounds 66 and 67

2,6-Dichloro-3-(2',3'-dideoxy-2'-iodo-5'-O-(tert-butyl) dimethylsilyl-β-D/L-ribofuranosyl) imidazo[1,2-a]pyridine (66)

2,6-dichloro-3-(2',3'-dideoxy-2'-iodo-5'-O-(tert-butyl) dimethylsilyl-α-D/L-lyxofuranosyl) imidazo[1,2-a]pyridine (67)

A solution of compound 63 (1.0 g, 2.5 mmol) in dry CH$_2$Cl$_2$ (15 mL) was added to a suspension of iodine (3.16 g, 12.5 mmol) and K$_2$CO$_3$ (0.7 g, 5.0 mmol) in dry CH$_2$Cl$_2$ (15 mL) at room temperature. The reaction mixture was stirred for 1 hour, poured into CH$_2$Cl$_2$ (200 mL) and extracted with saturated aqueous sodium thiosulfate (100 mL×2). After drying (MgSO$_4$) and filtering, the solvent was removed and the residue purified by flash chromatography (EtOAc/hexane 1:10, 15 cm×5 cm). Fractions containing each compound were pooled and volatiles removed in vacuo to give after recrystallization from CH$_3$CN 820 mg (63%) of compound 31 and 260 mg (20%) of compound 30 as white solids.

Compound 67

2,6-Dichloro-3-(2,3-dideox-2-iodo-5-O-(tert-butyl) dimethylsilyl-α-D/L-lyxofuranosyl)imidazo[1,2-a]pyridine (67). A suspension of compound 63 (100 mg, 0.25 mmol) and K$_2$CO$_3$ (70 mg, 0.5 mmol) in dry THF and under an argon atmosphere was cooled to −78° C. A solution of iodine (320 mg, 1.3 mmol) in THF (5 mL) was then added. The resulting mixture was stirred at −78° C. for 1 hour and then poured into EtOAc (50 mL). $^1$H-NMR of the crude mixture revealed that it contained compound 66 and compound 67 in 1:14 ratio. Workup and chromatography as described above gave 118 mg (89%) of compound 67 and 8 mg (6%) of compound 66 as white solids.

Figure 15:
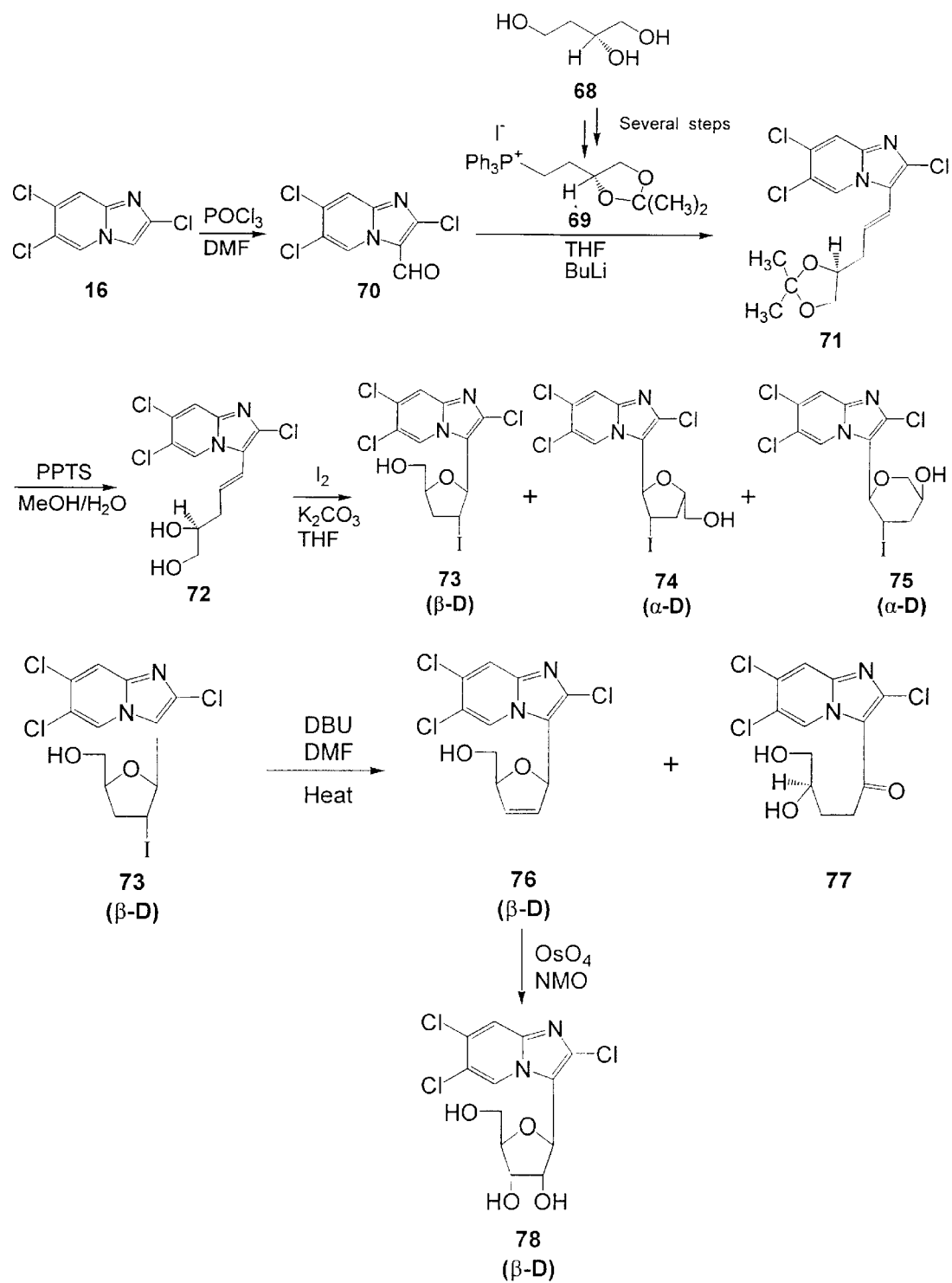
FIG. 15 is a flowchart illustrating a method for the chemical synthesis of various 2,6,7-trichloro-imidazo[1,2-a]pyridine C3-nucleosides.

The synthetic strategy used in the preparation of compounds 69, 70, 71, 72, 73, 74, 75, 76, 77, and 78 is illustrated in FIG. 15.

Compound 69

3,4-O-Isopropylidene-3(S),4-dihydroxybut-1-yl triphenylphosphonium iodide (69). Prepared in the same fashion as compound 49, using S-butane-1,2,4-triol (compound 68) as starting material.

Compound 70

2,6,7-Trichloro-3-formyl-imidazo[1,2-a]pyridine (70). To a solution of compound 16 (4.0 g, 0.018 mol) in DMF (30 mL) at 0° C. was added POCl$_3$ (2.5 mL, 0.027 mol). The mixture was stirred for 30 min at 0° C., then at room temperature for 3 hours. This reaction mixture was poured into ice water, the aqueous suspension was made basic by the addition of concentrated NH$_4$OH and the precipitated solid then collected by filtration. This solid was dissolved in CHCl$_3$; (200 mL) and the solution extracted with water (3×100 mL), dried over magnesium sulfate, filtered and evaporated to dryness to give, after recrystallization from CH$_3$CN, 4.1 g (90%) of 70 as a white solid.

Compound 70: mp 210–211° C.; $R_f$ 0.80 (2% MeOH in CHCl$_3$); $^1$H-NMR (360 MHz, DMSO-d$_6$): δ9.98 (s, 1H), 9.69 (s, 1H), 7.84 (s, 1H). Anal. Calcd for $C_8H_3Cl_3N_2O$: C, 38.51; H, 1.21; N, 11.23. Found: C, 38.48; H, 1.40; 11.22.

Compound 71

2,6,7-Trichloro-3-(1,2(S)-O-isopropylidene-1,2(S)-dihydroxy-pent-1(E)-en-5yl) imidazo[1,2-a]pyridine (71). A suspension of compound 69 (7.18 g, 0.014 mol) in dry THF (30 mL) was cooled to 0° C. under an argon atmosphere. To this suspension was added dropwise n-BuLi (9.9 mL of 1.6 M solution in hexanes, 0.016 mol). The reddish solution obtained was stirred at 0° C. for 10 min, then a solution of compound 70 (3.3 g, 0.013 mol) in THF (30 mL) was added. The reaction mixture was stirred at 0° C. for 1 h and then poured into a saturated aqueous solution of NaHCO$_3$ (200 mL) and extracted with EtOAc (3×150 mL). The organic phase was dried over magnesium sulfate, filtered and concentrated to a solid. This solid was purified by flash chromatography (Et2O/hexane 4:1, 15 cm×5 cm). Fractions containing the product were combined and evaporated to dryness to give, after recrystallization from EtOH, 3.34 g (70%) of compound 71 as a white crystalline solid.

Compound 71: mp 170–169° C.; $R_f$ 0.2 (EtOAc/hexane 1:5); $^1$H-NMR (360 MHz DMSO-d$_6$): δ9.06 (s, 1H), 7.99 (s, 1H) 6.85 (d, 1H, J=6.2 Hz), 6.51 (dt, 1H J=6.2 Hz), 4.25 (t, 1H), 4.02 (q, 1H), 3.61 (t, 1H), 2.51 (m, 2H), 1.35 (s, 3H), 1.28 (s, 3H); $^{13}$C-NMR (90 MHz DMSO-d$_6$): δ140.26, 133.03, 129.60, 129.11, 124.22, 119.23, 117.91, 116.37, 115.89, 108.24, 74.51, 67.91, 37.50, 26.79, 25.51; HRMS m/z calcd for $C_{15}H_{15}Cl_3N_2O_2$ 360.0197, found 360.0199. Anal. Calcd for $C_{15}H_{15}Cl_3N_2O_2$: C, 49.82; H, 4.18; N, 7.75. Found: C, 49.72; H, 4.11; N, 7.73.

Compound 72

2,6,7-Trichloro-3-(1,2(S)-dihydroxy-pent-4(E)-en-5-yl) imidazo[1,2-a]pyridine (72). To a solution of compound 71 (0.7 g, 1.9 mmol) in a 1:1 mixture of H$_2$O and MeOH (40 mL) was added pyridinium para-toluenesulfonate (0.7 g, 2.8 mmol) and the reaction mixture heated to 60° C. for 24 hours. The methanol was removed under reduced pressure and the resulting aqueous mixture was extracted with EtOAc (3×50 mL). The combined organic extracts were dried over magnesium sulfate, filtered, concentrated and the resulting solid purified by flash chromatography (EtOAc/hexane 2:1, 15 cm×2 cm). Fractions containing the product were combined and evaporated to dryness and the solid was recrystallized from EtOH to give 0.56 g (90%) of compound 72 as a white solid.

Compound 72: mp 161–163° C.; $R_f$ 0.25 (EtOAc/hexane 2:1); $^1$H-NMR (360 MHz, DMSO-d$_6$,): δ9.06 (s, 1H), 8.00 (s, 1H), 6.79 (d, 1H, J=16.2 Hz), 6.62 (dt, 1H, J=16.2 Hz, J=7.1 Hz), 4.71 (d, 1H, D$_2$O exchangeable), 4.61 (t, 1H-D$_2$O exchangeable), 3.61 (m, 1H), 3.33 (m, 2H), 2.5 (m, 1H), 2.3 (m, 1H); $^{13}$C-NMR (90 MHz, DMSO-d$_6$): δ140.12, 132.79, 132.16, 128.89, 124.18, 119.13, 118.24, 116.33, 114.81, 70.95, 65.46, 38.10. Anal. Calcd for C$_{12}$H$_{11}$Cl$_3$N$_2$O$_2$: C, 44.82; H, 3.45; N, 8.71. Found: C, 45.13; H, 3.81; N, 8.58.

Compounds 73, 74 and 75

2,6,7-Trichloro-3-(2,3-dideoxy-2-iodo-β-D-ribofuranosyl)imidazo[1,2-a]pyridine (73), 2,6,7-trichloro-3-(2,3-dideoxy-2-iodo-α-D-lyxofuranosyl)imidazo[1,2-a]pyridine (74), 2,6,7-trichloro-3-(2,3-dideoxy-2-iodo-α-D-lyxopyranosyl)imidazo[1,2-a]pyridine (75).

A solution of compound 72 (340 mg, 1.1 mmol) in dry THF (10 mL) was added to a stirred solution of iodine (1.3 g, 5.3 mmol) in THF (10 mL). After 30 min K$_2$CO$_3$ (150 mg, 1.1 mmol) was added, followed by the addition of a second portion of K$_2$CO$_3$ (150 mg, 1.1 mmol) after 60 min. Once all the starting material had reacted, as determined by TLC, the reaction mixture was poured into EtOAc (100 mL) and extracted with saturated aqueous sodium thiosulfate (50 mL×2), dried over magnesium sulfate, filtered and concentrated to a solid. This solid contained three compounds that were separated by flash chromatography (EtOAc/hexane 1:2, 15 cm×5 cm). Fractions containing each component were pooled and solvent removed in vacuo to give, after recrystallization from aqueous EtOH, 193 mg (45%) of compound 73, 70 mg (16%) of compound 74 and 120 mg (27%) of compound 75 as white solids.

Compound 73: mp 206–207° C.; R$_f$ 0.27 (EtOAc/hexane 1:2); $^1$H-NMR (360 MHz, DMSO-d$_6$): δ9.40 (s, 1H), 8.08 (s, 1H), 5.42 (t, 1H, D$_2$O exchangeable), 5.39 (d, 1H, J=10.0 Hz), 4.56 (q, 1H), 4.31 (m, 1H), 3.69 (m, 1H), 3.56 (m, 1H), 2.70 (m, 1H), 2.55 (m, 1H) $^{13}$C-NMR (90 MHz, DMSO-d$_6$): δ142.15, 136.36, 130.16, 126.64, 119.13, 116.48, 114.32, 80.29, 79.31, 62.43, 39.10, 19.34. Anal. Calcd for C$_{12}$H$_{11}$Cl$_3$IN$_2$O$_2$: C, 32.21; H, 2.25; N, 6.26. Found: C, 32.13; H, 2.35; N, 5.86.

Compound 74: mp 167–168° C.; R$_f$ 0.14 (EtOAc/hexane 1:2); $^1$H-NMR (360 MHz, DMSO-d$_6$): δ8.77 (s, 1H), 8.11 (s, 1H), 5.38 (d, 1H, J=9.5 Hz), 4.97 (t, 1H, D$_2$O exchangeable), 4.75 (q, 1H), 4.36 (m, 1H), 3.56 (m, 1H), 3.47 (m, 1H), 2.76 (m, 1H), 2.33 (m, 1H); $^{13}$C-NMR (90 MHz, DMSO-d$_6$): δ141.99, 136.33, 130.15, 125.40, 119.22, 116.68, 114.53, 80.02, 79.02, 63.08, 39.52, 19.77. Anal. Calcd for C$_{12}$H$_{10}$Cl$_3$IN$_2$O$_2$: C, 32.21; H, 2.25; N, 6.26. Found: C, 32.40; H, 2.32; N, 6.10.

Compound 75: mp 199–200° C.; R$_f$ 0.17 (EtOAc/hexane 1:2); $^1$H-NMR (360 MHz, DMSO-d$_6$): δ9.01 (s, 1H), 8.09 (s, 1H), 5.34 (m, 1H D$_2$O exchangeable), 5.18 (d, 1H, J=11.3 Hz), 5.10 (m, 1H), 3.92 (m, 2H), 3.71 (m, 1H), 3.56 (m, 2H); $^{13}$C-NMR (90 MHz, DMSO-d$_6$): δ141.35, 135.18, 129.85, 125.24, 119.22, 118.54, 116.73, 74.22, 71.88, 65.94, 43.11, 24.02; HRMS m/z calcd for C$_{12}$H$_{11}$Cl$_2$IN$_2$O$_2$ 445.8853, found 445.8842. Anal. Calcd for Cl$_2$H$_{10}$Cl$_3$IN$_2$O$_2$: C. 32.21; H, 2.25; N, 6.26. Found: C. 32.02; H, 2.29; N, 5.99.

Compounds 76 and 77

2,6,7-Trichloro-3-(2',3'-dideoxy-2',3'-didehydro-β-D-ribofuranosyl) imidazo[1,2-a] pyridine (76) and 2,6,7-trichloro-3-(4'(S),5'-dihydroxy-1-oxo-pentane) imidazo[1,2-a]pyridine (77). To a solution of compound 73 (400 mg, 0.89 mmol) in dry DMF (10 mL) was added DBU (0.67 mL, 4.4 mmol) and the resulting solution stirred at 90° C. for 16 h. The reaction mixture was partitioned between water (50 mL) and CH$_2$Cl$_2$ (100 ML) and the phases separated. The organic phase was dried over magnesium sulfate, concentrated under reduced pressure and the resulting solid purified by flash chromatography (EtOAc/hexane 1:5, 15 cm×2 cm). Fractions containing a faster migrating minor product were pooled and concentrated in vacuo to give, after recrystallization from aqueous CH$_3$CN, 48 mg (15%) of compound 77 as a white powder. Fractions containing the slower migrating major product were subsequently combined and concentrated in vacuo to give, after recrystallization from aqueous CH$_3$CN, 170 mg (62%) of compound 76 as white powder.

Compound 76: mp 147–148° C.; R$_f$ 0.40 (EtOAc/hexane 1:2); $^1$H-NMR (360 MHz, DMSO-d$_6$): δ9.42 (d, 1H J=0.4Hz), 8.05 (d, 1H, J=0.4 Hz), 6.34 (m, 1H), 6.15 (m, 1H), 6.10 (m, 1H), 5.20 (t, 1H), 4.85 (m 1H), 3.70 (m, 2H); $^{13}$C-NMR (90 MHz, DMSO-d$_6$): δ141.75, 135.25, 132.76, 130.01, 127.18, 126.10, 118.55, 117.32, 116.28, 87.03, 76.92, 62.47. Anal. Calcd for C$_{12}$H$_9$Cl$_3$N$_2$O$_2$: C, 45.10; H, 2.84; N, 8.76. Found: C, 45.20; H, 2.89; N, 8.63. Structure and absolute stereochemistry of compound 76 was determined by X-ray crystallography.

Compound 45: mp 165–166° C.; R$_f$ 0.20 (EtOAc/hexane 1:2); $^1$H-NMR (360 MHz, DMSO-d$_6$): δ9.80 (s, 1H), 8.30 (s, 1H), 4.57 (d, 1H), 4.54 (t, 1H), 3.5 (m, 1H), 3.3 (m, 2H), 3.14 (m, 2H), 1.90 (m, 1H), 1.60 (m, 1H); $^1$H-NMR (360 MHz, CDCl$_3$): δ9.96 (s, 1H), 7.79 (s, 1H), 3.84 (m, 1H), 3.74 (m, 1H), 3.52 (m, 1H), 3.32 (t, 2H), 2.59 (d, 1H), 1.98 (m, 3H); $^{13}$C-NMR (90 MHz, DMSO-d$_6$): δ190.34, 143.65, 142.08, 133.97, 127.53, 121.54, 118.95, 116.83, 70.28, 65.77, 37.46, 27.74; HRMS m/z calcd for C$_{12}$H$_{11}$Cl$_3$N$_2$O$_3$ 335.9834, found 335.9823. Anal. Calcd for C$_{12}$H$_{11}$Cl$_3$N$_2$O$_3$·¼H$_2$O: C, 42.13; H, 3.39; N, 8.20. Found: C, 41.89; H 3.14; N, 8.05.

Compound 78

2,6,7-Trichloro-3-(β-D-ribofuranosyl)imidazo[1,2-a] pyridine (78). Compound 76 (70 mg, 0.22 mmol) was dissolved in a 4:1 mixture of acetone and water (5 mL), then N-methylmorpholine N-oxide (40 mg, 0.33 mmol) and osmium tetroxide (150 μL of 2.5% OsO$_4$ in tert-butanol) were added. After stirring at room temperature for 16 hours, sodium bisulfite (20 mL. concentrated aqueous solution) was added and the solution stirred for 1 h, then extracted with EtOAc (40 mL×3). The combined EtOAc extracts were dried (MgSO$_4$), filtered and concentrated under reduced pressure to give a solid which was purified by flash chromatography (EtOAc/hexane 2:1, 10 cm×2 cm). Fractions containing product were combined, concentrated to a solid and crystallized from CH$_3$CN to give 73 mg (95%) of compound 78 as a white solid.

Compound 78: mp 239–240° C.; R$_f$ 0.30 (EtOAc/hexane 2:1); [α]$_D^{20}$=−2.32.70° (MeOH); $^1$H-NMR (360 MHz, DMSO-d$_6$): δ9.45 (s, 1H), 8.06 (s, 1H), 5.41 (t, 1H,D$_2$O exchangeable), 5.13 (d, 1H, D$_2$O exchangeable), 5.10 (d, 1H, D$_2$O exchangeable), 5.02 (d, 1H, J=9.1 Hz, 1'-H), 4.30 (m, 1H), 4.10 (m, 1H), 3.95 (m, 1H), 3.6–3.7 (m, 2H); $^{13}$C-NMR (90 MHz, DMSO-d$_6$): δ141.77, 135.96, 129.61, 126.28, 118.85, 116.92, 116.49, 86.42, 74.55, 71.30, 70.99, 61.40; UV λ$_{max}$ (MeOH) 325 (1555), 245 (11652), 238 (9935), 229 (8194); (pH 11) 295 (8226), 243 (61612), 335 (58064), 230 (48710); (pH 1) 294 (12290), 236 (59225); HRMS m/z calcd for C$_{12}$H$_{11}$Cl$_3$N$_2$O$_4$ 351.9783, found 351.9771. Anal. Calcd for C$_{12}$H$_{11}$Cl$_3$N$_2$O$_4$: C, 40.73; H 3.14; N, 7.92. Found: C, 40.76; H 3.07; N, 7.89. Structure and absolute stereochemistry of compound 78 was determined by X-ray crystallography.

G. Preparation of the Imidazo[1,2-a]Pyridines C5-Nucleosides

Imidazo[1,2-a]pyridines C5-nucleosides may be prepared from imidazo[1,2-a]pyridines by condensation of a lithiated imidazo[1,2-a]pyridine with a lactone in a method analogous to that of Yasuo et al., European Patent 238 070, 1987.

Figure 7:
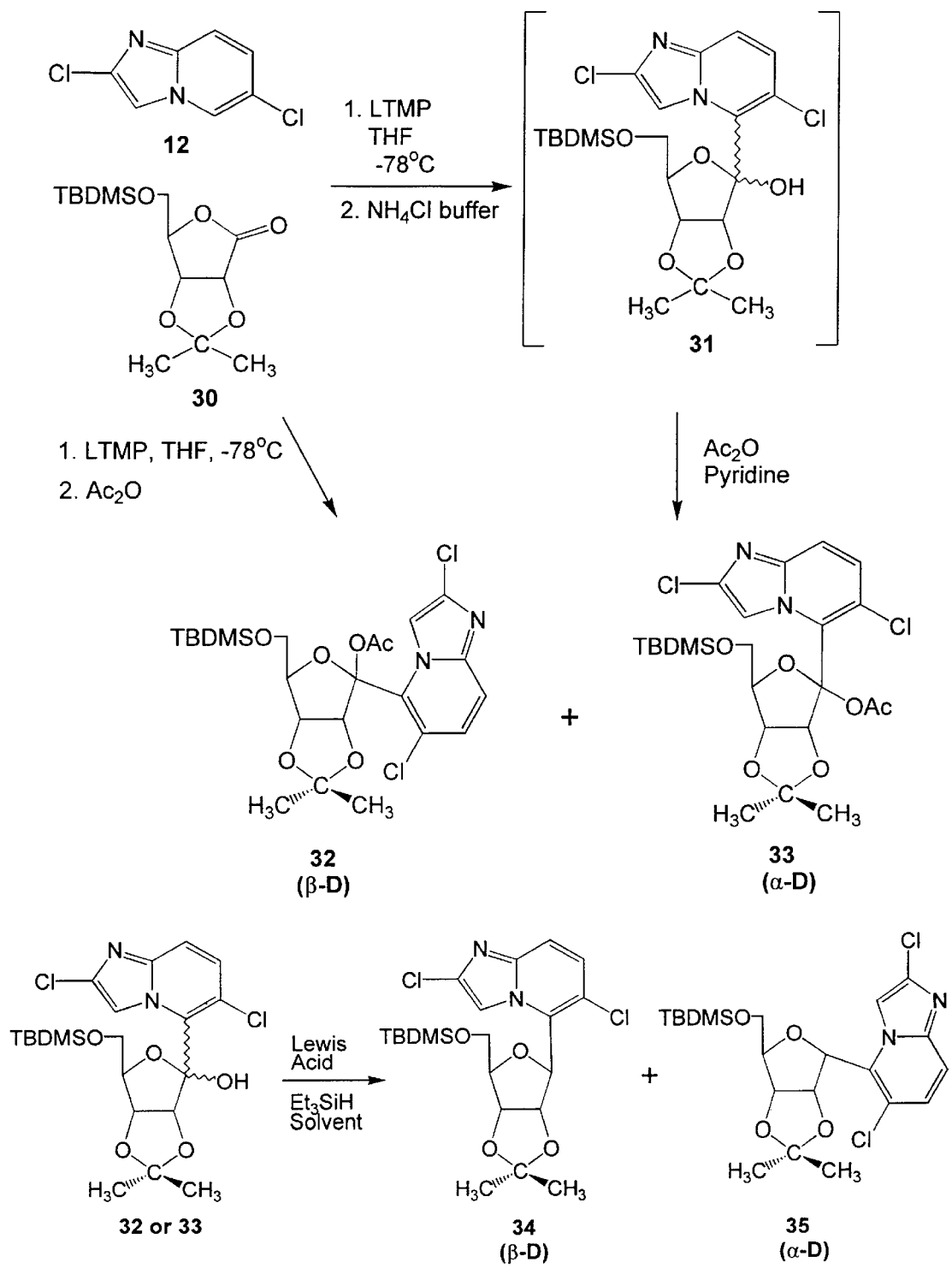
FIG. 7 is a flowchart illustrating a method for the chemical synthesis of various 2,6-dichloro-imidazo[1,2-a]pyridine C5-nucleosides.
Figure 8:
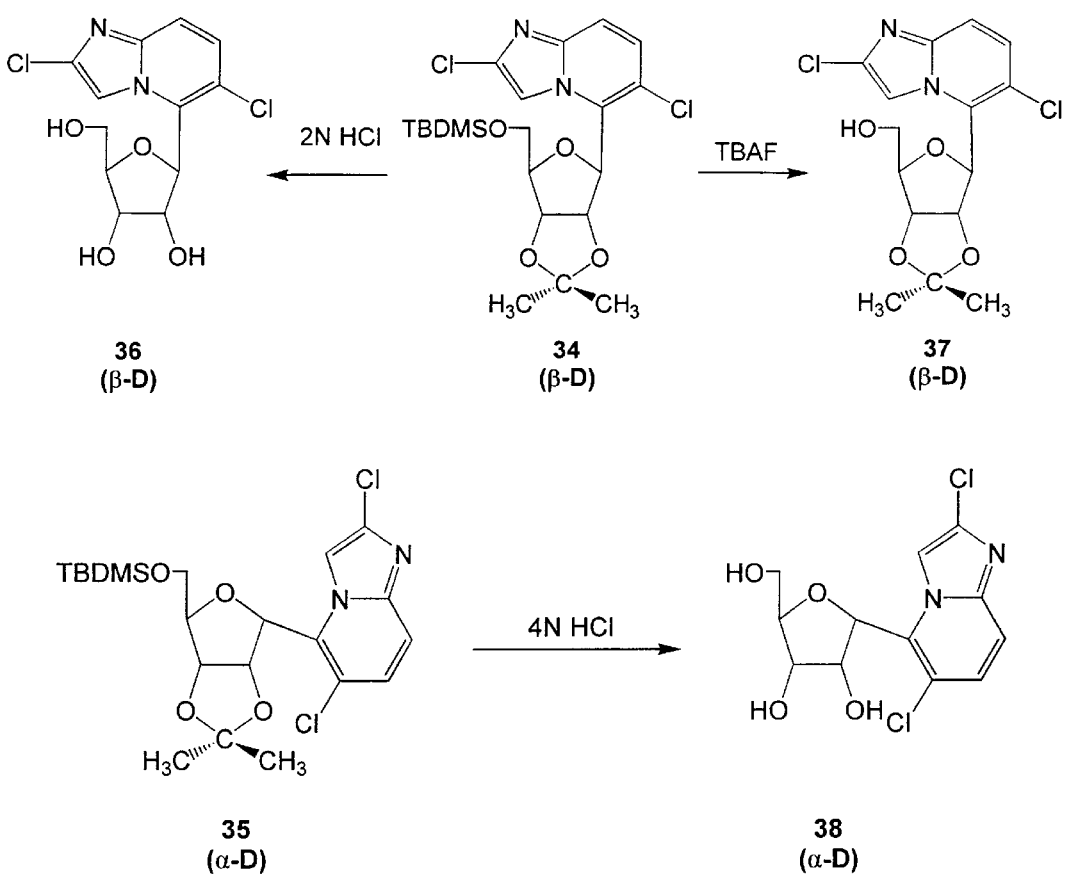
FIG. 8 is a flowchart illustrating a method for the chemical synthesis of various 2,6-dichloro-imidazo[1,2-a]pyridine C5-nucleosides.

The synthetic strategy used in the preparation of compounds 32, 33, 34, 35, 36, 37 and 38 is illustrated in FIG. 7 and FIG. 8. 2,6-dichloro-imidazo[1,2-a]pyridine (compound 12) was reacted with LTMP (a lithiating reagent) in tetrahydrofuran (i.e., THF) to form a lithiated intermediate, followed by reaction with a protected lactone (compound 30) and subsequent reaction with acetic anhydride (i.e., $CH_3C(=O)OC(=O)CH_3$) to yield a mixture of 2,6-dichloro-5-substituted-imidazo[1,2-a]pyridine isomers (compounds 32 and 33). Proton nuclear magnetic resonance ($^1$H-NMR) of the heterocyclic protons yielded two doublets with a coupling constant, J, of 10 Hz, and one singlet, confirming substitution at the C5 position. The isomers (compounds 32 and 33) were reacted with a Lewis acid, such as aluminum trichloride (i.e., $AlCl_3$) and triethylsilane (i.e., $Et_3SiH$) to remove the acetate group at the 1'-position, and further reacted with hydrochloric acid (i.e., HCl) to remove the isopropylidine protecting group and yield the β-D (compound 36) and α-D (compound 38) isomers of 2,6-dichloro-5-(ribofuranosyl)-imidazo[1,2-a]pyridine.

Compound 32

2,6-Dichloro-5-(5'-O-[(tert-butyl)dimethvlsilyl]-1'-acetoxy-2',3'-O-isopropylidene-β-D-ribofuranosyl) imidazo [1,2-a]pyridine (32). To a solution of 2,2,6,6-tetramethyl-piperidine (TMP, 0.47 mL, 2.8 mmol) in THF (15 mL) at 0° C. was added n-BuLi (1.6 mL, 2.6 mmol, 1.6 M solution in hexanes). This solution was stirred for 30 min at 0° C. and then cooled to −78° C. and a solution of 2,6-dichloro-imidazo[1,2-a]pyridine, compound 12 (0.4 g, 2.14 mmol) in THF (5 mL) was added dropwise over a period of 5 min. The resulting dark brown solution was stirred at −78° C. for 20 min. A solution of the lactone, compound 30 (0.85 g, 2.8 mmol) in THF (5 mL) was added dropwise over a period of 7 min and the resulting black reaction mixture was stirred at −78° C. for 30 min. The reaction mixture was poured into an $NH_4Cl$ buffer (100 mL). This aqueous solution was extracted with EtOEt (3×70 mL), the organic phase dried over magnesium sulfate and concentrated under reduced pressure to give compound 31 as a dark oil. This oil was purified by flash chromatography (EtOAc/hexane 1:5, 15 cm×4 cm) to give 830 mg (80%) of compound 31 as a syrup. Compound 31 (1.3 g, 2.7 mmol) was dissolved in dry pyridine (15 mL), and acetic anhydride (2.5 mL, 27 mmol) was added to this solution. The reaction mixture was stirred, under $CaSO_4$ protection from moisture, for 12 h and then poured into an ice-water mixture (120 mL). This mixture was subsequently extracted with EtOAc (3×80 mL), the combined organic extracts dried over magnesium sulfate and evaporated to dryness to give a white solid. This solid was purified by flash chromatography (EtOAc/hexane 1:5, 15 cm×4 cm) to give, after recrystallization from EtOH, 1.4 g (98%) of compound 32 as a white solid Compound 32: mp 165–166° C.; $R_f$ 0.45 (EtOAc/hexane 1:5); $^1$H-NMR (300 MHz DMSO-$d_6$): δ8.61 (s, 1H), 7.59 (d, 1H, J=9.5 Hz), 7.37 (d, 1H, J=9 Hz), 5.46 (d, 1H, 2'-H, J=5.6 Hz), 4.94 (d, 1H, 3'-H, J=5.6 Hz), 4.70 (t, 1H, 4'-H, J=7.1 Hz), 3.73 (d, 2H, 5'H J=7.1 Hz), 2.02 (s, 3H), 1.22 (s, 3H), 0.84–0.91 (m, 12H), 0.12 (two s, 6H). Anal. Calcd for $C_{23}H_{32}Cl_2N_2O_6Si$: C, 51.98; H, 6.07; N, 5.27; Found: C, 52.30; H, 5.98; N, 5.34.

Compound 33

2,6-Dichloro-5-(5'-O-[(tert-butyl)dimethylsilyl]-1'-acetoxy-2',3'-O-isopropylidene-α-D-ribofuranosyl) imidazo [1,2-a]pyridine (33). To a solution of 2,2,6,6-tetramethyl-piperidine (TMP, 1.0 mL, 5.6 mmol) in THF (15 mL) at 0° C. was added n-BuLi (3.2 mL. 5.2 mmol, 1.6 M solution in hexanes). This solution was stirred for 20 min at 0° C. and then cooled to −78° C. A solution of 2,6-dichloro-imidazo [1,2-a]pyridine, compound 12 (0.8 g, 4.28 mmol) in THF (10 mL) was then added dropwise to the above solution over a period of 5 min. The resulting dark brown solution was stirred at −78° C. for 20 min. A solution of the lactone, compound 30 (1.7 g, 5.6 immol) in THF (10 mL) was then added dropwise over a period of 10 min and the resulting black reaction mixture was stirred for 30 min at −78° C. Acetic anhydride (2 mL, 20 mmol) was added dropwise to the reaction mixture and the mixture stirred at −78° C. for additional 30 min. The reaction mixture was then poured into an $NH_4Cl$ buffer (150 mL). This mixture was extracted with EtOAc (3×100 mL), the organic phase dried over magnesium sulfate and concentrated under reduced pressure to give a yellowish oil which was purified by flash chromatography (Toluene/EtOAc 20:1), 15 cm×5 cm), to give 1.5 g (65%) of compound 33 the as a clear syrup and 0.23 g (10%) of compound 32.

Compound 33: $R_f$ 0.14 (Toluene/EtOAc 20:1); $^1$H-NMR (360 MHz, DMSO-d6): δ8.55 (s, 1H), 7.57 (d, 1H, J=9.4 Hz), 7.35 (d, 1H, J=9.4 Hz), 4.95 (d, 1H, 3'-H, J=5.5 Hz), 4.69–4.72 (m, 2H, 2'-H and 4'-H), 3.87 (dd, 1H, 5'-H, J=2.2 Hz and J=11.5 Hz), 3.74 (dd, 1H, 5'-H, J=2.2 Hz and J=11.5 Hz), 2.04 (s, 3H), 1.65 (s, 3H), 1.37 (s, 3H), 0.59(s, 9H), −0.18 (s, 3H), −0.30 (s, 3H). Anal. Calcd for $C_{23}H_{32}Cl_2N_2O_6Si$: C, 51.98; H, 6.07; N, 5.27; Found: C, 52.31; H, 6.08; N, 5.35.

Compounds 34 and 35

2,6-Dichloro-5-(5'-O-[(tert-butyl)dimethylsilyl]-2',3'-O-isopropylidene-β-D-ribofuranosyl)imidazo[1,2-a]pyridine (34)

2,6-dichloro-5-(5'-O-[(tert-butyl)dimethylsilyl]-2',3'-O-isopropylidene-α-D-ribofuranosyl)imidazo[1,2-a]pyridine (35)

Method A. Compound 33 (1.05 g, 2 mmol) was placed in a flask, activated 4A molecular sieves (600 mg) and dry $CH_2Cl_2$ (5 mL) were added and this mixture was cooled to 0° C. in an ice bath under argon atmosphere. To this mixture was added consecutively $Et_3SiH$ (3.2 mL, 20 mmol) and TMSOTf (0.96 mL, 5 mmol). The reaction mixture was allowed to warm to room temperature and stirred at room temperature for 30 min. Triethylamine (2 mL) was then added to neutralize the reaction mixture, it was diluted with $CH_2Cl_2$ and filtered through Celite. The organic phase was then extracted with water (2×50 mL) and concentrated. The resulting residue was purified by flash chromatography (EtOAc/hexane 1:5, 15 cm×5 cm) to give a 730 mg (78%) of compound 34 as a white foam.

Method B. Compound 33 (1.27 g, 2.4 mmol) was placed in a flask under argon and $Et_3SiH$ (7.5 mL, 48 mmol) was added. The solution was cooled to 0° C. in an ice bath and $BF_3.OEt_2$ (0.74 mL, 6.0 mmol) was added. The reaction was stirred under argon atmosphere at room temperature for 4 h.

Saturated NaHCO$_3$ (40 mL) was added to neutralize the reaction mixture and it was extracted with CH$_2$Cl$_2$ (3×50 mL), the organic phase dried over magnesium sulfate, filtered and concentrated. The resulting residue was purified by flash chromatography (EtOAc/hexane 1:5, 15 cm×2 cm) to give 400 mg (35%) of 34 and 385 mg (34%) of 35 both as white foams.

Compound 34: R$_f$ 0.26 (EtOAc/hexane 1:5); $^1$H-NMR (360 MHz, DMSO-d$_6$): δ8.18 (s, 1H), 7.46 (d, 1H, J=7.8 Hz), 7.22 (d, 1H J=7.8 Hz), 5.66 (d, 1H, 1'-H, J=6.3 Hz), 4.98 (m, 2H), 4.27 (m, 1H), 4.08 (dd, 1H, J=1.8 Hz, J=11.7Hz), 3.99 (dd, 1H J=1.8Hz, J=11.7 Hz), 1.67 (s, 3H, acetyl), 1.37 (s, 3H, acetyl), 0.99 (s, 9H), 0.21 (s, 3H), 0.22 (s, 3H); Anal. Calcd for C$_{21}$H$_{30}$Cl$_2$N$_2$O$_4$Si: C, 53.27; H, 6.38; N, 5.92; Found: C, 53.48; H, 6.29; N, 6.27.

Compound 35: R$_f$ 0.20 (EtOAc/hexane 1:5); $^1$H-NMR (360 MHz, DMSO-d$_6$): δ8.30 (s, 1H), 7.44 (d, 1H, J=9.4 Hz), 7.18 (d, 1H, J=9.4 Hz), 6.06 (d, 1H, 1'-H, J=4.7 Hz), 5.11 (dd, 1H), 4.99 (d, 1H), 4.56 (t, 1H), 4.08 (dd, 1H), 3.98 (dd, 1H), 1.31 (s, 3H. acetyl), 1.30 (s, 3H, acetyl), 0.97 (s, 9H), 0.13 (S, 6H). Anal. Calcd for C$_{21}$H$_{30}$Cl$_2$N$_2$O$_2$Si: C, 53.27; H, 6.38; N, 5.92; Found: C, 53.03; H, 6.42; N, 5.77.

Compound 36

2,6-Dichloro-5-(β-D-ribofuranosyl)imidazo[1,2-a] pyridine (36). Compound 34 (730 mg, 1.5 mmol) was dissolved in THF (30 mL), and to this solution was added 2N HCl (30 mL). This reaction mixture was stirred at room temperature for 8 h. Solid Na$_2$CO$_3$ was then added in portions to the mixture until it became basic to litmus (pH 8). The resulting mixture was extracted with EtOAc (3×80 mL), the organic phase dried over magnesium sulfate, filtered and concentrated. The residue was purified by flash chromatography (EtOAc/hexane 2:1, 15 cm×5 cm) to give, after recrystallization from MeOH, 470 mg (98%) of compound 36 as a white crystalline solid.

Compound 36: mp 232–233° C.; R$_f$ 0.36 (EtOAc/hexane 2:1); $^1$H-NMR (360 MHz, DMSO-d$_6$): δ8.80 (s, 1H), 7.60 (d, 1H, J=9.5 Hz), 7.44 (d, 1H, J=9.5 Hz), 5.43 (m, 2H, simplifies on D$_2$O exchange to d, 1H 1'-H, J=9.0 Hz), 5.21 (d, 1H, D$_2$O exchangeable), 5.14 (d, 1H, D$_2$O exchangeable), 4.38 (m, 1H), 4.16 (m, 1H), 3.97 (m, 1H), 3.71 (m, 2H); $^{13}$C-NMR (90 MHz DMSO-d$_6$): δ142.53 (C8a), 134.73 (C2), 131.35 (C5), 127.19 (C7), 121.07 (C6), 116.87 (C8), 111.12 (C3), 87.41, 77.97, 70.32, 69.80, 60.66; UV λ$_{max}$ (ethanol) 294 (5573), 233 (22020); (pH 11) 276 (13800), 232 (37342), (pH 1) 294 (8400), 226 (24800); HRMS m/z calcd for C$_{12}$H$_{12}$Cl$_2$N$_2$O$_4$ 318.0174, Found 318.0169. Anal. Calcd for C$_{12}$H$_{12}$Cl$_2$N$_2$O$_4$: C, 45.16; H, 3.79; N, 8.78; Found: C, 45.06; H, 3.87; N, 8.39.

Compound 37

2,6-Dichloro-5-(2',3'-di-O-isopropylidene-β-D-ribofuranosyi)imidazo[1,2-a]pyridine (37). Compound 34 (240 mg, 0.5 mmol) was dissolved in THF (5 mL) and treated with a solution of TBAF in THF (0.5 mL, 1.0 mmol, 2N in THF). The reaction mixture was stirred for 1 h, water (50 mL) was added to the reaction mixture and the mixture extracted with EtOAc (3×70 mL). The combined organic extracts were dried over magnesium sulfate, filtered and the filtrate concentrated. The residue was purified by flash chromatography (EtOAc/hexane 2:1, 15 cm×2 cm) to give, after recrystallization from MeOH, 160 mg (89%) of 37 as a white crystalline solid.

Compound 37: mp 250° C. (dec); R$_f$ 0.65 (EtOAc/hexane 2:1); $^1$H-NMR (360 MHz, DMSO-d$_6$): δ8.56 (s, 1H), 7.64 (d, 1H J=9.5 Hz), 7.45 (d, 1H J=9.5 Hz), 5.52 (m, 2H simplifies on D$_2$O exchange to give d, 1H, 1'-H, J=5.6 Hz), 5.00 (m, 2H), 4.20 (m, 1H), 3.76 (m, 2H), 1.56 (s, 3H, acetyl), 1.29 (s, 3H, acetyl). Anal. Calcd for C$_{15}$H$_{16}$Cl$_2$N$_2$O$_4$: C, 50.16; R 4.49; N, 7.80; Found: C, 49.96; H, 4.54; N, 7.49.

Compound 38

2,6-Dichloro-5-(α-D-ribofuranosyl)imidazo[1,2-a] pyridine (38). Compound 35 (350 mg, 0.7 mmol) was dissolved in THF (20 mL), and to this solution were added 4N HCl (20 mL). This reaction mixture was stirred at room temperature for 24 hr. Solid Na$_2$CO$_3$ was then added in portions to the mixture until it became basic to litmus (pH 8). The resulting mixture was extracted with EtOAc (3×80 mL), the organic phase dried over magnesium sulfate, filtered and concentrated. The residue was purified by flash chromatography (EtOAc/hexane 2:1, 15 cm×5 cm) to give, after recrystallization from MeOH, 212 mg (90%) yield of 38 as a white crystalline solid.

Compound 38: mp 245–246° C.; R$_f$ 0.30 (EtOAc/hexane 2:1); $^1$H-NMR (360 MHz, DMSO-d$_6$): δ8.09 (s, 1H), 7.56 (d, 1H J=9.5 Hz), 7.39 (d, 1H, J=9.5 Hz), 5.65 (d, 1H, 1'-H, J=3.2 Hz), 5.39 (d, 1H D$_2$O exchangeable), 5.16 (d, 1H, D$_2$O exchangeable), 4.87 (t, 1H, D$_2$O exchangeable), 4.31 (m, 1H), 4.25 (m, 1H), 4.11 (m, 1H), 3.74 (m, 1H), 3.55 (m, 1H); $^{13}$C-NMR (90 MHz, d$_6$-DMSO): δ142.74 (C8a), 133.55 (C2), 132.40 (C5), 126.76 (C7), 118.75 (C6), 116.15 (C8), 111.64 (C3), 82.59, 79.49, 74.00, 71.40, 61.24- UV λ$_{max}$. (ethanol) 294 (5573), 233 (22020); (pH 11) 276 (13800), 232 (37342); (pH 1) 294 (8400), 226 (24800). Anal. Calcd for C$_{12}$H$_{12}$C$_{12}$N$_2$O$_4$: C, 45.161H, 3.79; N, 8.78; Found: C 44.95; H, 3.93; N, 8.65.

Figure 9:
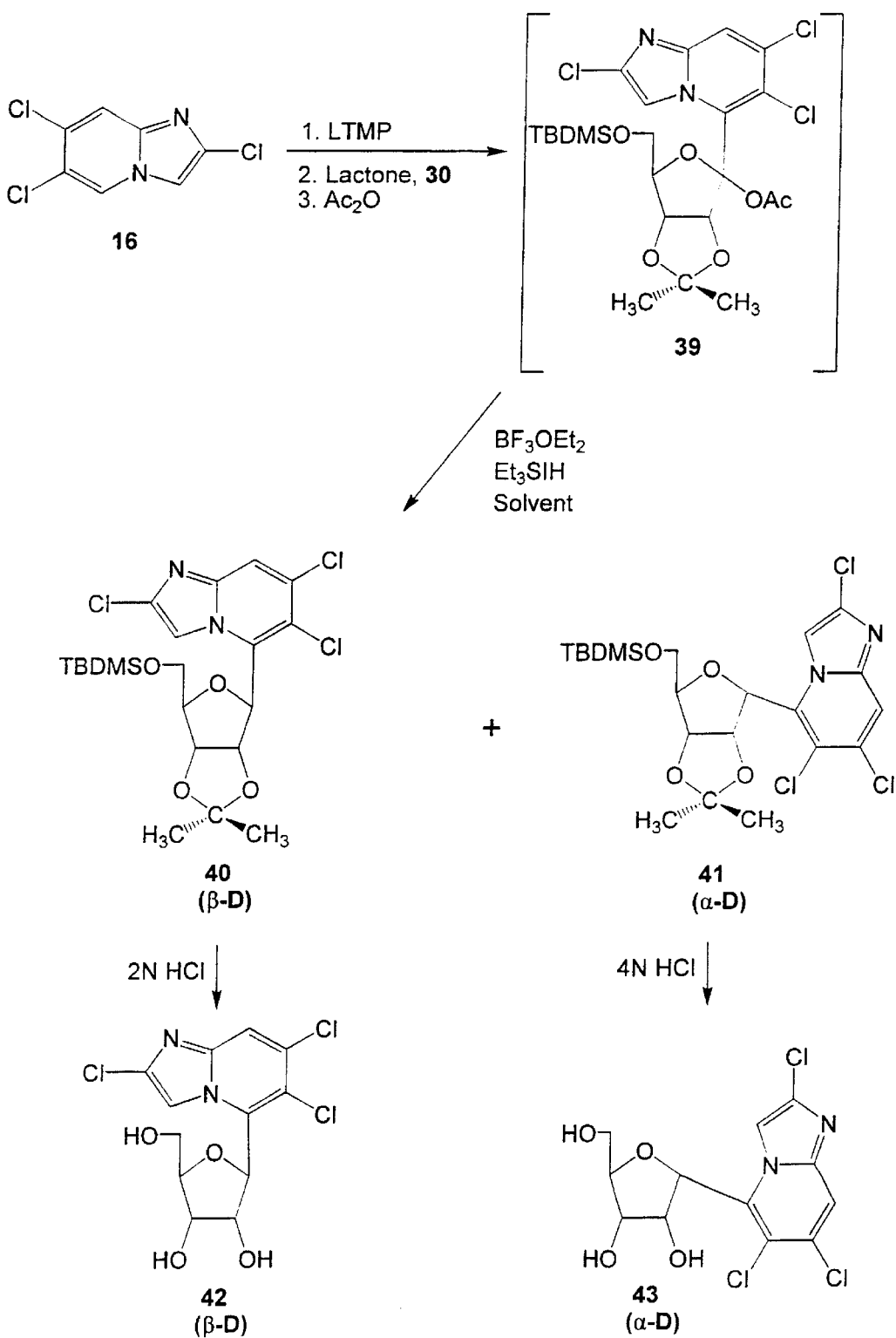
FIG. 9 is a flowchart illustrating a method for the chemical synthesis of various 2,6,7-trichloro-imidazo[1,2-a]pyridine C5-nucleosides.

The synthetic strategy used in the preparation of compounds 40, 41, 42, and 43 is illustrated in FIG. 9. This method is similar to that illustrated in FIGS. 7 and 8. 2,6,7-trichloro-imidazo[1,2-a]pyridine yields the α-D (compound 43) and β-D isomers (compound 42) of 2,6,7-trichloro-5-(ribofuranosyl)-imidazo[1,2-a]pyridine.

Compounds 40 and 41

2,6,7-Trichloro-5-(5'-O-[(tert-butyl)dimethylsilyl]-2',3'-O-isopropylidene-β-D-ribofuranosyl)imidazo[1,2-a] pyridine (40)

2,6,7-Trichloro-5-(5-O-[(tert-butyl)dimethylsilyl]-2',3'-O-isopropylidene-α-D-ribofuranosyl)imidazo[1,2-a] pyridine (41)

To a solution of TMP (1.0 mL, 5.9 mmol) in THF (15 mL) at 0° C. was added n-BuLi (3.4 mL. 5.4 mmol, 1.6 M solution in hexanes). This solution was stirred for 30 min at 0° C. and then cooled to −78° C. and a solution of 2,6,7-trichloro-imidazo[1,2-a]pyridine, compound 16 (1.0 g, 4.51 mmol) in THF (10 mL) was added dropwise over a period of 5 min. The resulting dark, brown solution was stirred at −78° C. for 20 min. A solution of the lactone, compound 30 (1.4 g, 4.5 mmol) in THF (10 mL) was then added dropwise over a period of 10 min and the resulting black reaction mixture was stirred for 30 min at −78° C. Acetic anhydride (4 mL, 40 mmol) was added dropwise to the reaction mixture and the mixture stirred at −78° C. for an additional 1 hr. The reaction mixture was poured into an NHCl buffer (150 mL) and extracted with EtOAc (3×100 mL). The organic phase was dried over magnesium sulfate. The EtOAc was removed under reduced pressure to give a yellowish oil which was purified by flash chromatography (EtOAc/hexane 1:5, 15 cm×4 cm) to give 2.1 g (83%) of compound 39 as a syrup. Compound 39 (770 mg, 1.4 mmol) was placed in a flask, under argon, dissolved in CH$_2$Cl$_2$ (20 mL), and to this solution was added consecutively Et$_3$SiH (4.5 mL, 28 mmol) and BF$_3$.OEt$_2$ (0.43 mL, 3.5 mmol). The reaction was stirred under argon atmosphere at room temperature for 4 hr. Saturated NaHCO$_3$ (40 mL) were then added and the resulting mixture was extracted with CH$_2$Cl$_2$ (3×50 mL). The combined organic extracts were dried over magnesium sulfate, filtered and concentrated. The resulting residue was purified by flash chromatography (EtOAc/hexane 1:5, 15 cm×2 cm) to give 410 mg (58%) of compound 40 as a white solid. When the reaction was run according to Procedure B as described for compound 34, 200 mg (29%) of compound 40 was obtained as white crystals and 170 mg (25%) of compound 41 as a foam was obtained.

Compound 39: R$_f$ 0.47 (EtOAc/hexane 1:5); $^1$H-NMR (360 MHz, CDCl$_3$): δ8.49 (s, 1H), 7.65 (s, 1H), 4.91 (d, 1H, J=5.5 Hz), 4.68 (m, 2H), 3.95 (d, 1H, J=11.4 Hz), 3.70 (d, 1H, J=11.4 Hz), 2.09 (s, 3H), 1.71 (s, 3H acetyl), 1.40 (s, 3H, acetyl), 0.62 (s, 9H), −0.13 (s, 3H), −0.29 (s, 3H).

Compound 40: mp 142–143° C.; R$_f$ 0.46 (EtOAc/hexane 1:5); $^1$H-NMR (360 MHz CDCl$_3$): δ8.22 (s, 1H), 7.67 (s, 1H), 5.74 (d, 1H, 1-H, J=6.6 Hz), 4.97 (m, 2H), 4.27 (m, 1H), 4.07 (dm, 1H), 3.98 (dm, 1H), 1.67 (s, 3H, acetyl), 1.37 (s, 3H, acetyl), 0.99 (s, 9H), 0.22 (s, 3H), 0.21 (s, 3H); HRMS m/z calcd for C$_{21}$H$_{29}$Cl$_3$N$_2$O$_4$Si 506.0962, Found 506.0964. Anal. Calcd for C$_{21}$H$_{29}$Cl$_3$N$_2$O$_4$Si: C, 49.66; H, 5.76; N, 5.52; Found: C, 49.55; H, 5.73; N, 5.63.

Compound 41: R$_f$ 0.42 (EtOAc/hexane 1:5); $^1$H-NMR (360 MHz. CDCl$_3$): δ8.30 (s, 1H), 7.63 (s, 1H), 6.11 (d, 1H, 1'-H, J=4.7 Hz), 5.14 (t, 1H), 4.99 (d, 1H), 4.57 (m, 1H), 3.90 (m, 2H), 1.29 (s, 3H, acetyl), 1.28 (s, 3H, acetyl), 0.97 (s, 9H), 0.13 (s, 6H). Anal. Calcd. for C$_{21}$H$_{29}$Cl$_3$N$_2$O$_4$Si.½H$_2$O: C, 48.79; H, 5.85; N, 5.42; Found: C, 49.09; H 5.63; N, 5.08.

Compound 42

2,6,7-Trichloro-5-(β-D-ribofuranosyl)imidazo[1,2-a]pyridine (42). Compound 40 (150 mg, 0.3 mmol) was dissolved in THF (5 mL), and treated with 2N HCl (5 mL) as described for deprotection of compound 34. After purification by flash chromatography (EtOAc/hexane 2:1, 15 cm×2 cm) and recrystallization from MeOH, 100 mg (99%) of compound 42 was obtained as a white crystalline solid.

Compound 42: mp 270–271° C.; R$_f$ 0.34 (EtOAc/hexane 2:1); $^1$H-NMR (360 MHz, DMSO-d$_6$): δ8.87 (s, 1H), 8.07 (s, 1H), 5.55 (d, 1H, J=8.9 Hz, 1'-H), 5.46 (t, 1H, J=4.5 Hz, D$_2$O exchangeable), 5.26 (d, 1H, J=6.7 Hz, D$_2$O exchangeable), 5.18 (d, 1H, J=4.5 Hz, D$_2$O exchangeable), 4.36 (m, 1H), 4.16 (m, 1H), 3.99 (m, 1H), 3.73 (m, 2H); $^{13}$C-NMR (90 MHz, DMSO-d$_6$): δ141.73 (C8a), 135.50 (C3), 133.23 (C2), 129.77 (C7), 119.70 (C6), 116.32 (C8), 111.23 (C3), 87.63, 78.83, 70.36, 70.27, 60.56; UV λ$_{max}$ (ethanol) 300 (4464), 245 (25724), 238 (25280), 227 (25944); (pH 11) 298 (3957), 243 (20214), 237 (82044); (pH 1) 297 (7154), 236 (22472); HRMS m/z calcd for C$_{12}$H$_{12}$Cl$_2$N$_2$O$_4$ 351.9784, found 351.9801. Anal. Calcd for C$_{12}$H$_{12}$Cl$_2$N$_2$O$_4$: C, 40.76; H, 3.14; N, 7.92; Found: C, 40.43; H 3.21; N, 7.65.

Compound 43

2,6,7-Trichloro-5-(α-D-ribofuranosyl)imidazo[1,2-a]pyridine (43). Compound 41 (130 mg, 0.2 mmol) was dissolved in THF (5 mL), and treated with 4N HCl (10 mL) as described for deprotection of compound 35. After purification by flash chromatography (EtOAc/hexane 2:1, 15 cm×2 cm) and recrystallization from aqueous MeOH, 80 mg (88%) of compound 43 was obtained as a white crystalline solid.

Compound 43: mp 267–268° C.; R$_f$ 0.34 (EtOAc/hexane 2:1); $^1$H-NMR (360 MHz DMSO-d$_6$): δ8.13 (s, 1H), 8.01 (s, 1H), 5.73 (d, 1H, J=3.4 Hz, 1'-H), 5.42 (d, 1H D$_2$O exchangeable), 5.16 (d, 1H, D$_2$O exchangeable), 4.88 (t, 1H, D$_2$O exchangeable), 4.37 (m, 1H), 4.24 (m, 1H), 4.13 (m, 1H), 3.75 (m, 1H), 3.55 (m, 1H); $^{13}$C-NMR (90 MHz, DMSO-d$_6$): δ142.05 (C8a), 134.45 (C2 and C5),129.33 (C7), 117.23 (C6), 115.43 (8), 111.51 (C3), 82.77, 80.45, 73.71, 71.23, 61.20; UV λ$_{max}$ (ethanol) 300 (4450), 245 (23212), 238 (23044), 228 (22756); (pH 11) 298 (4655), 243 (23696), 237 (23277); (pH 1) 298 (7169), 236 (23277); HRMS m/z calcd for C$_{12}$H$_{12}$Cl$_2$N$_2$O$_4$ 351.9784, found 351.9772. Anal. Calcd for C$_{12}$H$_{12}$Cl$_2$N$_2$O$_4$ 0½H$_2$O: C, 39.75; H, 3.34; N, 7.73; Found: C, 39.79; H, 3.35; N, 7.42.

Figure 10:
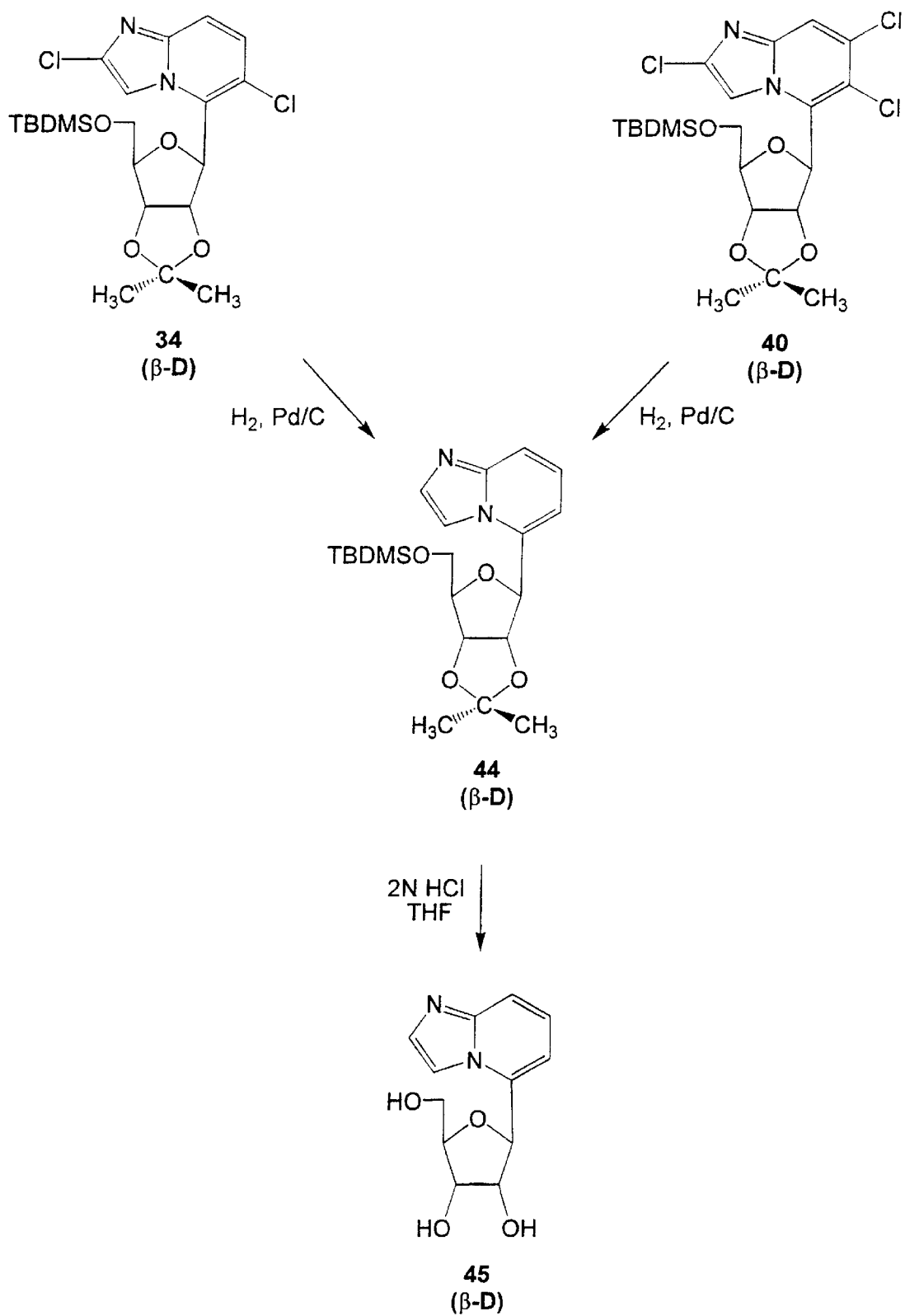
FIG. 10 is a flowchart illustrating a method for the chemical synthesis of various imidazo[1,2-a]pyridine C5-nucleosides.

The synthetic strategy used in the preparation of compounds 44 and 45 is illustrated in FIG. 10. Dechlorination of the β-D-isomers of 2,6-dichloro-5-substituted-imidazo[1,2-a]pyridine (compound 34) and 2,6,7-trichloro-5-substituted-imidazo[1,2-a]pyridine using palladium over charcoal (i.e., Pd/C) with hydrogen (i.e., H$_2$) followed by removal of the isopropylidene protecting group by reaction with 2 N hydrochloric acid (ie., HCl) yielded the same compound (compound 45).

Compound 44

5-(5'-O-[(tert-Butyl)dimethylsilyl]-2',3'-O-isopropylidene-β-D-ribofuranosyl)-imidazo[1,2-a]pyridine (44). Compound 34 (250 mg, 0.47 mmol) was dissolved in EtOH (25 mL). To this solution were added Et$_3$N (2 mL) and 5% Pd/C (150 mg). The resulting mixture was stirred under 1 atm of H$_2$ for 3 h. The reaction mixture was filtered through Celite and the filtrate evaporated to dryness under reduced pressure. The resulting syrup was purified by flash chromatography (EtOAc/hexane 1:2, SiO2) to give 110 mg (58%) of compound 44 as a syrup.

Compound 44: R$_f$ 0.19 (EtOAc/hexane 1:5); $^1$H-NMR (360 MHz, CDCl$_3$): δ7.88 (d, 1H J=1.2 Hz), 7.65 (d, 1H J=1.2 Hz), 7.58 (d, 1H J=9.0 Hz), 7.16 (q, 1H J=6.9 Hz, J=9.0 Hz), 7.00 (d, 1H, J=6.9 Hz), 5.09 (d, 1H, J=4.8 Hz, 1'-H), 4.82 (m, 1H), 4.67 (m, 1H), 4.32 (m, 1H), 3.92 (dd, 1H, J=3.2 Hz, J=11.3 Hz), 3.84 (dd, 1H, J=3.2 Hz, J=11.3 Hz), 1.66 (s, 3H, methyl), 1.36 (s, 3H, methyl), 0.85 (s, 9H), 0.07 (s, 3H), 0.06 (s, 3H); $^{13}$C-NMR (90 MHz, CDCl$_3$): δ146.14, 135.93, 134.08, 124.08, 117.04, 114.86, 111.05, 109.54, 85.32, 83.67, 83.51, 81.77, 63.27, 27.71, 25.98, 25.60, 18.42, −5.25, −5.41. Anal. Calcd for C$_{21}$H$_{32}$N$_2$O4Si: C, 62.34; H, 7.97; N, 6.92; Found: C, 62.36; H, 8.22; N, 6.84.

Compound 45

5-(β-D-Ribofuranosyl)imidazo[1,2-a]pyridine (45). Compound 44 (250 mg, 0.6 mmol) was dissolved in THF (5 mL). To this solution was added 2N HCl (5 mL) and the reaction mixture was stirred at room temperature for 8 h. The reaction mixture was neutralized by the addition of IRA-47 (OH). The resin was removed by filtration and the filtrate was evaporated to dryness. The resulting solid was purified by flash chromatography (EtOAc/hexane 2:1, 15 cm×2 cm) to give, after recrystallization from EtOH, 80 mg (54%) of 45 as a white solid.

Compound 45: mp 145–146° C.; R$_f$ 0.3 (EtOAc/hexane 2:1); $^1$H-NMR (360 MHz, DMSO-d$_6$): δ8.06 (d, 1H, J=1.0

Hz), 7.64 (d, 1H J=1.0 Hz), 7.54 (d, 1H, J=8.9 Hz), 7.27 (q, 1H, J=8.9 Hz, J=6.9 Hz), 7.10 (d, 1H, J=6.9 Hz), 5.45 (d, 1H, J=5.8 Hz, $D_2O$ exchangeable), 5.11 (d, 1H, J=2.5 Hz, $D_2O$ exchangeable), 5.02 (t, 1H, $D_2O$ exchangeable), 4.97 (d, 1H, J=5.6 Hz, 1'-H), 4.08 (m, 1H), 3.96 (m, 2H), 3.70 (dd, 1H J=12.0 Hz), 3.61 (dd, 1H, J=12.0 Hz); $^{13}$C-NMR (90 MHz, DMSO-d6): δ145.11 (C8a), 137.06 (C5) 133.29 (C2), 124.15 (C7), 115.98 (C8), 111.25 (C3), 109.67 (C6), 84.50, 80.64, 73.10, 70.65. 61.02, UV $\lambda_{max}$ (ethanol) 301 (4250), 280 (4742), 225 (11671); (pH 11) 279 (4188), 225 (13524); (pH 1) 281 (8604), 214 (18375); HRMS m/z calcd for $C_{12}H_{14}N_2O_4$ 250.0954, found 250.0957; Anal. Calcd for $C_{12}H_{14}N_2O_4 \cdot \frac{1}{2}H_2O$: C, 55.59; H, 5.83; N, 10.80 Found: C, 55.91; H, 5.97; N, 10.40

H. Assays for Antiviral Activity and Cytotoxicity
Cells and Viruses

KB cells (available from the American Type Culture Collection (ATCC) 12301 Parklawn Drive, Rockport, Md. 20852 (ATCC CCL 17)), an established human cell line derived from an epidermal oral carcinoma, were grown in minimal essential medium (MEM) (Sigma) with Hanks salts (MEM(H)) supplemented with 5% fetal calf serum. Human foreskin fibroblasts (HFF cells) (provided by the University of Michigan Hospital) and African green monkey kidney cells (BSC-1) (ATTC CCL 26) cells were grown in MEM with Earl salts (MEM(E)) supplemented with 10% fetal bovine serum. Cells were passaged according to conventional procedures and as described in Shipman, C., Jr. et al. (1976) Antimicrob. Agents Chemother. Vol. 9:120 and incorporated herein by reference. Briefly, cells were passaged at 1:2 to 1:10 dilutions according to conventional procedures by using 0.05% trypsin plus 0.02% EDTA in a HEPES buffered salt solution. HFF cells were passaged onlv at 1:2 dilutions.

CEM cells and strain $III_B$ of HIV-1 were obtained through courtesy of Dr. Louis S. Kurcera, Boman Gray School of Medicine, Wake Forest University. CEM cells were grown in suspension culture and passaged through conventional procedures.

A plaque purified isolate, $P_o$, of the Towne strain of HCMV was used in all experiments and was a gift of Dr. Mark Stinski, University of Iowa. The KOS strain of HSV-1 was used and was provided by Dr. Sandra K. Weller, University of Connecticut. Stock preparations of HCMV and HSV-1 were prepared and titered as known to those of skill and the art and described in Turk, S. R. et al. (1987) Antimicrob. Agents Chemother. Vol. 31:544–550 and Shipman, C., Jr., et al. (1990) J. Virol. Methods Vol. 28:101–106, each incorporated herein by reference.

Briefly, high titer HSV-1 stocks were prepared as follows. Nearly confluent monolayer cultures of KB cells were grown in 32 oz. glass bottles containing MEM(E) buffered with 25 mM HEPES and supplemented with 5% fetal bovine serum and 0.127 giliter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min.). The resulting virus pools were stored at −760C until retrieved for use in experiments.

HSV-1 was titered using monolayer cultures of BSC-1 cells. Cells were planted at $3 \times 10^5$ cells/well using 6-well cluster dishes. MEM(E) supplemented with 10% fetal bovine serum was employed as medium. After 22–24 h, cells were 90% confluent and were inoculated in triplicate using at least three ten-fold dilutions with 0.2 ml of the virus suspension to be assayed and incubated in a humidified 4% $CO_2$–90% air atmosphere for one hour to permit viral adsorption. Following virus adsorption, the cell sheet was overlayed with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

Stock HCMV was prepared by infecting HFF cells at a multiplicity of infection (m.o.i.) of less that 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HCMV was titered in 24-well cluster dishes which were plated to contain $5 \times 10^4$ HFF cells/well, grown as described above. When the cells were 70 to 80% confluent, 0.2 ml of the virus suspension was added per well and adsorbed as described above. At least three ten-fold dilutions of each preparation were used. Following virus adsorption, the cell sheets were overlayed with 0.5% methocel (4000 CPS) in maintenance medium [MEM(E) with 1.1 g/liter $NaHCO_3$, 100 units/ml penicillin G, 100 μg/ml streptomycin, and 5% fetal bovine serum]. The cultures were incubated in a humidified atmosphere of 4% $CO_2$–96% air. Viral plaques were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

Assays for Antiviral Activity

HCMV plaque reduction experiments were performed with monolayer cultures of HFF cells by a procedure similar to that referenced above for titration of the viruses and described in Devivar, R. V. et al. (1994) J. Med. Chem. Vol. 37:2942–2949. Activity of compounds against HSV-1 was evaluated using an ELISA assay.

The effect of compounds of the replication of HCMV was measured using a plaque (focus) reduction assay. For the former, HFF cells in 24-well culture dishes were infected with approximately 50 p.f.u. of HCMV per well using the procedures detailed above. Compounds dissolved in growth medium were added in four to six selected concentrations to duplicate wells following virus adsorption. Following incubation at 370C for 7 to 10 days, cell sheets were fixed, stained and microscopic plaques were enumerated as described above. Drug effects were calculated as a percentage of reduction in number of plaques in the presence of each drug concentration compared to the number observed in the absence of drug. DHPG (ganciclovir) was used as a positive control in all experiiifts.

ELISA techniques according to standard procedures were also used to determine activity against HSV-1. Drug effects were calculated as a percentage of the reduction in virus titers in the presence of each drug concentration compared to the titer obtained in the absence of drug. Ganciclovir was used as a positive control in all experiments.

The activity of compounds against HIV-1 replication was determine by using reverse transcriptase (RT) as a marker for HIV-1. Strain $III_B$ of HIV-1 was grown in CEM cells maintained in suspension culture as detailed previously (see Kucera et al. AIDS Res. Human Retroviruses, 1993, Vol. 9, pp. 307–314). The assay measured the presence of HIV in supernatants of infected CEM cells by determining the amount of RT activity. Cells were grown, infected with HIV-1, and incubated in the presence of seven concentrations (one-half $\log_{10}$ dilutions) of the test compounds beginning at 1 or 100 μM concentration, depending on the compound to be assayed. Procedures and the RT assay were performed as detailed previously (see White et al., Antiviral Res. 1991, Vol. 16, pp. 257–266).

Assays for Cytotoxicity

Two different methods were used to evaluate cytotoxicity of the compounds. First, cytotoxicity produced in stationary HFF cells was determined by microscopical examination of cells not affected by the virus used in the plaque assay. Second the effect of compounds on KB cells during two population doubling times was determined by crystal violet staining and spectrophotometric quantitation of dye eluted from stained cells. This method has been utilized for the analysis of ganciclovir and zidovudine (See Prichard, M. N. et al. Antiviral Res. (1991) Vol. 35:1060–1065).

Antiviral activity and cytotoxicity data for four of the imidazo[1,2-a]pyridines of the present invention are presented in Table 3, along with comparison data for known antiviral agents TCRB (2,5,6-trichloro-1-(2'-β-D-ribofuranosyl)benzimidazole) and ganciclovir (DHPG).

Antiviral activity and cytotoxicity data for five of the imidazo[1,2-a]pyridine C5-nucleosides of the present invention are presented in Table 4, along with comparison data for known antiviral agent ganciclovir.

Antiviral activity and cytotoxicity data for four of the imidazo[1,2-a]pyridine C3-nucleosides of the present invention are presented in Table 5. Of particular interest are compounds +29 and −29, namely the enantiomers of 2,6,7-trichloro-3-(α-D/L-erythro-furanosyl)-imidazo[1,2-a]pyridine, which offer excellent antiviral activity while retaining very low cytotoxicity.

Antiviral activity and cytotoxicity data for two of the imidazo[1,2-a]pyridine C3-nucleosides of the present invention are presented in Table 6. Of particular interest is compound 44 which offers HIV-1 antiviral activity at non-cytotoxic concentrations.

TABLE 3

Imidazo[1,2-a]Pyridines
50% Inhibitory Concentration $IC_{50}$ (μM)

| | Antiviral Activity | | Cytotoxicity | |
|---|---|---|---|---|
| | HCMV | HSV-1 | | |
| Compound | (plaque assay in HFF cells) | (ELISA assay) | Visual (HFF cells) | Growth (KB cells) |
| Compound 12 2,6-$Cl_2$ | >100 | >100 | >100 | >100 |
| Compound 15 2,7-$Cl_2$ | >100 | >100 | >100 | >100 |
| Compound 16 2,6,7-$Cl_3$ | >100 | >100 | >100 | >100 |
| Compound 18 2,6,7,8-$Cl_4$ | >100 | >100 | >100 | >100 |
| TCRB | 9.5 | — | 15 | — |
| DHPG | 7.4 | — | >100 | — |

TABLE 4

Imidazo[1,2-a]Pyridines C5 Nucleosides
50% Inhibitory Concentration $IC_{50}$ (μM)

| | Antiviral Activity | | Cytotoxicity | |
|---|---|---|---|---|
| | HCMV | HSV-1 | | |
| Compound | (plaque assay in HFF cells) | (ELISA assay) | Visual (HFF cells) | Growth (KB cells) |
| Compound 45 β-D (no Cl) | >100 | >100 | >100 | >100 |
| Compound 36 2,6-$Cl_2$-β-D | >100 | >100 | >100 | >100 |
| Compound 38 2,6,$Cl_2$-α-D | >100 | >100 | >100 | >100 |
| Compound 42 2,6,7-$Cl_3$-β-D | >100 | >100 | >100 | >100 |
| Compound 43 2,6,7-$Cl_3$-α-D | >100 | >100 | >100 | >100 |
| DHPG | 7.4 | — | >100 | — |

TABLE 5

Imidazo[1,2-a]Pyridines C3-Nucleosides
50% Inhibitory Concentration $IC_{50}$ (μM)

| | Antiviral Activity | | Cytotoxicity | |
|---|---|---|---|---|
| | HCMV | HSV-1 | | |
| Compound | (plaque assay in HFF cells) | (ELISA assay) | Visual (HFF cells) | Growth (KB cells) |
| Compound +28 2,6,7-$Cl_3$-β-L (1208) | >100 | >100 | >100 | >100 |
| Compound −28 2,6,7-$Cl_3$-β-D (1210) | >100 | >100 | >100 | >100 |
| Compound +29 2,6,7-$Cl_3$-α-D (1209) | 4.9 | 80 | >100 | >100 |
| Compound −29 2,6,7-$Cl_3$-α-L (1207) | 17 | >100 | >100 | >100 |

TABLE 6

Imidazo[1,2-a]Pyridine C3-Nucleosides
50% Inhibitory Concentration $IC_{50}$ (μM)

| | Antiviral Activity | | | Cytotoxicity | | |
|---|---|---|---|---|---|---|
| | HCMV | HSV-1 | HIV-1 | Visual | Growth | |
| Compound | (plaque assay in HFF cells) | (ELISA assay) | (RT Assay) | (HFF cells) | (KB cells) | (CEM cells) |
| Compound 26 2,6,7-$Cl_3$-β-D/L (1211) | 32 | >100 | — | 222 | >100 | >100 |
| Compound 76 2,6,7-$Cl_3$-β-D (1265) | 32 | >100 | 14/25 | 100 | >100 | >100 |

The embodiments of this invention illustrated above are intended to aid in an understanding of the invention but are not intended to, and should not be construed to, limit in any way the invention as set forth in the following claims. Other aspects, advantages and modifications within the scope of this invention will be apparent to those skilled in the art to which this invention pertains.

What is claimed is:

1. An imidazo[1,2-a]pyridine C-nucleoside of the formula:

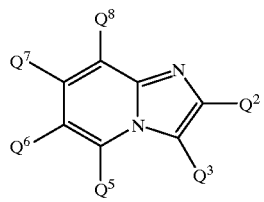

wherein
exactly one of $Q^3$ and $Q^5$ is a sugar-like moiety;
exactly one of $Q^3$ and $Q^5$ is —H;
$Q^2$, $Q^6$, $Q^7$, and $Q^8$ are independently —H, —F, —Cl, —Br, or —I; and pharmaceutically acceptable salts thereof.

2. An imidazo[1,2-a]pyridine C-nucleoside according to claim 1, wherein said sugar-like moiety is furanosyl.

3. An imidazo[1,2-a]pyridine C-nucleoside according to claim 1, wherein said sugar-like moiety is selected from the group consisting of:
ribo-furanosyl;
lyxo-furanoxyl;
erythro-furanosyl;
2',3'-dideoxy-2',3'-didehydro-erythro-furanosyl;
2',3'-dideoxy-3',4'-didehydro-erythro-furanosyl;
2',3'-dideoxy-2',3'-didehydro-ribo-furanosyl; and
2',3'-dideoxy-3',4'-didehydro-ribo-furanosyl.

4. An imidazo[1,2-a]pyridine C-nucleoside according to claim 1, wherein said compound is 2,6-dichloro-3-(furanosyl)-imidazo[1,2-a]pyridine.

5. An imidazo[1,2-a]pyridine C-nucleoside according to claim 1, wherein said compound is 2,6,7-trichloro-3-(furanosyl)-imidazo[1,2-a]pyridine.

6. An imidazo[1,2-a]pyridine C-nucleoside according to claim 1, wherein said compound is 2,6-dichloro-3-(2',3'-dideoxy-2',3'-didehydro-furanosyl)-imidazo[1,2-a]pyridine.

7. An imidazo[1,2-a]pyridine C-nucleoside according to claim 1, wherein said compound is a 2,6,7-trichloro-3-(2',3'-dideoxy-2',3'-didehydro-furanosyl)-imidazo[1,2-a]pyridine.

8. An imidazo[1,2-a]pyridine C-nucleoside according to claim 1, wherein said compound is a 2,6-dichloro-3-(2',3'-dideoxy-3',4'-didehydro-furanosyl)-imidazo[1,2-a]pyridine.

9. An imidazo[1,2-a]pyridine C-nucleoside according to claim 1, wherein said compound is 2,6,7-trichloro-3-(2',3'-dideoxy-3',4'-didehydro-furanosyl)-imidazo[1,2-a]pyridine.

10. An imidazo[1,2-a]pyridine C-nucleoside according to claim 1, wherein said compound is 2,6,7-trichloro-3-(α-D/L-erythrofuranosyl)-imidazo[1,2-a]pyridine.

11. An imidazo[1,2-a]pyridine C-nucleoside according to claim 1, wherein said compound is 2,6,7-trichloro-3-(2',3'-dideoxy-2',3'-didehydro-β-D/L-erythrofiranosyl)-imidazo[1,2-a]pyridine.

12. An imidazo[1,2-a]pyridine C-nucleoside according to claim 1, wherein said compound is 2,6,7-trichloro-3-(2',3'-dideoxy-2',3'-didehydro-β-D-ribofuranosyl)-imidazo[1,2-a]pyridine.

13. An imidazo[1,2-a]pyridine C-nucleoside according to claim 1, wherein said compound is 2,6,7-trichloro-3-(α-L-erythrofuranosyl)-imidazo[1,2-a]pyridine.

14. An imidazo[1,2-a]pyridine C-nucleoside according to claim 1, wherein said compound is 2,6,7-trichloro-3-(2',3'-dideoxy-2',3'-didehydro-β-L-erythrofuranosyl)-imidazo[1,2-a]pyridine.

15. An imidazo[1,2-a]pyridine C-nucleoside according to claim 1, wherein $Q^3$ is a sugar-like moiety and $Q^5$ is —H.

16. An imidazo[1,2-a]pyridine C-nucleoside according to claim 15, wherein $Q^2$ and $Q^6$ are —X; and $Q^7$ and $Q^8$ are —H, wherein X is independently —F, —Cl, —Br or —I.

17. An imidazo[1,2-a]pyridine C-nucleoside according to claim 15, wherein $Q^2$ and $Q^7$ are —X; and $Q^6$ and $Q^8$ are —H, wherein X is independently —F, —Cl, —Br, or —I.

18. An imidazo[1,2-a]pyridine C-nucleoside according to claim 15, wherein $Q^2$, $Q^6$ and $Q^7$ are —X; and $Q^8$ is —H, wherein X is independently —F, —Cl, —Br, or —I.

19. An imidazo[1,2-a]pyridine C-nucleoside according to claim 15, wherein $Q^2$, $Q^7$ and $Q^8$ are —X; and $Q^6$ is —H, wherein X is independently —F, —Cl, —Br, or —I.

20. An imidazo[1,2-a]pyridine C-nucleoside according to claim 15, wherein $Q^2$, $Q^6$, $Q^7$ and $Q^8$ are —X, wherein X is independently —F, —Cl, —Br or —I.

21. An imidazo[1,2-a]pyridine C-nucleoside according to claim 15, wherein said sugar-like moiety is furanosyl.

22. An imidazo[1,2-a]pyridine C-nucleoside according to claim 15, wherein said sugar-like moiety is selected from the group consisting of:
ribo-furanosyl;
lyxo-furanosyl;
erythro-furanosyl;
2',3'-dideoxy-2',3'-didehydro-erythro-furanosyl;
2',3'-dideoxy-3',4'-didehydra-erythro-furanosyl;
2',3'-dideoxy-2',3'-didehydro-ribo-furanosyl; and
2',3'-dideoxy-3',4'-didehydro-ribo-furanosyl.

23. An imidazo[1,2-a]pyridine C-nucleoside according to claim 1, wherein $Q^3$ is —H and $Q^5$ is a sugar-like moiety.

24. An imidazo[1,2-a]pyridine C-nucleoside according to claim 23, wherein $Q^2$ and $Q^6$ are —X; and $Q^7$ and $Q^8$ are —H, wherein X is independently —F, —Cl, —Br or —I.

25. An imidazo[1,2-a]pyridine C-nucleoside according to claim 23, wherein $Q^2$ and $Q^7$ are —X; and $Q^6$ and $Q^8$ are —H, wherein X is independently —F, —Cl, —Br or —I.

26. An imidazo[1,2-a]pyridine C-nucleoside according to claim 23, wherein $Q^2$, $Q^6$ and $Q^7$ are —X; and $Q^5$ is —H, wherein X is independently —F, —Cl, —Br, or —I.

27. An imidazo[1,2-a]pyridine C-nucleoside according to claim 23, wherein $Q^2$, $Q^7$ and $Q^8$ are —X; and $Q^6$ is —H, wherein X is independently —F, —Cl, —Br, or —I.

28. An imidazo[1,2-a]pyridine C-nucleoside according to claim 23, wherein $Q^2$, $Q^6$, $Q^7$ and $Q^8$ are —X, wherein X is independently —F, —Cl, —Br or —I.

29. An imidazo[1,2-a]pyridine C-nucleoside according to claim 23, wherein said sugar-like moiety is furanosyl.

30. An imidazo[1,2-a]pyridine C-nucleoside according to claim 23, wherein said sugar-like moiety is selected from the group consisting of:
ribo-furanosyl;
lyxo-furanosyl;
erythro-furanosyl;
2',3'-dideoxy-2',3'-didehydro-erythro-furanosyl;
2',3'-dideoxy-3',4'-didehydro-erythro-furanosyl;
2',3'-dideoxy-2',3'-didehydro-ribo-furanosyl; and
2',3'-dideoxy-3',4'-didehydro-ribo-furanosyl.

31. An imidazo[1,2-a]pyridine C-nucleoside according to claim 1, wherein $Q^2$ and $Q^6$ are —X; and $Q^7$ and $Q^8$ are —H, wherein X is independently —F, —Cl, —Br or —I.

32. An imidazo[1,2-a]pyridine C-nucleoside according to claim 31, wherein said sugar-like moiety is furanosyl.

33. An imidazo[1,2-a]pyridine C-nucleoside according to claim 31, wherein said sugar-like moiety is selected from the group consisting of:

ribo-furanosyl;

lyxo-furanosyl;

erythro-furanosyl;

2',3'-dideoxy-2',3'-didehydro-erythro-furanosyl;

2',3'-dideoxy-3',4'-didehydro-erythro-furanosyl;

2',3'-dideoxy-2',3'-didehydro-ribo-furanosyl; and

2',3'-dideoxy-3',4'-didehydro-ribo-furanosyl.

34. An imidazo[1,2-a]pyridine C-nucleoside according to claim 1, wherein $Q^2$ and $Q^7$ are —X; and $Q^6$ and $Q^8$ are —H, wherein X is independently —F, —Cl, —Br, or —I.

35. An imidazo[1,2-a]pyridine C-nucleoside according to claim 34, wherein said sugar-like moiety is furanosyl.

36. An imidazo[1,2-a]pyridine C-nucleoside according to claim 34, wherein said sugar-like moiety is selected from the group consisting of:

ribo-furanosyl;

lyxo-furanosyl;

erythro-furanosyl;

2',3'-dideoxy-2',3'-didehydro-erytbro-furanosyl;

2',3'-dideoxy-3',4'-didehydro-erythro-furanosyl;

2',3'-dideoxy-2',3'-didehydro-ribo-furanosyl; and

2',3'-dideoxy-3',4'-didehydro-ribo-furanosyl.

37. An imidazo[1,2-a]pyridine C-nucleoside according to claim 1, wherein $Q^2$, $Q^6$ and $Q^7$ are —X; and $Q^8$ is —H, wherein X is independently —F, —Cl, —Br, or —I.

38. An imidazo[1,2-a]pyridine C-nucleoside according to claim 37, wherein said sugar-like moiety is furanosyl.

39. An imidazo[1,2-a]pyridine C-nucleoside according to claim 37, wherein said sugar-like moiety is selected from the group consisting of:

ribo-furanosyl;

lyxo-furanosyl;

erythro-furanosyl;

2',3'-dideoxy-2',3'-didehydro-erythro-furanosyl;

2',3'-dideoxy-3',4'-didehydro-erythro-furanosyl;

2',3'-dideoxy-2',3'-didehydro-ribo-furanosyl; and

2',3'-dideoxy-3',4'-didehydro-ribo-furanosyl.

40. An imidazo[1,2-a]pyridine C-nuclcosidc according to claim 1, wherein $Q^2$, $Q^7$ and $Q^8$ are —X; and $Q^6$ is —H, wherein X is independently —F, —Cl, —Br, or —I.

41. An imidazo[1,2-a]pyridine C-nucleoside according to claim 40, wherein said sugar-like moiety is furanosyl.

42. An imidazo[1,2-a]pyridine C-nucleoside according to claim 40, wherein said sugar-like moiety is selected from the group consisting of:

ribo-furanosyl;

lyxo-furanosyl, erythro-furanosyl;

2',3'-dideoxy-2',3'-didehydro-erythro-furanosyl;

2',3'-dideoxy-3',4'-didehydro-erythro-furanosyl;

2',3'-dideoxy-2',3'-didehydro-ribo-furanosyl; and

2',3'-dideoxy-3',4'-didehydro-ribo-furanosyl.

43. An imidazo[1,2-a]pyridine C-nucleoside according to claim 1, wherein $Q^2$, $Q^6$, $Q^7$ and $Q^8$ are —X, wherein X is independently —F, —Cl, —Br or —I.

44. An imidazo[1,2-a]pyridine C-nucleoside according to claim 43, wherein said sugar-like moiety is furanosyl.

45. An imidazo[1,2-a]pyridine C-nucleoside according to claim 43, wherein said sugar-like moiety is selected from the group consisting of:

ribo-furanosyl;

lyxo-furanosyl;

erythro-furanosyl;

2',3'-dideoxy-2',3'-didehydro-erythro-furanosyl;

2',3'-dideoxy-3',4'-didehydro-erythro-furanosyl;

2',3'-dideoxy-2',3'-didehydro-ribo-furanosyl; and

2',3'-dideoxy-3',4'-didehydro-ribo-furanosyl.

46. A pharmaceutical composition comprising a compound according to claim 1, and a pharmaceutically acceptable carrier.

47. A method of inhibiting DNA or RNA viral proliferation in an in vitro cell culture infected by said virus, comprising contacting said cell culture with an effective amount of a compound according to claim 1, with the proviso that $Q^3$ is a sugar-like moiety, under suitable conditions such that viral proliferation is inhibited.

48. The method of claim 47, wherein said DNA virus is selected from the group consisting of HSV-1, HSV-2, VZV, EBV, HCMV, HHV-6, HHV-7 and HHV-8.

49. A method of inhibiting HCMV proliferation in a HCMV infected cell comprising contacting the cell with an effective amount of a compound according to claim 1, with the proviso that $Q^3$ is a sugar-like moiety, under suitable conditions such that HCMV proliferation is inhibited.

50. A method of inhibiting HSV-1 proliferation in an HSV-1 infected cell comprising contacting said cell with an effective amount of a compound according to claim 1, with the proviso that $Q^3$ is a sugar-like moiety, under suitable conditions such that HSV-1 proliferation is inhibited.

51. A method of prophylactically treating an in vitro cell culture susceptible to a DNA viral infection, comprising contacting the cell culture with an effective amount of a compound according to claim 1, with the proviso that $Q^3$ is a sugar-like moiety, under suitable conditions such that viral infection is prevented.

52. The method of claim 51, wherein the DNA virus is selected from the group consisting of HSV-1, HSV-2, VZV, EBV, HCMV, HHV-6, HHV-7 and HHV-8.

53. A method of prophylactically treating a cell of a challenged subject susceptible to HCMV infection, comprising contacting the cell with an effective amount of a compound according to claim 1, with the proviso that $Q^3$ is a sugar-like moiety. under suitable conditions such that HCMV infection is prevented.

54. A method of prophylactically treating a cell of a challenged subject susceptible to HSV-1 infection, comprising contacting the cell with an effective amount of a compound according to claim 1, with the proviso that $Q^3$ is a sugar-like moiety, under suitable conditions such that HSV-1 infection is prevented.

* * * * *

UNITED STATES PATENT AND TRADEMARK OFFICE
CERTIFICATE OF CORRECTION

PATENT NO. : 6,214,801 B1
DATED : April 10, 2001
INVENTOR(S) : Townsend et al.

It is certified that error appears in the above-identified patent and that said Letters Patent is hereby corrected as shown below:

Column 1,
First paragraph should be -- The invention described herein was made in part with government support under NIH Grant No. AI31718. Accordingly, the U.S. government may have certain rights in this invention. --

Signed and Sealed this

Twenty-seventh Day of November, 2001

Attest:

NICHOLAS P. GODICI
Attesting Officer
Acting Director of the United States Patent and Trademark Office